US007713965B2

(12) United States Patent
Ciapetti et al.

(10) Patent No.: US 7,713,965 B2
(45) Date of Patent: May 11, 2010

(54) 7-SUBSTITUTED 3-CARBOXY-OXADIAZINO-QUINOLONE DERIVATIVES, THEIR PREPARATION AND THEIR APPLICATION AS ANTI-BACTERIALS

(75) Inventors: Paola Ciapetti, Altorf (FR); Florence Chery-Mozziconacci, Strasbourg (FR); Camille G. Wermuth, Strasbourg (FR); Françoise Leblanc, Moffans (FR); Marc Schneider, Lure (FR); Sandrine Ropp, Wolfisheim (FR); Christophe Morice, Widensolen (FR); Bruno Giethlen, Altorf (FR)

(73) Assignee: Vetoquinol SA, Lure (FR)

( * ) Notice: Subject to any disclaimer, the term of this patent is extended or adjusted under 35 U.S.C. 154(b) by 0 days.

(21) Appl. No.: 12/394,918

(22) Filed: Feb. 27, 2009

(65) Prior Publication Data
US 2009/0221565 A1    Sep. 3, 2009

Related U.S. Application Data

(60) Provisional application No. 61/045,645, filed on Apr. 17, 2008.

(30) Foreign Application Priority Data
Feb. 29, 2008    (FR) .................................. 08 01129

(51) Int. Cl.
C07D 498/06    (2006.01)
A61K 31/5365    (2006.01)
(52) U.S. Cl. ..................................... 514/229.2; 544/66
(58) Field of Classification Search .................. 544/66; 514/229.2
See application file for complete search history.

(56) References Cited

U.S. PATENT DOCUMENTS

| 4,649,144 | A | 3/1987 | Matsumoto et al. |
| 4,801,584 | A | 1/1989 | Yokose et al. |
| 4,990,517 | A | 2/1991 | Petersen et al. |
| 5,354,747 | A | 10/1994 | Hansen et al. |
| 5,480,879 | A | 1/1996 | Petersen et al. |
| 5,508,278 | A | 4/1996 | Jaetsch et al. |
| 5,576,314 | A | 11/1996 | Power et al. |
| 5,679,675 | A | 10/1997 | Jaetsch et al. |
| 6,284,757 | B1 | 9/2001 | Sanner |
| 2003/0225107 | A1 | 12/2003 | Fukuda |
| 2004/0110810 | A1 | 6/2004 | Ciufolini et al. |
| 2005/0239852 | A1 | 10/2005 | Ciufolini et al. |
| 2007/0142390 | A1 | 6/2007 | Moussy et al. |
| 2008/0039466 | A1 | 2/2008 | Moussy et al. |
| 2008/0255141 | A1 | 10/2008 | Ciufolini et al. |
| 2009/0221565 | A1 | 9/2009 | Ropp et al. |

FOREIGN PATENT DOCUMENTS

| EP | 0 259 804 | 3/1988 |
| EP | 0 394 553 | 3/1989 |
| EP | 0 343 524 | 11/1989 |
| EP | 0 470 252 | 4/1990 |
| EP | 0 647 644 | 8/1994 |
| EP | 0 682 030 | 11/1995 |
| EP | 0 688 772 | 12/1995 |
| EP | 1 182 202 | 2/2002 |
| WO | WO 97/27201 | 7/1997 |
| WO | WO 2004/005295 | 1/2004 |
| WO | WO 2004/096221 | 11/2004 |
| WO | WO 2005/026154 | 3/2005 |
| WO | WO 2006/027694 | 8/2005 |
| WO | WO 2006/072831 | 12/2005 |
| WO | WO 2006/044454 | 4/2006 |
| WO | WO 2007/011284 | 1/2007 |
| WO | WO 2007/021982 | 2/2007 |
| WO | WO 2007/085760 | 2/2007 |
| WO | WO 2007/028654 | 3/2007 |

OTHER PUBLICATIONS

Snyder et al., PubMed Abstract (J. Med. Liban 48(4): 208-214,Jul.-Aug. 2000.*
Li, Qun et al.; "Synthesis and Structure—Activity Relationships of 2-Pyridones: A Novel Series Of Potent DNA Gyrase Inhibitors As Antibacterial Agents;" J. Med. Chem., vol. 39, No. 16, 1996; pp. 3070-3088.

(Continued)

Primary Examiner—Kahsay T Habte
(74) Attorney, Agent, or Firm—Harness, Dickey & Pierce, P.L.C.

(57) ABSTRACT

A subject of the invention is the compounds of formula (I):

(I)

in which
either $R_1$ represents H, OH, $NH_2$, $-(CH_2)_m-NR_aR_b$ (m=0.1 or 2),
$R_a$ and $R_b$ represent H, linear, branched or cyclic ($C_1$-$C_6$) alkyl, ($C_3$-$C_6$) cycloalkyl-($C_3$-$C_6$)— alkyl, Rc, $S(O)_2R_c$, $C(O)R_c$, $S(O)_2R_d$ or $C(O)R_d$;
or $R_a$ and $R_b$ with N form an $R_c$ radical;
$R_c$ represents a saturated, unsaturated or 5- or 6-members aromatic ring, containing 1 to 4 heteroatoms chosen from N, O and S, optionally substituted;
$R_d$ represents a linear, branched or cyclic ($C_1$-$C_6$) alkyl, optionally substituted by 1 to 4 halogens;
or $R_1$ represents $R_c$ or $CHR_eR_c$ or $CHR_eR_d$;
$R_e$ represents H, OH, $NH_2$, NH—($C_1$-$C_6$)-alk or N-($C_1$-$C_6$)-$alk_2$, or NH—($C_1$-$C_7$)-acyl or $NHR_c$;
$R_2$ represents H, $(CH_2)_m-NR_aR_b$, $R_c$, $CHR_eR_c$ or $CHR_eR_d$, and $R'_2$ represents H.

31 Claims, No Drawings

OTHER PUBLICATIONS

Tomita, Kyoji et al.; "Synthesis and Structure—Activity Relationships Of Novel 7-Substituted 1,4-Dihydro-4-Oxo-1-(2-Thiazolyl)-1,8-Naphthyridine-3-Carboxylic Acids As Antitumor Agents. Part 1;" J. Med. Chem., vol. 45, No. 25; 2002; pp. 5564-5575.

Tsuzuki, Yasunori et al.; "Synthesis and Structure—Activity Relationships Of Novel 7-Substituted 1,4-Dihydro-4-Oxo-1-(2-Thiazolyl)-1,8-Naphthyridine-3-Carboxylic Acids As Antitumor Agents. Part 2;" J. Med. Chem., vol. 47, No. 8; 2004; pp. 2097-2109.

Dax, S.L. et al.; "Quinolone Antibacterials: A Hydroxymethylation—Intramolecular Cyclization Route To Pyrido [3,2,1-*ij*]-1,3,4-Benzoxadiazines;" J. Org. Chem., vol. 57, No, 2, 1992; pp. 744-746.

Di. Cesare, P. et al.; "Fluoronaphthyridines And—Quinolones As Antibacterial Agents. 5. Synthesis And Antimicrobial Activity Of Chiral 1-*Tert*-Butyl-6-Fluoro-7-Substituted-Naphthyridones;" J. Med. Chem., vol. 35, No. 22, 1992; pp. 4205-4213.

Poumarat, F. et al.; "Mise Au Point Et Évaluation D'Une Méthode Opacimétrique Pour La Détermination De L'Antibiosensibilité De *Mycoplasma bovis* In Vitro;" Ann. Rech. Vét. (20), 1989; pp. 135-143.

Clinical And Laboratory Standards Institute (Formerly NCCLS), "Performance Standards For Antimicrobial Disk And Dilution Susceptibility Tests For Bacteria Isolated From Animals; Informational Supplement;" vol. 22, No. 6, M31-A2, ISBN 1-56238-461-9, ISSN 0273-3099, May 2002; pp. 1-86 (107 total pages).

Clinical And Laboratory Standards Institute (Formerly NCCLS), "Performance Standards For Antimicrobial Disk And Dilution Susceptibility Tests For Bacteria Isolated From Animals; Informational Supplement;" vol. 24, No. 17, M31-S1, ISBN 1-56238-534-8, ISSN 0273-3099, May 2004; pp. 1-35 (40 total pages).

Cain, James P. et al., "Design, synthesis, and biological evaluation of a new class of small molecule peptide mimetics targeting the menaocortin receptors," Bioorganic & Medicinal Chemistry Letters 16 (2006) pp. 5462-5467.

Falorni, Massimo et al., "Chiral Ligands Containing Heteroatoms. 15.1 Cyclic β-Amino Alcohols as Chiral Inductors for Enantioselective Reductions of Ketones," Tetrahedron: Asymmetry, vol. 7, No. 9, 1996, pp. 2739-2742.

Falorni, Massimo et al., "Chiral Ligands Containing Heteroatoms. 11.1 Optically Active 2-Hydroxymethyl Piperazines as Catalysts in the Enantioselective Addition of Diethylzinc to Benzaidehyde," Tetrahedron: Asymmetry, vol. 4, No. 11, 1993, pp. 2389-2398.

Falorni, Massimo et al., "Synthesis of (2R,5S)- and (2S,5S)-2-Carboxy-1,4-diaza-[4.3.0]bicyclononane as Building Blocks for the Synthesis of New Potential HIV Protease Inhibitors," Tetrahedron: Asymmetry, vol. 7, No. 7, 1996, pp. 1999-2005.

Jain, Sanjay et al., Lactam & Amide Acetals XXI. Use of Pyroglutamic Acid and Proline in Chiral Synthesis of Conformationally Constrained Piperazinones, Tetrahedron vol. 48, No. 23, 1992, pp. 4985-4998.

Peng, Hairuo et al., "Novel Bicyclic Piperazine Derivatives of Triazolotriazine and Triazolopyrimidines as Highly Potent and Selective Adenosine A2A Receptor Antagonists," J. Med. Chem. 2004, 47, Oct. 30, 2004, pp. 6218-6229.

Scapecchi, Serena et al., "Structure-activity relationship studies on unifiram (DM232) and sunifiram (DM235), two novel and potent cognition enhancing drugs," Bioorganic & Medicinal Chemistry 12 (2004), pp. 71-85.

* cited by examiner

7-SUBSTITUTED 3-CARBOXY-OXADIAZINO-QUINOLONE DERIVATIVES, THEIR PREPARATION AND THEIR APPLICATION AS ANTI-BACTERIALS

CROSS REFERENCE TO RELATED APPLICATIONS

This application claims priority to French Patent Application No. 08 01 129, filed Feb. 29, 2008 and to U.S. Provisional Application Ser. No. 61/045,645, filed Apr. 17, 2008; both of which are incorporated by reference herein.

BACKGROUND AND SUMMARY

The subject of the invention is novel 7-substituted 3-carboxy-oxadiazino-quinolone derivatives, their preparation and their application as anti-bacterials.

7-substituted 3-carboxy-oxadiazino-quinolone derivatives have been described in numerous patents, applications or publications and there may be cited for example EP 0259804, EP 0343524, EP 0688772, U.S. Pat. Nos. 4,990,517, 5,480,879, 5,679,675, or also J. Med. Chem 1996, 39, 3070-3088, J. Med. Chem 2002, 45, 5564-5575, or J. Med. Chem 2004, 47, 2097-2109.

A subject of the invention is the compounds of formula (I):

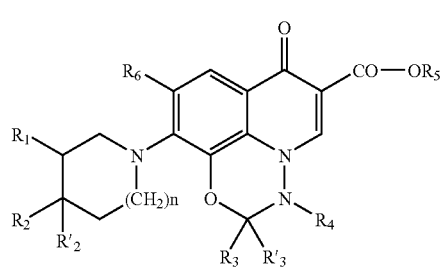

in which
either $R_1$ represents:

H, OH, $NH_2$, $-(CH_2)_m-NR_aR_b$ in which m=0.1 or 2, $R_a$ and $R_b$ are identical or different and represent H, linear, branched or cyclic $(C_1-C_6)$ alkyl, $(C_3-C_6)$ cycloalkyl-$(C_1-C_6)$-alkyl;

or also represent $R_c$, $S(O)_2R_c$, $C(O)R_c$, $S(O)_2R_d$ or $C(O)R_d$;

or $R_a$ and $R_b$ form together with the nitrogen atom, an $R_c$ radical;

$R_c$ represents a saturated, unsaturated or aromatic 5- to 6-member ring containing 1 to 4 heteroatoms chosen from N, O and S, optionally substituted by 1 to 3 $(C_1-C_6)$ alkyl radicals, said ring being linked, if appropriate, to the nitrogen atom of $NR_aR_b$ by a nitrogen atom or a carbon atom;

$R_d$ represents a linear or branched $(C_1-C_6)$ alkyl or $(C_3-C_6)$ cyclic alkyl radical, optionally substituted by 1 to 4 halogens;

or $R_1$ represents $R_c$ or $CHR_eR_c$ or $CHR_eR_d$;

$R_c$ and $R_d$ are as defined above, $R_e$ represents H, OH, $NH_2$, $NH-(C_1-C_6)$-alk or $N-(C_1-C_6)$-alk$_2$, or $NH-(C_1-C_7)$-acyl or $NHR_c$, $R_c$ being as defined above;

$R_2$ represents:

H, $(CH_2)_m-NR_aR_b$, $R_c$, $CHR_eR_c$ or $CHR_eR_d$, $R_a$, $R_b$, $R_c$, $R_d$ and $R_e$ are as defined above;

and $R'_2$ represents H;

it being understood that $R_1$ and $R_2$ cannot at the same time be H or that $R_1$ and $R_2$ or $R_2$ and $R_1$ cannot be one $(CH_2)_m-NR_aR_b$ or $R_c$ or H and the other one OH, or one H and the other one $NH_2$, or one H and the other one $(CH_2)_m-NR_aR_b$ in which $R_a$ and $R_b$ represent H or $(C_1-C_6)$ alkyl or $C(O)R_d$, in which $R_d$ represents an unsubstituted linear or branched $(C_1-C_6)$ alkyl or $(C_3-C_6)$ cyclic alkyl radical;

or $R_1$ has the above definition except H and $R_2$ and $R'_2$ together represent gem $(C_1-C_6)$ dialkyl or $(C_1-C_6)$ alkyl-oxime, or $R_2$ and $R'_2$ represent respectively $R_c$ or $R_d$ and OH, $NH_2$, $NHR_c$ or $NHR_f$, $R_c$ and $R_d$ being as defined above and $R_f$ being a $(C_1-C_7)$ acyl radical;

or $R_1$ represents H and $R_2$ and $R'_2$ together represent $(C_1-C_6)$ alkyl-oxime or one represents $R_c$ and the other one represents OH, $NH_2$, $NHR_c$ or $NHR_f$, $R_c$ and $R_f$ being defined as above;

n is 0 or 1;

$R_3$ and $R'_3$, identical or different, represent H or $(C_3-C_6)$ alkyl optionally substituted by 1 to 3 halogens or $R_3$ represents a $(C_1-C_6)$ alkoxy carbonyl group and $R'_3$ represents H;

$R_4$ represents methyl optionally substituted by one to three halogens;

$R_5$ represents H, $(C_1-C_6)$ alkyl or $(C_7-C_{12})$ arylalkyl;

$R_6$ represents H, fluorine, $NO_2$, $CF_3$ or CN;

in the form of mixtures of enantiomers or single enantiomers, as well as their addition salts with mineral and organic acids and their salts with mineral or organic bases.

The compounds of the invention have remarkable antibacterial properties which make them particularly indicated for use as medicaments in both human and veterinary medicine.

In general formula (I) and hereafter:

by linear or branched $(C_1-C_6)$ alkyl radical is meant any possible radical and in particular methyl, ethyl, propyl or isopropyl, butyl, isobutyl or tert-butyl;

by cyclic $(C_1-C_3)$ alkyl radical is meant cyclopropyl, cyclobutyl, cyclopentyl or cyclohexyl;

by arylalkyl radical is meant preferably benzyl or phenethyl;

by halogen is meant fluorine, chlorine, bromine or iodine, and preferably fluorine;

by $(C_1-C_7)$ acyl radical is meant any possible radical and in particular acetyl propionyl, butyryl or benzoyl.

When $R_c$ represents a saturated ring, this is for example a pyrrolidine, piperidine, piperazine or morpholine ring. When $R_c$ represents an unsaturated or aromatic ring, it is for example a pyrrole, furane, thiophene, pyrazole, triazole, tetrazole, thiazole, isothiazole, thiadiazole, imidazole, isoxazole, furazane, pyridine, pyrazine, pirimidine or pyridazine ring. When $R_c$ is substituted, it is in particular by one or, if appropriate, two methyl radicals.

Among the acid salts of the products of formula (I), there may be cited, among others, of those formed with mineral acids, such as hydrochloric, hydrobromic, hydroiodic, sulphuric or phosphoric acid or with organic acids such as formic, acetic, trifluoroacetic, propionic, benzoic, maleic, fumaric, succinic, tartaric, citric, oxalic, glyoxylic, aspartic, alkanesulphonic acids, such as methanesulphonic and ethanesulphonic acids, arylsulphonic acids such as benzenesulphonic and paratoluenesulphonic acids. Among the alkaline salts of the products of formula (I), there may be cited, among others, those formed with mineral alkalis such as, for example, sodium, potassium, lithium, calcium, magnesium or ammonium hydroxide or organic bases such as, for example, methylamine, propylamine, trimethylamine, diethylamine, triethylamine, N,N-dimethylethanolamine, tris (hydroxymethyl)aminomethane, ethanolamine, pyridine, piperidine, piperazine, picoline, dicyclohexylamine, morpholine, benzylamine, procaine, lysine, arginine, histidine, N-methylglucamine. A particular subject of the invention is compounds of formula (I) as defined above, in which $R_3$ and $R'_3$ represent H and $R_4$ represents methyl, as well as those in which $R_6$ represents fluorine. A further particular subject of the invention is the compounds of formula (I) in which one of the substituents $R_1$ and $R_2$ represents $(CH_2)_m$—$NR_aR_b$ in which m is 0 or 1, $R_c$, $CHR_eR_c$ or $CHR_eR_d$, and the other represents H. Among these, there may be cited more particularly those in which one of the substituents $R_1$ and $R_2$ represents $(CH_2)_m$—$NR_aR_b$ in which m is 0, and the other represents H, and quite particularly among these latter:

those in which one of the substituents $R_a$ or $R_b$ represents a 5- or 6-member aromatic ring, containing 1 to 4 heteroatoms chosen from N, O and S, optionally substituted by 1 to 3 ($C_1$-$C_6$) alkyl radicals, said ring being linked, if appropriate, to the nitrogen atom of $NR_aR_b$ by a nitrogen atom or a carbon atom, and the other represents H, and those in which one of the substituents $R_a$ or $R_b$ represents a $C(O)R_d$ radical and the other represents H.

A further particular subject of the invention is compounds of formula (I) as defined above, in which one of the substituents $R_1$ and $R_2$ represents $CHR_eR_c$ or $CHR_eR_d$ and the other represents H. A further particular subject of the invention is compounds of formula (I) as defined above, in which $R_1$ represents OH or $NH_2$ and $R_2$ and $R'_2$ represent gem ($C_1$-$C_6$) dialkyl, as well as those in which $R_1$ represents hydrogen or —$(CH_2)_m$—$NR_aR_b$ and $R_2$ and $R'_2$ represent ($C_1$-$C_6$) alkyl oxime. The preferred compounds of formula (I) according to the invention are those in which n=0.

Among compounds of the invention, there may be cited the compounds described in the experimental part, in particular those whose names follow:

8-fluoro-3-methyl-6-oxo-9-[3-(pyrazine-2-ylaminomethyl)-pyrrolidine-1-yl]-2,3-dihydro-6H-1-oxa-3,3a-diaza-phenalene-5-carboxylic acid, 8-fluoro-3-methyl-6-oxo-9-[(3-pyrazine-2-ylamino)-pyrrolidine-1-yl]-2,3-dihydro-6H-1-oxa-3,3a-diaza-phenalene-5-carboxylic acid, 8-fluoro-3-methyl-6-oxo-9-[3-(1,3,4-thiadiazol-2-ylamino)-pyrrolidine-1-yl]-2,3-dihydro-6H-1-oxa-3,3 a-diaza-phenalene-5-carboxylic acid, 8-fluoro-3-methyl-6-oxo-9-[(S)-3-(thiazol-2-ylamino)-pyrrolidine-1-yl]-2,3-dihydro-6H-1-oxa-3,3a-diaza-phenalene-5-carboxylic acid, 8-fluoro-3methyl-6-oxo-9-[3-(2,2,2-trifluoro-acetylamino)-pyrrolidine-1-yl]-2,3-dihydro-6H-1-oxa-3,3a-diaza-phenalene-5-carboxylic acid, 8-fluoro-3-methyl-6-oxo-9-[(R)-3-(2,2,2-trifluoro-acetylamino)-pyrrolidine-1-yl]-2,3-dihydro-6H-1-oxa-3,3a-diaza-phenalene-5-carboxylic acid, 9-((R,S)-4-amino-3,3-dimethyl-pyrrolidine-1-yl)-8-fluoro-3-methyl-6-oxo-2,3-dihydro-6H-1-oxa-3,3a-diaza-phenalene-5-carboxylic acid, 9-((R)-4-amino-3,3-dimethyl-pyrrolidine-1-yl)-8-fluoro-3-methyl-6-oxo-2,3-dihydro-6H-1-oxa-3,3a-diaza-phenalene-5-carboxylic acid, 9-[3-(amino-thiazol-2-yl-methyl)-pyrrolidine-1-yl]-8-fluoro-3-methyl-6-oxo-2,3-dihydro-6H-1-oxa-3,3a-diaza-phenalene-5-carboxylic acid, 8-fluoro-9-[3-(Z/E)-methoxyimino)-pyrrolidine-1-yl]-3-methyl-6-oxo-2,3-dihydro-6-H-1-oxa-3,3a-diaza-phenalene-5-carboxylic acid, 8-fluoro-9-[3-(aminomethyl)-4-methoxyimino-pyrrolidine-1-yl]-3-methyl-6-oxo-2,3-dihydro-6H-1-oxa-3,3a-diaza-phenalene-5-carboxylic acid, 8-fluoro-3-methyl-6-oxo-9-[(R)-3-(thiazol-2-ylamino)-pyrrolidine-1-yl]-2,3-dihydro-6H-1-oxa-3,3a-diaza-phenalene-5-carboxylic acid, 8-fluoro-3-methyl-6-oxo-9-[(S)-3-(2,2,2-trifluoro-acetylamino)-pyrrolidine-1-yl]-2,3-dihydro-6H-1-oxa-3,3a-diaza-phenalene-5-carboxylic acid, 9-((S)-4-amino-3,3-dimethyl-pyrrolidine-1-yl)-8-fluoro-3-methyl-6-oxo-2,3-dihydro-6H-1oxa-3,3a-diaza-phenalene-5-carboxylic acid, as well as their salts.

The compounds of the invention can be prepared by a method characterized in that a compound of formula (II) is treated:

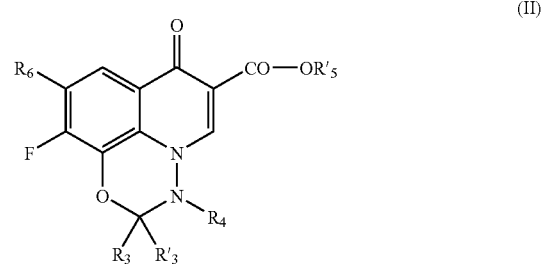

(II)

in which $R_3$, $R'_3$, $R_4$ and $R_6$ are as defined above and $R'_5$ has the values of $R_5$ defined above or represents another group protecting the carboxylic function, by a compound of formula (III):

(III)

in which $R_1$, $R_2$, $R'_2$ and n are as previously defined, in the presence of a base, then, if appropriate, the protective groups present are eliminated.

The procedure is carried out preferably in a sealed chamber, in solution in the pyridine, at the reflux temperature of the latter. The base used is preferably a tertiary amine, for example triethylamine, N-methyl morpholine or also DBU. When $R'_5$ represents a protective group, it can in particular be a ($C_1$-$C_6$) alkyl, a ($C_2$-$C_6$) alkenyl, or a ($C_7$-$C_{14}$) arylalkyl. After final elimination of the protective group $R'_5$, the acid obtained can if desired be reesterified to form a compound in which $R_5$ is different from hydrogen. The compounds of the invention in which $R_2$ and $R'_2$ represent ($C_1$-$C_6$) alkyl-oxime can also be prepared by a method characterized in that a compound of formula (IV) is treated:

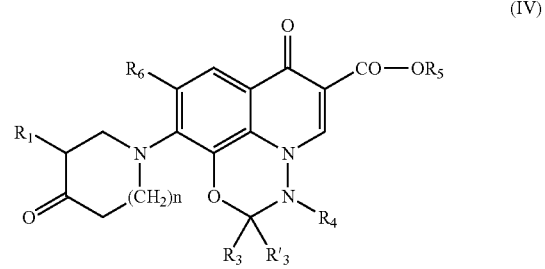

(IV)

by an alkoxylamine or a salt of the latter.

The procedure is carried out for example by action of an alkoxylamine chloride, in the presence of a base, in particular an alkaline carbonate or bicarbonate, in solution in an alkanol or in an alkanol-tetrahydrofurane-water mixture.

The compound of formula (IV) can be prepared from the corresponding alcohol, for example by a Swern type oxidation reaction, in the presence of oxalyl chloride, dimethylsulphoxide and a base, for example an amine such as triethylamine. Certain compounds of formula (III) are known, even commercially available, or can be prepared by methods known to a person skilled in the art. Preparation methods are given below, as well as in the experimental part. The compound of formula (III) in which $R_1$ or $R_2$ represents a —$(CH_2)_m$—$NR_aR_b$ radical in which $R_a$ and/or $R_b$ represent $R_c$ or $R_d$ can be prepared from a compound of formula (V):

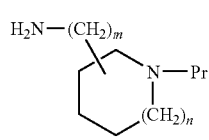

(V)

in which Pr represents a group protecting the nitrogen of the ring and m and n are as defined above, by action of a compound of formula (VI):

$R_c$-Hal or $R_d$-Hal    (VI)

in which $R_c$ and $R_d$ are defined as previously and Hal represents a halogen, in the presence of a strong base, followed by deprotection of the nitrogen of the ring.

The procedure is carried out for example in the presence of an alkaline alkoxide, in solution in a solvent such as toluene. Hal is preferably a chlorine or a bromine.

The compound of formula (III) in which $R_1$ or $R_2$ represents a —$(CH_2)_m$—$NR_aR_b$ radical in which $R_a$ or $R_b$ or $R_a$ and $R_b$ represent $R_c$ can also be prepared from a compound of formula (VII):

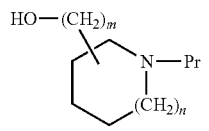

(VII)

in which m, n and Pr are defined as previously, by action of a compound of formula (VIII):

$R_c$—NHP or $R_c$—NH    (VIII)

in which $R_c$ and Pr are defined as previously, in the presence of triphenylphosphine and diethyldiazadicarboxylate, in tetrahydrofurane, followed by deprotection of the nitrogen atoms. The compound of formula (III) in which $R_1$ or $R_2$ represents a —$(CH_2)_m$—$Nr_aR_b$ radical in which $R_a$ or $R_b$ or $R_a$ and $R_b$ represent $C(O)R_c$ or $C(O)R_d$ can be prepared from a compound of formula (V) as defined above, by action of a compound of formula (IX):

$R_c$—COOH or $R_d$—COOH    (IX)

by a peptide coupling reaction in the presence of EDCI/HOBt in solution in a solvent such as DMF, or by action of a corresponding acid halide or its corresponding anhydride, in the presence of a base, for example an amine such as triethylamine, in a solvent such as dichloromethane, followed by deprotection of the nitrogen of the ring.

The compound of formula (III) in which $R_1$ or $R_2$ represents a $(CH_2)_m$—$NR_aR_b$ radical in which $R_a$ or $R_b$ or $R_a$ and $R_b$ represent $S(O)_2R_c$ or $S(O)_2R_d$ can be prepared from a compound of formula (V) as defined above, by action of a corresponding alkylsulphonic acid anhydride, in the presence of a base, for example an amine such as triethylamine, in a solvent such as dichloromethane, followed by deprotection of the nitrogen of the ring. The compound of formula (III) in which $R_1$ or $R_2$ represents a —$(CH_2)_m$—$NR_aR_b$ radical in which one of $R_a$ and $R_b$ represents H and the other represents an $R_c$ radical of 4,5-dihydro-thiazol-2-yl type can be prepared from a compound of formula (V) as defined above, by action of the thiocarbonylimidazole, in order to obtain the corresponding thiocyanate which is treated with 2-chloroethylamine, or its hydrochloride, in the presence of a base, for example triethylamine, followed by deprotection of the nitrogen of the ring.

The compound of formula (III) in which $R_1$ or $R_2$ represents a —$(CH_2)_m$—$NR_aR_b$ radical in which $R_a$ and $R_b$ together form an $R_c$ radical can be prepared either from a compound of formula (VI) as defined above, by action of a compound H—$R_c$, H being fixed to a nitrogen atom of the Rc ring, in the presence of diethylazadicarboxylate and triphenylphosphine in the THF, either from a reactive derivative of the hydroxy of the compound of formula (VI), in particular a mesylate, by action of the same H—$R_c$ compound, in the presence of sodium hydride in DMF, followed by deprotection of the nitrogen of the ring. The compound of formula (III) in which $R_1$ or $R_2$ represents a —$(CH_2)_m$—$NR_aR_b$ radical in which m is equal to 0 and $R_a$ and $R_b$ together form an $R_c$ radical of [1.2,3]-triazol-1-yl type can also be prepared from a compound of formula (X):

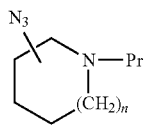

(X)

in which Pr and n are defined as previously, by action of the bicyclo[2,2,1]hepta-2,5-diene, followed by deprotection of the nitrogen of the ring.

The compound of formula (III) in which $R_1$ or $R_2$ represents an $R_c$ radical of 1H-tetrazole-5-yl type can also be prepared from a reagent derivative of the hydroxy of the compound of formula (VII), in particular a mesylate, by action of the tetrabutylammonium cyanide in acetonitrile, in order to obtain the corresponding cyanide derivative, which is treated with sodium azide in the presence of a base, for example an amine such as triethylamine, in a solvent such as toluene, followed by deprotection of the nitrogen of the ring. The compound of formula (III), if appropriate in protected form, in which $R_1$ represents OH or NH2 and $R_2$ and $R'_2$ represent gem dialkyl can be prepared by methods known to a person skilled in the art and in particular by the method described by Di Cesare et al, J Med Chem 1992, 35, (22), 4205-13. The compound of formula (III), if appropriate in protected form, in which $R_1$ represents H and $R_2$ and $R'_2$ represent respectively $R_d$ and OH, $NH_2$ or $NHR_f$, can be prepared by methods known to a person skilled in the art and in particular by the method described by Britton et al, WO0644454, or by Matsumoto et al, U.S. Pat. No. 4,649,144, or by Giordanetto et al, WO0711284, or also by Hossain et al, WO04/5295.

The compound of formula (III), if appropriate in protected form, in which $R_1$ represents H and $R_2$ and $R'_2$ represent respectively $R_c$ and OH can be prepared from the corresponding keto compound, by action of an $R_c$-Hal compound, in particular $R_c$—Br, in the presence of a strong base, in particular butyl lithium, in solution in the tetrahydrofurane, followed if appropriate by deprotection of the nitrogen of the ring. The compound of formula (III) in protected form at the nitrogen of the ring, in which $R_1$ represents $CHR_eR_c$ or $CHR_eR_d$, $R_e$ being an OH, can be prepared from the corresponding 2-keto compound, by action of an ester-type compound of formula $R_cCOOalk$ or $R_dCOOalk$, $R_c$ and $R_d$ being as defined above, in the presence of lithium diisopropylamide in THF, in order to obtain a compound of formula (XI):

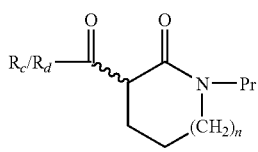

(XI)

in which $R_c$, $R_d$, n and Pr are as previously defined, which is reduced by potassium borohydride in methanol, in order to obtain a compound of formula (XII):

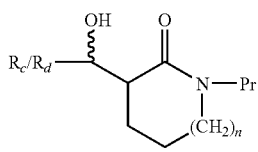

(XII)

which is reduced by $LiAlH_4$ in the presence of aluminium chloride in THF. The compound is then deprotected at the nitrogen of the ring. A method of this type is described in application WO2005/026154 and in the experimental part.

The compound of formula (III) in protected form, in which $R_1$ represents $CHR_eC_c$ or $CHR_eR_d$, $R_c$ being an OH, can also be prepared from the compound of formula (XIII):

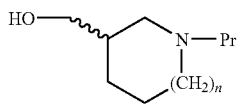

(XIII)

in which Pr and n are as previously defined, by action of oxalyl chloride in DMSO in the presence of a base such as triethylamine, in order to obtain a compound of formula (XIV):

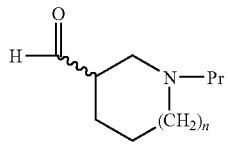

(XIV)

in which n and Pr are as previously defined, which is treated with a compound of $R_c$-Hal or $R_d$-Hal type, Hal being in particular a bromine, in the presence of a base such as butyl lithium. The compound is then deprotected. A method of this type is described in application WO2005/026154 and further in the experimental part.

The compound of formula (III) in protected form, in which $R_1$ represents $CHR_eR_c$ or $CHR_eR_d$, $R_e$ being a $NH_2$ or $NHR_f$, can be prepared from the compound obtained above, the OH function of which is activated by action of methanesulphonyl chloride in the presence of a base, for example triethylamine, within dichloromethane, then treated with sodium azide in DMF, in order to obtain the compound of formula (XV):

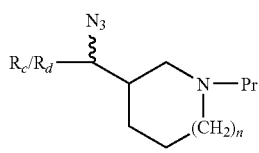

(XV)

which is reduced by hydrogen in the presence of palladium over carbon with an alkanol. The compound is isolated in protected form regarding the nitrogen of the ring. The compound is then deprotected. A method of this type is described in patent EP 1182202 and further in the experimental part.

Protection of the heterocyclic nitrogen and the amines is carried out in particular, according to circumstances, in the form of benzyle or trityle derivatives, in the form of carbamates, in particular allyl, benzyl, phenyl or tertbutyl, or also in the form of silyl derivatives such as dimethyl, trimethyl, triphenyl tertbutyl or also diphenyl tertbutyl-silyl derivatives. Deprotection is carried out, according to the nature of the protective group, by sodium or lithium in liquid ammonia, by hydrogenolysis or using soluble palladium 0 complexes, by action of an acid, or by action of tetrabutylammonium fluoride or strong bases such as sodium hydride or potassium tert-butylate. These reactions are well known to a person skilled in the art and examples are given hereafter in the experimental part. The compound of formula (II) is generally known and can be prepared by the methods described in U.S. Pat. No. 4,801,584.

The compound of formula (II) in which $R_3$ and/or $R'_3$ represent/s an alkyl radical optionally substituted by 1 to 3 halogens can be prepared from a compound of formula (II) in which $R_3$ and $R'_3$ represent a hydrogen, which is hot-treated with an alkaline aqueous base then neutralized, in order to obtain the compound of formula (XVI):

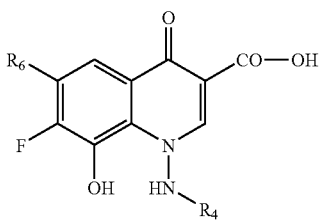

(XVI)

in which R₄, R'₅ and R₆ are defined as above, which is treated in dioxane at boiling point by a compound of formula (XVII)

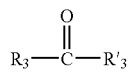

(XVII)

in which R₃ and R'₃ are defined as above.

The compound of formula (II) in which R₄ represents a methyl radical substituted by 1 to 3 halogens can be prepared according to a method of the type described in U.S. Pat. No. 4,801,584. As stated above, the compounds of formula (I) can be in the form of enantiomers or mixtures of enantiomers essentially at position 9 of the ring. The compounds of formula (I) are obtained without racemization and as a result enantiomers can be obtained by using the corresponding enantiomer of the compound of formula (III) or (IV). The compounds according to the invention have remarkable antibacterial properties and these properties manifest themselves over a wide spectrum of gram (−) bacteria, but also a wide spectrum of gram (+). This balanced antibacterial activity distinguishes them from the similar compounds of the prior art, for example marbofloxacine or also ofloxacine, and means that they are particularly indicated for use as medicaments in human medicine, but also in veterinary medicine for which there is a need for compounds which are particularly active in relation to these bacteria. Thus the compounds are active in particular on gram (+) bacteria such as *Streptococcus uberis* or *Staphylococcus aureus*, but also *Mycoplasma bovis* or *bovirhinis*, or *Clostridium perfringens* or *Enterococcus faecalis*, while still being remarkably active on gram (−) bacteria such as *Mannheimia haemolytica, Bordetella bronchiseptica, Escherichia coli* or *Pseudomonas aeruginosa*. These properties make said products, as well as their salts with pharmaceutically acceptable acids and bases, suitable for use as medicaments in the treatment of conditions with susceptible germs and in particular those involving staphylococci, such as staphylococcal septicaemia, malignant staphylococcal infection of the face or skin, pyoderma, septic or suppurating sores, anthrax, phlegmon, erysipeles, primitive or post-influenzal acute staphylococcal infections, bronchial pneumonia, pulmonary suppurations.

These products can also be used as medicaments in the treatment of colibacilloses and associated infections, in *Proteus, Klebsiella, Pseudomonas* or also *Salmonella* infections and in other conditions caused by gram (−) bacteria. A further subject of the present invention is therefore, as medicaments and in particular antibiotic medicaments, the products of formula (I) as defined above as well as their salts with pharmaceutically acceptable acids and bases.

More particularly, a subject of the invention is, as medicaments, the preferred products of formula (I) mentioned above, in particular including the compounds whose names follow:

8-fluoro-3-methyl-6-oxo-9-[3-(pyrazine-2-ylaminomethyl)-pyrrolidine-1-yl]-2,3-dihydro-6H-1-oxa-3,3a-diaza-phenalene-5-carboxylic acid, 8-fluoro-3-methyl-6-oxo-9-(3-pyrazine-2-ylamino)-pyrrolidine-1-yl)-2,3-dihydro-6H-1-oxa-3,3a-diaza-phenalene-5-carboxylic acid, 8-fluoro-3-methyl-6-oxo-9-[3-(1,3,4-thiadiazol-2-ylamino)-pyrrolidine-1-yl]-2,3-dihydro-6H-1-oxa-3,3a-diaza-phenalene-5-carboxylic acid, 8-fluoro-3-methyl-6-oxo-9-[(S)-3-(thiazol-2-ylamino)-pyrrolidine-1-yl]-2,3-dihydro-6H-1-oxa-3,3a-diaza-phenalene-5-carboxylic acid, 8-fluoro-3methyl-6-oxo-9-(3-(2,2,2-trifluoro-acetylamino)-pyrrolidine-1-yl)-2,3-dihydro-6H-1-oxa-3,3a-diaza-phenalene-5-carboxylic acid, 8-fluoro-3-methyl-6-oxo-9-((R)-3-(2,2,2-trifluoro-acetylamino)-pyrrolidine-1-yl(-2,3-dihydro-6H-1-oxa-3,3a-diaza-phenalene-5-carboxylic acid, 9-((R,S)-4-amino-3,3-dimethyl-pyrrolidine-1-yl)-8-fluoro-3-methyl-6-oxo-2,3-dihydro-6H-1-oxa-3,3a-diaza-phenalene-5-carboxylic acid, 9-((R)-4-amino-3,3-dimethyl-pyrrolidine-1-yl)-8-fluoro-3-methyl-6-oxo-2,3-dihydro-6H-1-oxa-3,3a-diaza-phenalene-5-carboxylic acid, 9-(3-(amino-thiazol-2-yl]-methyl)-pyrrolidine-1-yl]-8-fluoro-3-methyl-6-oxo-2,3-dihydro-6H-1-oxa-3,3a-diaza-phenalene-5-carboxylic acid, 8-fluoro-9-[3-((Z/E)-methoxyimino)-pyrrolidine-1-yl]-3-methyl-6-oxo-2,3-dihydro-6-H-1-oxa-3,3a-diaza-phenalene-5-carboxylic acid, 8-fluoro-9-[3-(aminomethyl)-4-methoxyimino-pyrrolidine-1-yl]-3-methyl-6-oxo-2,3-dihydro-6H-1-oxa-3,3a-diaza-phenalene-5-carboxylic acid, 8-fluoro-3-methyl-6-oxo-9-[(R)-3-(thiazol-2-ylamino)-pyrrolidine-1-yl]-2,3-dihydro-6H-1-oxa-3,3a-diaza-phenalene-5-carboxylic acid, 8-fluoro-3-methyl-6-oxo-9-[(S)-3-(2,2,2-trifluoro-acetylamino)-pyrrolidine-1-yl]-2,3-dihydro-6H-1-oxa-3,3a-diaza-phenalene-5-carboxylic acid, 9-((S)-4-amino-3,3-dimethyl-pyrrolidine-1-yl)-8-fluoro-3-methyl-6-oxo-2,3-dihydro-6H-    oxa-3,3a-diaza-phenalene-5-carboxylic acid, as well as their salts.

A subject of the invention is also the pharmaceutical compositions containing, as active ingredient, at least one of the medicaments according to the invention as defined above.

These compositions can be administered by oral, rectal, parenteral, in particular intramuscular route, by respiratory route or by local route in topical application to the skin and mucous membranes. The compositions according to the invention can be solid or liquid and be present in the pharmaceutical forms commonly used in human medicine, such as for example, plain or sugar-coated tablets, gelatin capsules, granules, suppositories, injectable preparations, ointments, creams, gels; they are prepared according to the customary methods. The active ingredient/s can be incorporated in same, using excipients which are customarily used in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting agents, dispersants or emulsifiers, preservatives. These compositions can in particular be present in the form of a powder intended to be dissolved extemporaneously in an appropriate vehicle, for example, non-pyrogenic sterile water. The dose administered varies according to the condition treated, the patient in question, the administration route and the product envisaged. It can, for example, be comprised between 0.25 g and 10 g per day, by oral route in humans, with the product described in Example 1 or also comprised between 0.25 g and 10 g per day by intramuscular or intravenous route.

DETAILED DESCRIPTION

The following examples illustrate the invention. In the following examples and, if applicable, in the description above, the abbreviations of chemical names have the following meanings:
EDCI: 1-(3-dimethylaminopropyl)-3-ethylcarbodiimide,
HOBt: 1-hydroxybenzotriazole,
DBU: 1,8-diaza-bicyclo-[5,4,0]-undec-7-ene,
TNOC: 8,9-difluoro-3-methyl-6-oxo-2,3,3a,6-tetrahydronaphtho-[1,8-de][1.3]oxazine-5-carboxylic acid,
ACN: acetonitrile,
THF: tetrahydrofurane,
DMF: dimethylformamide,
LiHMDS: lithium-hexamethyldisilylazide,
DMAP: dimethylaminopyridine,
TFA: trifluroacetic acid,
Boc: tert-butoxycarbonyl,
CBz: benzyloxycarbonyl
MS: mass spectrum,
ESI$^+$: positive ion electrospray ionization.
NMR: The spectra were determined on spectrometers of the 300 or 400 MHz type, the proton and carbon spectra being respectively recorded at 300 and 75 MHz or 400 and 100 MHz, in solution in CDCl$_3$, or DMSO-d$_6$, MeOH-d$_4$. The values recorded are expressed in δ (ppm) and represent the s, d, t, quad, dd and m values. The constant JAB is expressed in Hz. Unless otherwise indicated, the reactions are carried out under dry inert gas and at ambient temperature.

"General method A" (coupling) consists of reacting the product "TNOC" (1.0 equivalent) and the aminated derivative in suspension in pyridine (0.2M) in a sealed chamber overnight at 120° C. under stirring. The solvent is evaporated off and toluene and/or methanol are added. After concentration to dryness, the crude product is triturated in methanol and separated then dried.

"General method B" (Boc deprotection) consists of adding a large excess of TFA to a solution in dichloromethane at 0° C. of protected amino derivative (N-Boc). The reaction is carried out at ambient temperature and followed by chromatography over silica. The solution is concentrated to dryness and toluene and/or methanol are added. The crude product is obtained in the form of a trifluoroacetate.

"General method C" (peptide coupling) consists of adding 1.2 to 2.0 equivalents of EDCI and 1.2 to 2.0 equivalents of HOBt or DMAP and 1.2 to 2.0 equivalents of heteroaryl carboxylic acid, at 0° C., to a 0.2 to 0.6M solution within DMF of protected amino(piperidine) derivative N-Boc or N-CBz. The mixture is maintained under stirring at ambient temperature for 16 to 18 hours, then diluted with ethyl acetate and washed with water. The solution is then dried and concentrated to dryness under reduced pressure, then the residue is purified by chromatography over silica eluting with the cyclohexane-ethyl acetate mixture.

EXAMPLE 1

Preparation of 8-fluoro-3-methyl-6-oxo-9-[3-(pyrazin-2-ylaminomethyl)-pyrrolidin-1-yl]-2,3-dihydro-6H-1-oxa-3,3a-diaza-phenalene-5-carboxylic acid (5a)

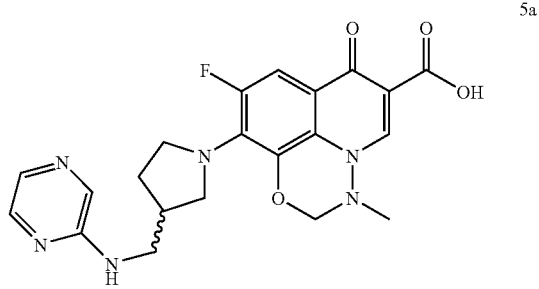

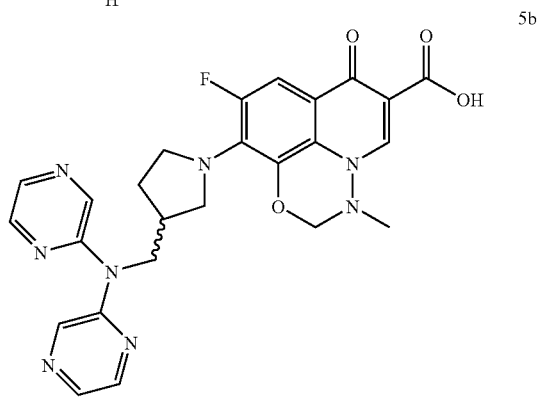

Step A: Preparation of 3a and 3b

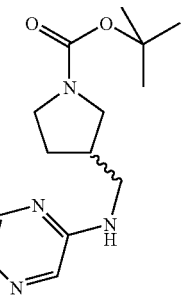

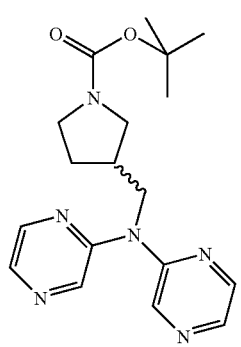

In a sealed tube, 40 mL of dry toluene was degazed with Argon during 15 minutes, palladium acetate (165 mg, 0.24 mmol, 0.04 eq.) and racemic-2,2'-bis(diphenylphosphino)-,1'-binaphthyl (152 mg, 0.24 mmol, 0.04 eq.) were added and the mixture was degazed with Argon for 10 minutes. Then 2-chloropyrazine (700 mg, 6.11 mmol, 1.0 eq.), 3-aminomethyl-pyrrolidine-1-carboxylic acid tert-butyl ester (1.5 g, 7.33 mmol, 1.2 eq.) and sodium tert-butoxide (822 mg, 8.55 mmol, 1.4 eq.) were added and the mixture was stirred at 70° C. overnight. The reaction was concentrated in vacuum. The resulting crude product was purified by flash chromatography on silica gel, eluting with cyclohexane-ethyl acetate (1:1 to 0:1) to afford a mixture of 3a and 3b (900 mg, 2:1, over yield 38%).

Step B: Preparation of 4a and 4b

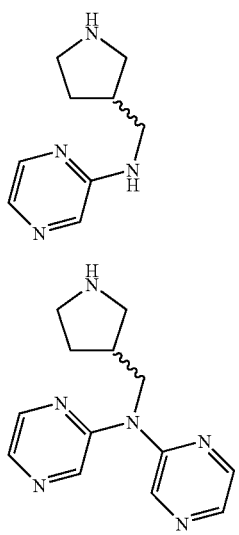

The mixture of 3a and 3b (900 mg) was dissolved in dichloromethane (25 mL) and trifluoroacetic acid (3 mL) was added. The mixture was stirred at room temperature for 6 hours. The reaction was concentrated in vacuum and co-evaporated with toluene and methanol. The residue was purified by flash chromatography on silica gel, eluting with dichloromethane—7N NH$_3$ methanol (gradient from 5% to 100% of 7N NH$_3$ methanol) 4a and 4b were separated during the flash chromatography purification to afford quantitatively 4a and 4b as colorless oils.

4a: MS (ESI$^+$) (+0.1% HCOOH): 179.21 [C$_9$H$_{14}$N$_4$+H]$^+$ (m/z)

4b: MS (ESI$^+$) (+0.1% HCOOH): 257.14 [C$_{13}$H$_{16}$N$_6$+H]$^+$ (m/z)

Step C: Preparation of 8-fluoro-3-methyl-6-oxo-9-[3-(pyrazin-2-ylaminomethyl)-pyrrolidin-1-yl]-2,3-dihydro-6H-1-oxa-3,3a-diazaphenalene-5-carboxylic acid (5a)

In a sealed tube, 8,9-difluoro-3-methyl-6-oxo-2,3,3a,6-tetrahydronaphto[1,8-de][1,3]oxazine-5-carboxylic acid—TNOC -(200 mg, 0.71 mmol, 1.0 eq.) and 4a (447 mg, 2.51 mmol, 3.53 eq.) were suspended in 3 mL of dry pyridine and 1 mL of N-methylmorpholine. The reaction mixture was stirred at 120° C. for 16 hours. The reaction was cooled to room temperature and the precipitate was filtered. The precipitate was triturated with dichloromethane and methanol and then evaporated. The residue was sonicated in ethanol, refluxed and then filtrated to afford the title compound as a yellow solid (275 mg, 74%)

HPLC (gradient 20% to 80% ACN in H$_2$O): >95%

MS (ESI$^+$) (+0.1% HCOOH): 441.2 [C$_{21}$H$_{21}$FN$_6$O$_4$+H]$^+$ (m/z)

mp=238-240° C.

EXAMPLE 2

9-{3-[di-(pyrazin-2-yl-amino)-methyl]pyrrolidin-1-yl}8-fluoro-3-methyl-6-oxo-2,3-dihydro-6H-1-oxa-3,3a-diaza-phenalene-5-carboxylic acid (5b)

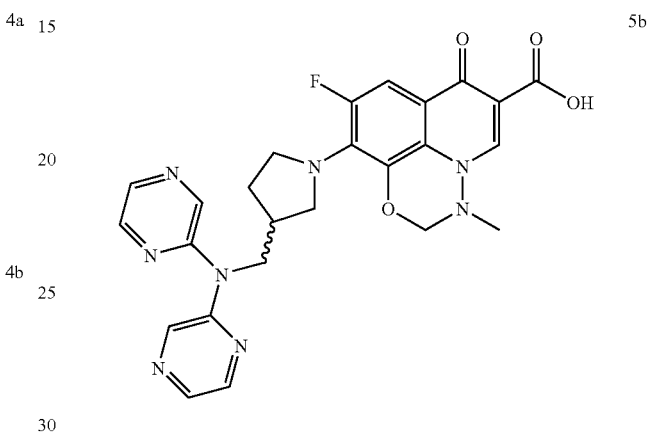

The compound 5b was obtained from TNOC (180 mg, 1.0 eq.) 4b (330 mg, 1.29 mmol, 2.02 eq.) following the procedure described for the preparation of 5a. The mixture was evaporated and co-evaporated with toluene, sonicated with ethanol, refluxed and filtrated to afford the title compound as a yellow solid (145 mg, 43%).

HPLC (gradient 20% to 80% ACN in H$_2$O): >95%

MS (ESI$^+$) (+0.1% HCOOH): 519.0 [C$_{25}$H$_{23}$FN$_8$O$_4$+H]$^+$ (m/z)

mp=213-215° C.

EXAMPLE 3

9-{3-[di-(pyridin-2-yl-amino)-methyl]pyrrolidin-1-yl}8-fluoro-3-methyl-6-oxo-2,3-dihydro-6H-1-oxa-3,3a-diaza-phenalene-5-carboxylic acid (5c)

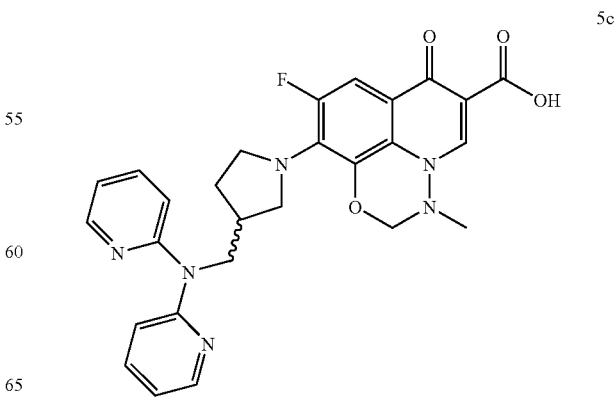

Step A: Preparation of 3c

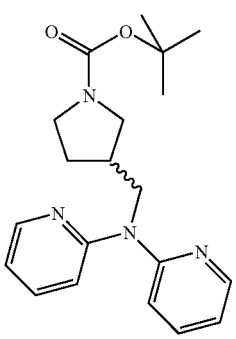

Utilizing the procedure described for the preparation of 3b except substituting 2-chloropyrazine for 2-chloropyridine (4.4 mmol). The resulting crude product was purified by flash chromatography on silica gel, eluting with cyclohexane-ethyl acetate (1:1 to 2:8) the title compound was obtained as a colorless oil (0.5 g, 32%).

Step B: Preparation of 4c

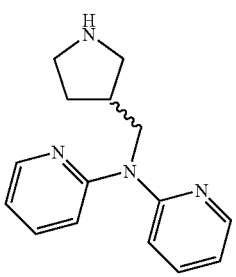

3c (1.4 g, 3.9 mmol) was dissolved in dichloromethane (40 mL) and 4N HCl in dioxane (10 mL) was added. The mixture was stirred at room temperature for 4 hours. The reaction was concentrated in vacuum. The residue was purified by flash chromatography on silica gel, eluting with dichloromethane—7N $NH_3$ in methanol (gradient from 5% to 20% of 7N $NH_3$ in methanol). The title compound was obtained as colorless oil (0.7 g, 70%).

MS (ESI$^+$) (+0.1% HCOOH): 255.15 [$C_{15}H_{18}N_4$+H]$^+$ (m/z)

Step C: 9-{3-[di-pyridin-2-yl-amino)-methyl]pyrrolidin-1-yl}8-fluoro-3-methyl-6-oxo-2,3-dihydro-6H-1-oxa-3,3a-diaza-phenalene-5-carboxylic acid (5c)

The compound 5c was obtained from TNOC (259 mg, 0.92 mmol, 1.0 eq.) and 4c (700 mg, 2.76 mmol, 3.0 eq.) in 5 mL of pyridine and N-methylmorpholine (0.2 mL, 1.84 mmol, 2.0 eq.) following the same procedure described for 5b. The mixture was evaporated, the residue was triturated in water and the precipitate was filtrated. The solid was triturated with methanol and filtrated. The crude residue was purified by preparative TLC purification eluting with dichloromethane and 5% of methanol to afford the title compound as a yellow solid (249 mg, 52%)

HPLC (gradient 5% to 80% ACN in $H_2O$): >99%

MS (ESI$^+$) (+0.1% HCOOH): 517.14 [$C_{27}H_{25}FN_6O_4$+H]$^+$ (m/z)

mp=199° C.

EXAMPLE 4

8-Fluoro-3-methyl-6-oxo-9-[3-(thiazol-2-ylaminomethyl)-pyrrolidin-1-yl]-2,3-dihydro-6H-1-oxa-3,3a-diaza-phenalene-5-carboxylic acid (10a)

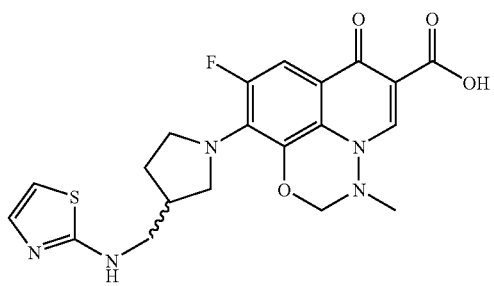

Step A: Preparation of 8a

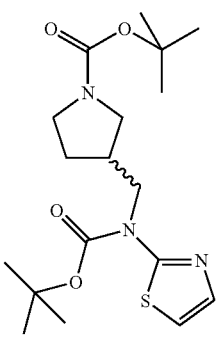

To a 0° C. solution of the commercially available 3-hydroxymethyl-pyrrolidine-1-carboxylic acid tert-butyl ester 6 (1.5 g, 7.19 mmol, 1.2 eq. prepared according WO2007/21982) in dry THF (25 mL), triphenylphosphine (2.4 g, 8.98 mmol, 1.5 eq.) was added. After complete dissolution, diethylazodicarboxylate –40% w/v in toluene-(4 mL, 8.98 mmmol, 1.5 eq.) was added dropwise followed by thiazol-2-yl-carbamic acid tert-butyl ester 7a (1.2 g, 5.99 mmol, 1.0 eq.). The mixture was stirred at room temperature for 18 hours. The reaction was evaporated under reduced pressure. The resulting crude product was purified by flash chromatography on silica gel, eluting with cyclohexane-ethyl acetate (9:1 to 8:2) to afford 8a as a colorless gum (1.95 g, 85%)

Tetrahedron letters 1995, 36, 36, 6463-6566

Step B: Preparation of 9a

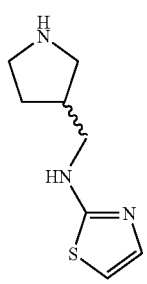

8a (1.95 g, 5.08 mmol, 1.0 eq.) was dissolved in ethyl acetate (10 mL) and 4N HCl in dioxane (10 mL) was added. The mixture was stirred at room temperature for 6 hours. The reaction was concentrated in vacuum. The residue was purified by flash chromatography on silica gel, eluting with dichloromethane—methanol (gradient from 5% to 10% methanol) then dichloromethane—7N NH$_3$ in methanol (gradient from 4% to 70% of 7N NH$_3$ in methanol). The title compound was obtained as a colorless oil (915 mg, 95%).

MS (ESI$^+$) (+0.1% HCOOH): 184.23 [C$_8$H$_{13}$N$_3$S+H]$^+$ (m/z)

Step C: 8-Fluoro-3-methyl-6-oxo-9-[3-(thiazol-2-ylaminomethyl)-pyrrolidin-1-yl]-2,3-dihydro-6H-1-oxa-3,3a-diaza-phenalene-5-carboxylic acid (10a)

Following the procedure described for the preparation of 5a, 10a was obtained from TNOC (450 mg, 1.59, 1.0 eq.) and 9a (915 mg, 5.0 mmol, 3.1 eq.) to afford the title compound as a yellow solid (421 mg, 60%). An analytical sample was obtained by preparative TLC purification eluting with dichloromethane—methanol (gradient from 2.5% to 5% of methanol).

HPLC (gradient 5% to 80% ACN in H$_2$O): >95%
MS (ESI$^+$) (+0.1% HCOOH): 446.1 [C$_{20}$H$_{20}$FN$_5$O$_4$S+H]$^+$ (m/z)
mp=268-270° C.

EXAMPLE 5

8-Fluoro-3-methyl-9-{3-[(5-methyl-[1,3,4]oxadiazol-2-ylamino)-methyl]-pyrrolidin-1-yl}-6-oxo-2,3-dihydro-6H-1-oxa-3,3a-diaza-phenalene-5-carboxylic acid (10b)

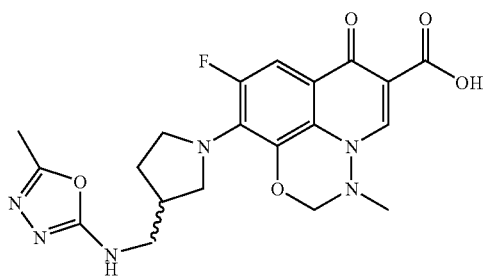

Step A: Preparation of 7b

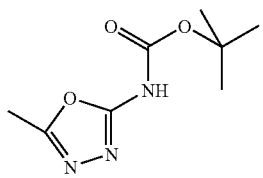

5-Methyl-[1,3,4]oxadiazol-2-ylamine (500 mg, 5.04 mmol, 1.0 eq.) was dissolved in 5 mL of dry pyridine and di-tert-butyl dicarbonate (1.1 g, 5.04 mmol, 1.0 eq.) was added, the mixture was stirred at 70° C. for 16 hours. The reaction was evaporated and co-evaporated with toluene. The resulting crude product was purified by flash chromatography on silica gel, eluting with cyclohexane-ethyl acetate (9:1 to 0:1) to afford 7b (513 mg, 51%) as a white solid.

Step B: Preparation of 8b

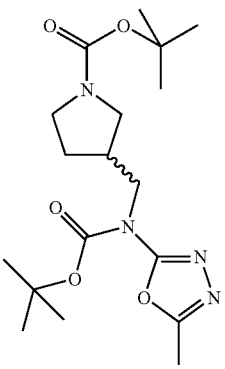

Compound 8b was obtained following the procedure described in the preparation of 8a except substituting 7a for 7b. The resulting crude product was purified by flash chromatography on silica gel, eluting with cyclohexane-ethyl acetate (9:1 to 1:1) to afford 8b as sticky oil (1.7 g, contaminated with Mitsunobu reagents).

Step C: Preparation of 9b

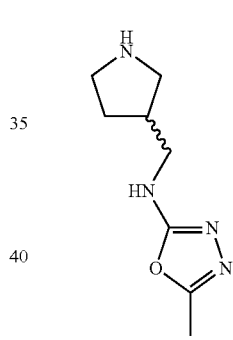

Utilizing the procedure described in the preparation of 4a-4b except substituting 3a-3b for 8b, the title compound was obtained as a colorless oil (180 mg, 21%).
MS (ESI$^+$) (+0.1% HCOOH): 183.27 [C$_8$H$_{14}$N$_4$+H]$^+$ (m/z)

Step D: 8-Fluoro-3-methyl-9-{3-[(5-methyl-[1,3,4] oxadiazol-2-ylamino)-methyl]-pyrrolidin-1-yl}-6-oxo-2,3-dihydro-6H-1-oxa-3,3a-diaza-phenalene-5-carboxylic acid (10b)

Utilizing the procedure for the preparation of 5b, 10b was obtained with TNOC (140 mg, 0.49 mmol, 1.0 eq.) and 9b (180 mg, 0.98 mmol, 2.0 eq.). An analytical sample was obtained by preparative TLC purification eluting with dichloromethane—methanol (gradient from 2.5% to 5% of methanol) to afford the title compound as a yellow solid (76 mg, 34%).

HPLC (gradient 5% to 80% ACN in H$_2$O): >95%
MS (ESI$^+$) (+0.1% HCOOH): 446.9 [C$_{20}$H$_{21}$FN$_6$O$_5$+H]$^+$ (m/z)
mp=240° C.

EXAMPLE 6

8-Fluoro-9-(3-{[furan-2-carbonyl)-amino]methyl}-pyrrolidin-1-yl)-3-methyl-6-oxo-2,3-dihydro-6H-1-oxa-3,3a-diaza-phenalene-5-carboxylic acid (13)

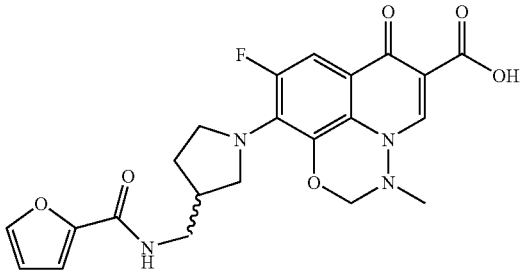

Step A: Preparation of 11

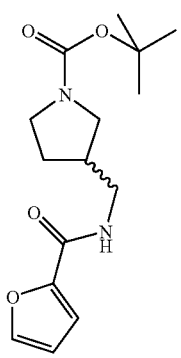

To a 0° C. solution of furan-2-carboxylic acid (1.1 g, 9.81 mmol, 1.3 eq.) in dry DMF (20 mL) were added EDC (1.88 g, 9.81 mmol, 1.3 eq.) and HOBt (1.32 g, 9.81 mmol, 1.3 eq.). The mixture was stirred at room temperature for 20 minutes and 1 (1.1 g, 9.81 mmol, 1.0 eq.) was added. The reaction was stirred at room temperature for 16 hours. The mixture was diluted with ethyl acetate and washed first with water and then with a saturated aqueous $NaHCO_3$ solution, the organic extracts were dried over anhydrous magnesium sulphate and were evaporated under reduced pressure. The resulting crude product was purified by flash chromatography on silica gel, eluting with cyclohexane-ethyl acetate (8:2 to 1:1) to afford 11 (1.8 g, 81%) as a colorless gum.

Step B: Preparation of 12

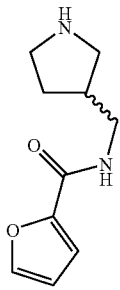

Utilizing the procedure described in preparation of 4a-4b except substituting 3a-3b for 11, the title compound was obtained as a colorless oil (1.0 g, 85%).

MS (ESI$^+$) (+0.1% HCOOH): 195.19 $[C_{10}H_{14}N_2O_2+H]^+$ (m/z)

Step C: 8-Fluoro-9-(3-{[furan-2-carbonyl)-amino]methyl}-pyrrolidin-1-yl)-3-methyl-6-oxo-2,3-dihydro-6H-1-oxa-3,3a-diaza-phenalene-5-carboxylic acid (13)

Utilizing the procedure for the preparation of 5a, 13 was obtained from TNOC (520 mg, 1.84 mmol, 1.0 eq.) and 12 (1.0 g, 5.55 mmol, 3.0 eq.). The mixture was evaporated and co-evaporated with toluene, sonicated with methanol, refluxed and filtrated to afford the title compound as a yellow solid (645 mg, 78%).

HPLC (gradient 5% to 80% ACN in $H_2O$): >99%

MS (ESI$^+$) (+0.1% HCOOH): 457.1 $[C_{22}H_{21}FN_4O_6+H]^+$ (m/z)

mp=278-280° C.

EXAMPLE 7

8-fluoro-3-methyl-6-oxo-9-[3-pyrazin-2-ylamino)-pyrrolidin-1-yl]-2,3-dihydro-6-H-1-oxa-3,3a-diaza-phenalene-5-carboxylic acid (17)

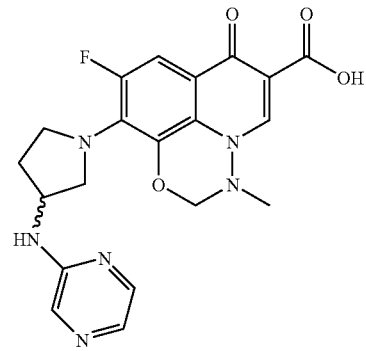

Step A: Preparation of 15

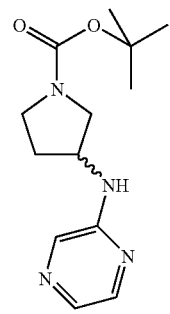

Utilizing the procedure described in preparation of 3a-3b except substituting 3-aminomethyl-pyrrolidine-1-carboxylic acid tert-butyl ester for 3-amino-pyrrolidine-1-carboxylic acid tert-butyl ester 14 {Alegria, 2004 #20}, the title compound was obtained as a colorless oil (800 mg, 69%).

Step B: Preparation of 16

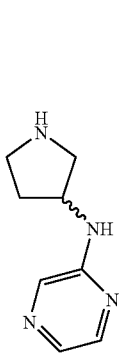

Utilizing the procedure described in preparation of 4c except substituting 3c for 15; the residue was purified by flash chromatography on silica gel, eluting with dichloromethane—7N NH$_3$ in methanol (gradient from 5% to 20% of 7N NH$_3$ in methanol) to afford the title compound was obtained as a colorless oil (500 mg, quantitative).

MS (ESI$^+$) (+0.1% HCOOH): 165.18 [C$_8$H$_{12}$N$_4$+H]$^+$ (m/z)

Step C: 8-fluoro-3-methyl-6-oxo-9-[3-pyrazin-2-ylamino)-pyrrolidin-1-yl]-2,3-dihydro-6-H-1-oxa-3, 3a-diaza-phenalene-5-carboxylic acid (17)

Utilizing the procedure described in preparation of 5c except substituting 4c for 16 (500 mg, 3.05 mmol, 3.0 eq.), the title compound was obtained as a yellow solid (175 mg, 41%).

HPLC (gradient 5% to 80% ACN in H$_2$O): >99%
MS (ESI$^+$) (+0.1% HCOOH): 427.15 [C$_{20}$H$_{19}$FN$_6$O$_4$+H]$^+$ (m/z)
mp=269° C., dec.

EXAMPLE 8

8-fluoro-3-methyl-6-oxo-9-[3-pyridin-2-ylamino)-pyrrolidin-1-yl]-2,3-dihydro-6H-1-oxa-3,3a-diaza-phenalene-5-carboxylic acid (22)

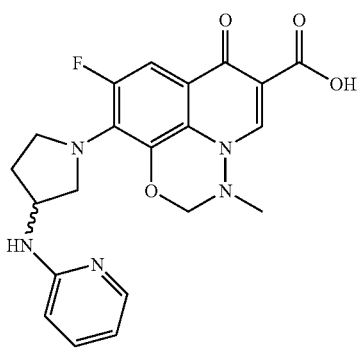

Step A: Preparation of 20

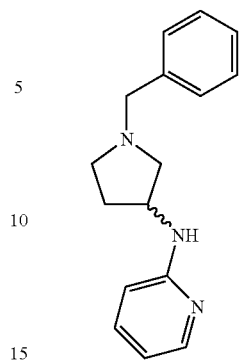

To a −78° C. solution of 2-fluoropyridine (1.0 mL, 11.29 mmol, 1.0 eq.) and 1-benzyl-pyrrolidin-3-ylamine (2.0 g, 11.29 mmol, 1.0 eq.) in dry THF (5 mL) was added LiHMDS 1M in THF (23 mL, 22.57 mmol, 2.0 eq.). The reaction was stirred at room temperature for 1 hour and then at 90° C. overnight. The reaction was diluted with water and extracted with ethyl acetate; the organic extracts were dried over anhydrous magnesium sulphate and were evaporated under reduced pressure. The resulting crude product was purified by flash chromatography on silica gel, eluting with 100% ethyl acetate to afford 20 (2.08 g, 72%) as a colorless gum.

MS (ESI$^+$) (+0.1% HCOOH): 254.06 [C$_{16}$H$_{19}$N$_3$+H]$^+$ (m/z)

Step B: Preparation of 21

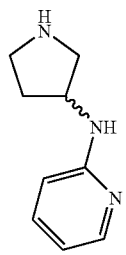

To a solution of 20 (2.08 g, 8.22 mmol) in methanol (25 mL) were added 2 drops of trifluoroacetic acid and Pd/C (500 mg). The mixture was submitted to hydrogenation at atmospheric pressure and at 40° C. for 36 hours. The reaction was filtered over Celite® and evaporated under reduced pressure. The residue was purified by flash chromatography on silica gel, eluting with dichloromethane—methanol (gradient from 5% to 10% methanol) then dichloromethane—7N NH$_3$ in methanol (gradient from 10% to 20% of 7N NH$_3$ in methanol). The title compound was obtained as an orange oil (1.3 g, 97%).

MS (ESI$^+$) (+0.1% HCOOH): 164.16 [C$_9$H$_{13}$N$_3$+H]$^+$ (m/z)

Step C: 8-fluoro-3-methyl-6-oxo-9-[3-pyridin-2-ylamino)-pyrrolidin-1-yl]-2,3-dihydro-6H-1-oxa-3, 3a-diaza-phenalene-5-carboxylic acid (22)

Utilizing the procedure described in the preparation of 5a except substituting 4a for 21 (1.3 g, 7.96 mmol, 3.2 eq.), the title compound was obtained as a yellow solid (900 mg, 85%).

HPLC (gradient 20% to 80% ACN in H$_2$O): >99%
MS (ESI$^+$) (+0.1% HCOOH): 426.1 [C$_{21}$H$_{20}$FN$_5$O$_4$+H]$^+$ (m/z)
mp=278-280° C.

EXAMPLE 9

8-Fluoro-3-methyl-9-[3-(5-methyl-[1,3,4]oxadiazol-2-ylamino)-pyrrolidin-1-yl-6-oxo-2,3-dihydro-6H-1-oxa-3,3a-diaza-phenalene-5-carboxylic acid (24d)

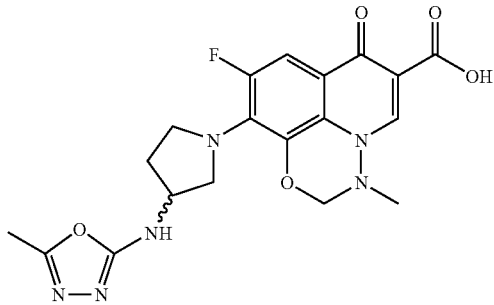

Step A: Preparation of 24b

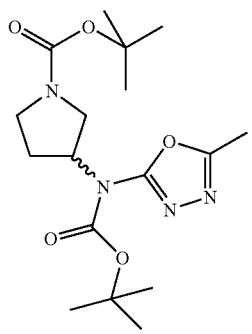

Utilizing the procedure described in preparation of 8b except substituting 6 for 3-hydroxy-pyrrolidine-1-carboxylic acid tert-butyl ester (1.1 g, 5.87 mmol) 23{Hansen, 2003 #1}. The resulting crude product was purified by flash chromatography on silica gel, eluting with cyclohexane-ethyl acetate (9:1 to 1:1) to afford 24b as sticky oil (2.5 g, contaminated with Mitsunobu reagents).

Step B: Preparation of 24c

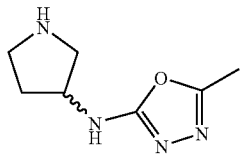

Utilizing the procedure described in preparation of 4a-4b except substituting 3a-3b for 24b, the title compound was obtained as a colorless oil (200 mg, 20%).

MS (ESI$^+$) (+0.1% HCOOH): 169.24 [C$_7$H$_{12}$N$_4$O+H]$^+$ (m/z)

Step C: 8-Fluoro-3-methyl-9-[3-(5-methyl-[1,3,4]oxadiazol-2-ylamino)-pyrrolidin-1-yl-6-oxo-2,3-dihydro-6H-1-oxa-3,3a-diaza-phenalene-5-carboxylic acid (24d)

Utilizing the procedure for the preparation of 10b except substituting 9b for 24c (200 mg, 1.19 mmol, 2.0 eq.). The precipitate was filtered and washed with water then diethyl ether to afford the title compound as a yellow solid (62 mg, 25%).

HPLC (gradient 5% to 95% ACN in H$_2$O): >95%

MS (ESI$^+$) (+0.1% HCOOH): 431.2 [C$_{19}$H$_{19}$FN$_6$O$_5$+H]$^+$ (m/z)

mp=285° C.

EXAMPLE 10

8-Fluoro-3-methyl-6-oxo-9-[3-([1,3,4]thiadiazol-2-ylamino)-pyrrolidin-1-yl]-2,3-dihydro-6H1-oxa-3,3a-diaza-phenalene-5-carboxylic acid (25d)

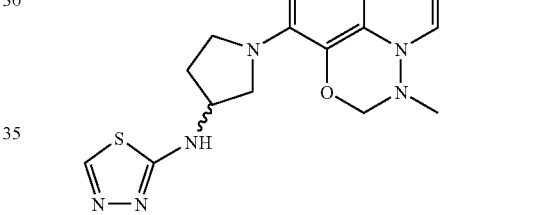

Step A: Preparation of 25b

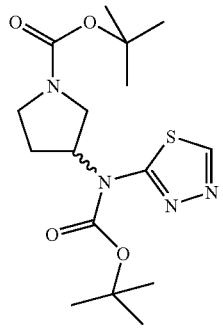

Utilizing the procedure described in preparation of 8a except substituting 6 for 3-hydroxy-pyrrolidine-1-carboxylic acid tert-butyl ester (1.88 g, 10.0 mmol, 1.0 eq.) 23 {Hansen, 2003 #1} and 7a for 25a{Gravestock, 2003 #2}(1.62 g, 8.06 mmol, 0.8 eq.). The resulting crude product was purified by flash chromatography on silica gel, eluting with cyclohexane-ethyl acetate (9:1 to 8:2) to afford 25b as sticky oil (1.63 g, 54%).

Step B: Preparation of 25c

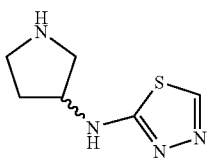

Utilizing the procedure described in preparation of 4a-4b except substituting 3a-3b for 25b (2.7 g, 7.29 mmol). The residue was purified by flash chromatography on silica gel, eluting with dichloromethane—methanol (gradient from 5% to 10% methanol) then dichloromethane—7N NH$_3$ in methanol (gradient from 10% to 40% of 7N NH$_3$ in methanol). The title compound was obtained as a colorless oil (951 mg, 76%).

Step C: 8-Fluoro-3-methyl-6-oxo-9-[3-([1,3,4]thiadiazol-2-ylamino)-pyrrolidin-1-yl]-2,3-dihydro-6H-1-oxa-3,3a-diaza-phenalene-5-carboxylic acid (25d)

Utilizing the procedure for the preparation of 5a except substituting 4a for 25c (950 mg, 5.59 mmol, 3.0 eq.). The precipitate was filtered and washed with water; the residue was triturated in hot methanol and gave after filtration the title compound as a yellow solid (688 mg, 73%).

HPLC (gradient 5% to 95% ACN in H$_2$O): >90%

MS (ESI$^+$) (+0.1% HCOOH): 433.1 [C$_{18}$H$_{17}$FN$_6$O$_4$S+H]$^+$ (m/z)

mp=320° C., dec.

EXAMPLE 11

8-Fluoro-3-methyl-6-oxo-9-[3-([1,2,4]thiadiazol-5-ylamino)-pyrrolidin-1-yl]-2,3-dihydro-6H-1-oxa-3,3a-diaza-phenalene-5-carboxylic acid (26d).

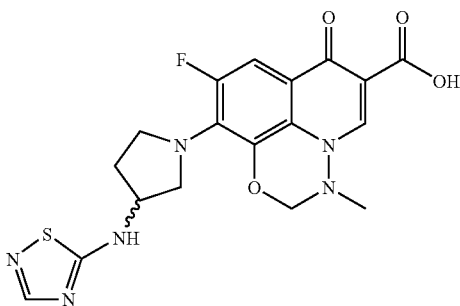

Step A: Preparation of 26b

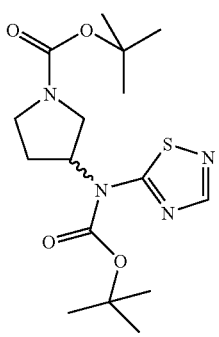

Utilizing the procedure described in preparation of 8a except substituting 6 for 3-hydroxy-pyrrolidine-1-carboxylic acid tert-butyl ester (1.2 g, 6.41 mmol, 1.0 eq.) 23 {Hansen, 2003 #1} and 7a for 26a {Gravestock, 2003 #2}(1.03 g, 5.13 mmol, 0.8 eq.). The resulting crude product was purified by flash chromatography on silica gel, eluting with cyclohexane-ethyl acetate (9:1 to 8:2) to afford 26b as sticky oil (2.03 g, 85%).

Step B: Preparation of 26c

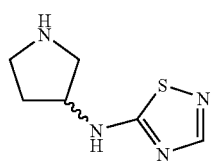

Utilizing the procedure described in preparation of 4a-4b except substituting 3a-3b for 26b (2.0 g, 5.40 mmol). The residue was purified by flash chromatography on silica gel, eluting with dichloromethane—methanol (gradient from 5% to 20% methanol) then dichloromethane—7N NH$_3$ in methanol (gradient from 5% to 40% of 7N NH$_3$ in methanol). The title compound was obtained as a colorless oil (1.0 g, quantitative).

Step C: 8-Fluoro-3-methyl-6-oxo-9-[3-([1,2,4]thiadiazol-5-ylamino)-pyrrolidin-1-yl]-2,3-dihydro-6H-1-oxa-3,3a-diaza-phenalene-5-carboxylic acid (26d)

Utilizing the procedure for the preparation of 25d except substituting 25c for 26c (1.0 g, 5.88 mmol, 2.5 eq.). The residue was triturated with hot methanol and filtrated. The title compound was obtained as a yellow solid (614 mg, 61%).

HPLC (gradient 5% to 95%% ACN in H$_2$O): >95%

MS (ESI$^+$) (+0.1% HCOOH): 433.2 [C$_{18}$H$_{17}$FN$_6$O$_4$S+H]$^+$ (m/z)

mp=285° C., dec.

EXAMPLE 12

9-[3-(4,5-Dimethyl-thiazol-2-ylamino)-pyrrolidin-1-yl]-8-fluoro-3-methyl-6-oxo-2,3-dihydro-6H-1-oxa-3,3a-diaza-phenalene-5-carboxylic acid (27d)

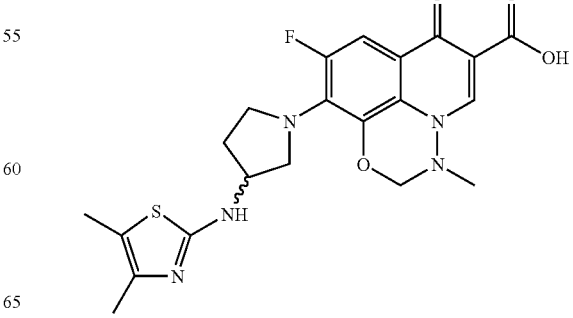

Step A: Preparation of 27a

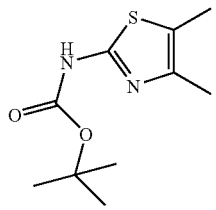

Utilizing the procedure for the preparation of 7a except substituting 2-aminothiazole for 2-amino-4,5-dimethylthiazole hydrochloride (2.5 g, 15.2 mmol, 1.0 eq.). The title compound was obtained as a white solid (1.07g, 31%).

Step B: Preparation of 27b

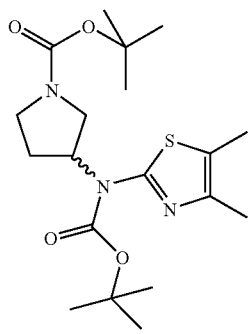

Utilizing the procedure described in preparation of 8a except substituting 6 for 3-hydroxy-pyrrolidine-1-carboxylic acid tert-butyl ester (1.1 g, 5.83 mmol, 1.0 eq.) 23{Hansen, 2003 #1} and 7a for 27a (1.07 g, 4.67 mmol, 0.8 eq.). The resulting crude product was purified by flash chromatography on silica gel, eluting with cyclohexane-ethyl acetate (1:0 to 8:2) to afford 27b as a colorless oil (1.45 g, 78%).

Step C: Preparation of 27c

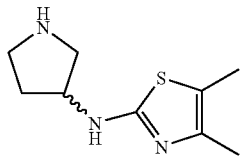

Utilizing the procedure described in preparation of 4c except substituting 3c for 27b (1.45 g, 3.65 mmol) with 15 mL of 4N HCl in dioxane. The residue was purified by flash chromatography on silica gel, eluting with dichloromethane—7N $NH_3$ in methanol (gradient from 5% to 20% of 7N $NH_3$ in methanol). The title compound was obtained as a colorless oil (940 mg, quantitative).

MS (ESI$^+$) (+0.1% HCOOH): 198.21 [$C_9H_{15}N_3S$+H]$^+$ (m/z)

Step D: 9-[3-(4,5-Dimethyl-thiazol-2-ylamino)-pyrrolidin-1-yl]-8-fluoro-3-methyl-6-oxo-2,3-dihydro-6H-1-oxa-3,3a-diaza-phenalene-5-carboxylic acid (27d)

Utilizing the procedure described in preparation of 5c except substituting 4c for 27c (940 mg, 4.76 mmol, 4.0 eq.). The reaction was evaporated under reduced pressure; the residue was triturated with water and filtrated. The resulting solid was triturated and filtrated first with methanol, then with dichloromethane, and finally with methanol; the title compound was obtained as a yellow solid (143 mg, 26%).

HPLC (gradient 5% to 95% ACN in $H_2O$): >95%

MS (ESI$^+$) (+0.1% HCOOH): 460.4 [$C_{21}H_{22}FN_5O_4S$+H]$^+$ (m/z)

mp=266° C., dec.

EXAMPLE 13

8-Fluoro-3-methyl-9-[3-(4-methyl-thiazol-2-ylamino)-pyrrolidin-1-yl]-6-oxo-2,3-dihydro-6H-1-oxa-3,3a-diaza-phenalene-5-carboxylic acid (28d)

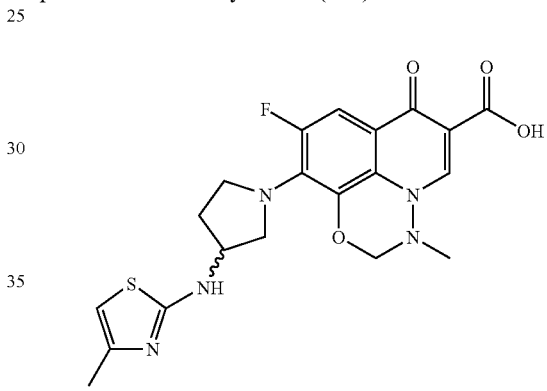

Step A: Preparation of 28b

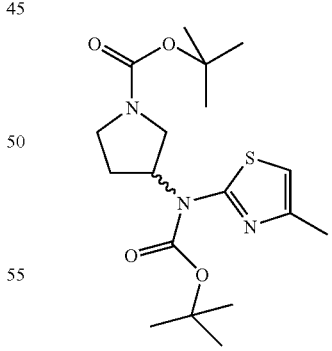

Utilizing the procedure described in the preparation of 8a except substituting 6 for 3-hydroxy-pyrrolidine-1-carboxylic acid tert-butyl ester (1.1 g, 5.83 mmol, 1.0 eq.) 23 {Hansen, 2003 #1} and 7a for 28a {Hadida Ruah, 2007 #3}(1.0 g, 4.67 mmol, 0.8 eq.). The resulting crude product was purified by flash chromatography on silica gel, eluting with cyclohexane-ethyl acetate (1:0 to 8:2) to afford 28b as a colorless oil (1.45 g, 87%).

Step B: Preparation of 28c

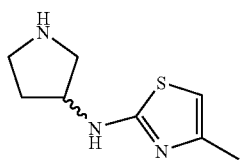

Utilizing the procedure described in the preparation of 4c except substituting 3c for 28b (1.55 g, 4.04 mmol) with 7 mL of 4N HCl in dioxane. The residue was purified by flash chromatography on silica gel, eluting with dichloromethane—7N $NH_3$ in methanol (gradient from 5% to 10% of 7N $NH_3$ in methanol). The title compound was obtained as a white solid (1.0 g, quantitative).

MS (ESI$^+$) (+0.1% HCOOH): 184.15 $[C_8H_{13}N_3S+H]^+$ (m/z)

Step C: 8-Fluoro-3-methyl-9-[3-(4-methyl-thiazol-2-ylamino)-pyrrolidin-1-yl]-6-oxo-2,3-dihydro-6H-1-oxa-3,3a-diaza-phenalene-5-carboxylic acid (28d)

Utilizing the procedure described in the preparation of 5c except substituting 4c for 28c (1.0 g, 5.46 mmol, 4.0 eq.). The reaction was evaporated under reduced pressure; the residue was triturated with water and filtrated. An analytical sample was obtained by preparative TLC purification eluting with dichloromethane—methanol (gradient from 2.5% to 5% of methanol) to afford the title compound as a yellow solid (100 mg, 33%).

HPLC (gradient 5% to 95% ACN in $H_2O$): >99%

MS (ESI$^+$) (+0.1% HCOOH): 446.2 $[C_{20}H_{20}FN_5O_4S+H]^+$ (m/z)

mp=260° C., dec.

EXAMPLE 14

8-Fluoro-3-methyl-9-[3-(5-methyl-thiazol-2-ylamino)-pyrrolidin-1-yl]-6-oxo-2,3-dihydro-6H-1-oxa-3,3a-diaza-phenalene-5-carboxylic acid (29d)

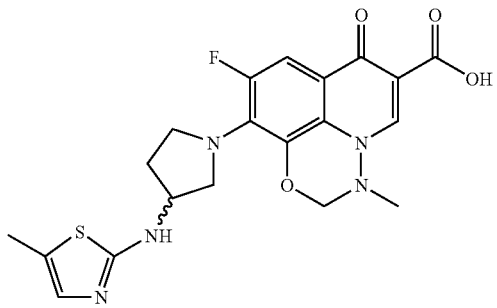

Step A: Preparation of 29a

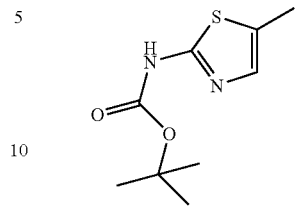

Utilizing the procedure for the preparation of 7a except substituting 2-aminothiazole for 2-amino-5-methylthiazole (2.0 g, 17.5 mmol, 1.0 eq.), the title compound was obtained as a white solid (1.07 g, 45%).

Step B: Preparation of 29b

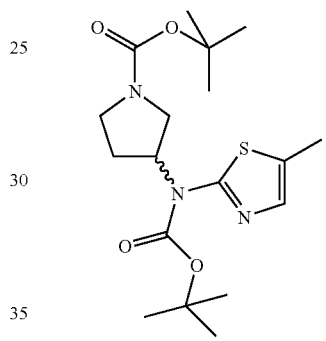

Utilizing the procedure described in the preparation of 8a except substituting 6 for 3-hydroxy-pyrrolidine-1-carboxylic acid tert-butyl ester (1.86 g, 9.92 mmol, 1.0 eq.) 23{Hansen, 2003 #1} and 7a for 29a (1.7 g, 7.93 mmol, 0.8 eq.). The resulting crude product was purified by flash chromatography on silica gel, eluting with cyclohexane-ethyl acetate (1:0 to 1:1) to afford 29b as a yellow oil (2.1 g, 69%).

Step C: Preparation of 29c

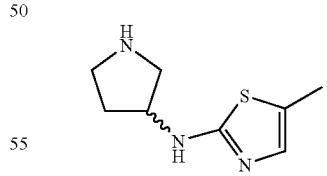

Utilizing the procedure described in the preparation of 4c except substituting 3c for 29b (2.1 g, 5.48 mmol, 1.0 eq.) with 15 mL of 4N HCl in dioxane. The residue was purified by flash chromatography on silica gel, eluting with dichloromethane—7N $NH_3$ in methanol (gradient from 5% to 20% of 7N $NH_3$ in methanol). The title compound was obtained as a white solid (930 mg, 93%).

MS (ESI$^+$) (+0.1% HCOOH): 184.15 $[C_8H_{13}N_3S+H]^+$ (m/z)

Step D: 8-Fluoro-3-methyl-9-[3-(5-methyl-thiazol-2-ylamino)-pyrrolidin-1-yl]-6-oxo-2,3-dihydro-6H-1-oxa-3,3a-diaza-phenalene-5-carboxylic acid (29d)

Utilizing the procedure described in the preparation of 5c except substituting 4c for 29c (930 mg, 5.13 mmol, 4.0 eq.). The reaction was evaporated under reduced pressure; the residue was triturated with water and filtrated. An analytical sample was obtained by preparative TLC purification eluting with dichloromethane—methanol (gradient from 2.5% to 5% of methanol) to afford the title compound as a yellow solid (72 mg, 25%).

HPLC (gradient 5% to 95% ACN in $H_2O$): >95%
MS (ESI$^+$) (+0.1% HCOOH): 446.1 [$C_{20}H_{20}FN_5O_4S$+H]$^+$ (m/z)
mp=265° C., dec.

EXAMPLE 15

8-Fluoro-3-methyl-9-[3-(3-methyl-isothiazol-5-ylamino)-pyrrolidin-1-yl]-6-oxo-2,3-dihydro-6H-1-oxa-3,3a-diaza-phenalene-5-carboxylic acid (30d)

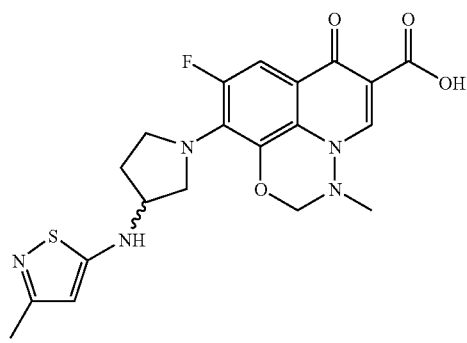

Step A: Preparation of 30b

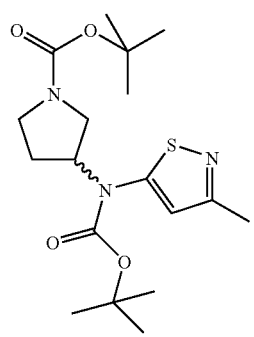

Utilizing the procedure described in the preparation of 8a except substituting 6 for 3-hydroxy-pyrrolidine-1-carboxylic acid tert-butyl ester (1.7 g, 9.08 mmol, 1.0 eq.) 23{Hansen, 2003 #1} and 7a for 30a{Butira, 2004 #4} (1.94 g, 9.08 mmol, 1.0 eq.). The resulting crude product was purified by flash chromatography on silica gel, eluting with cyclohexane-ethyl acetate (9:1 to 7:3) to afford 30b as a yellow oil (2.9 g, 84%).

Step B: Preparation of 30c

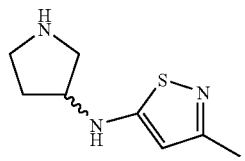

Utilizing the procedure described in the preparation of 4a-4b except substituting 3a-3b for 30b (2.9 g, 7.57 mmol, 1.0 eq.). The residue was purified by flash chromatography on silica gel, eluting with dichloromethane—methanol (gradient from 5% to 10% methanol) then dichloromethane—7N $NH_3$ in methanol (gradient from 10% to 30% of 7N $NH_3$ in methanol). The title compound was obtained as a colorless oil (1.0 g, 72%).

Step B: 8-Fluoro-3-methyl-9-[3-(3-methyl-isothiazol-5-ylamino)-pyrrolidin-1-yl]-6-oxo-2,3-dihydro-6H-1-oxa-3,3a-diaza-phenalene-5-carboxylic acid (30d)

Utilizing the procedure for the preparation of 10b except substituting 9b for 30c (1.0 g, 5.46 mmol, 3.0 eq.). The reaction was evaporated under reduced pressure; the residue was triturated with ethanol and filtrated (251 mg). An analytical sample was obtained by preparative TLC purification eluting with dichloromethane—methanol (gradient from 2.5% to 7.5% of methanol) to afford the title compound as a yellow solid (42 mg, 10%).

HPLC (gradient 5% to 95% ACN in $H_2O$): >95%
MS (ESI$^+$) (+0.1% HCOOH) : 446.26 [$C_{20}H_{20}FN_5O_6S$+H]$^+$ (m/z)
Mp=265° C.

EXAMPLE 16

8-Fluoro-3-methyl-9-[3-(3-methyl-isoxazol-5-ylamino)-pyrrolidin-1-yl]-6-oxo-2,3-dihydro-6H-1-oxa-3,3a-diaza-phenalene-5-carboxylic acid (31d)

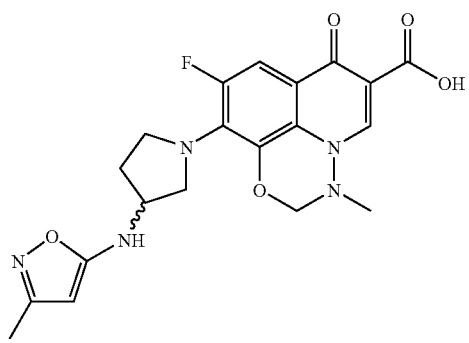

Step A: Preparation of 31b

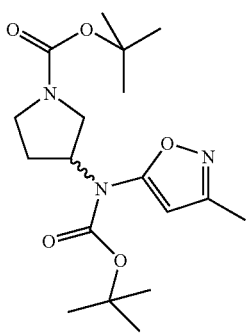

Utilizing the procedure described in the preparation of 8a except substituting 6 for 3-hydroxy-pyrrolidine-1-carboxylic acid tert-butyl ester (0.47 g, 2.52 mmol, 1.0 eq.) 23 {Hansen, 2003 #1} and 7a for 31a{Gravestock, 2003 #2} (0.4 g, 2.02 mmol, 0.8 eq.). The resulting crude product was purified by flash chromatography on silica gel, eluting with cyclohexane-ethyl acetate (95:5 to 6:4) to afford 31b as a white solid (0.5 g, 67%).

Step B: Preparation of 31c

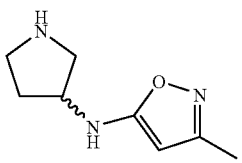

Utilizing the procedure described in the preparation of 4c except substituting 3c for 31b (0.6 g, 1.63 mmol, 1.0 eq.) with 10 mL of 4N HCl in dioxane. The residue was purified by flash chromatography on silica gel, eluting with dichloromethane—7N $NH_3$ in methanol (gradient from 5% to 20% of 7N $NH_3$ in methanol). The title compound was obtained as a white solid (230 mg, 84%).

MS (ESI$^+$) (+0.1% HCOOH): 168.43 $[C_8H_{13}N_3O+H]^+$ (m/z)

Step C: 8-Fluoro-3-methyl-9-[3-(3-methyl-isoxazol-5-ylamino)-pyrrolidin-1-yl]-6-oxo-2,3-dihydro-6H-1-oxa-3,3a-diaza-phenalene-5-carboxylic acid (31d)

Utilizing the procedure described in the preparation of 5c except substituting 4c for 31 c (230 mg, 1.38 mmol, 2.0 eq.). The reaction was evaporated under reduced pressure; the residue was triturated with water and filtrated. An analytical sample was obtained by preparative TLC purification eluting with dichloromethane—methanol (gradient from 2.5% to 5% of methanol) to afford the title compound as a yellow solid (50 mg, 17%).

HPLC (gradient 5% to 95% ACN in $H_2O$): >95%

MS (ESI$^+$) (+0.1% HCOOH): 430.2 $[C_{20}H_{20}FN_5O_5+H]^+$ (m/z)

mp=244° C., dec.

EXAMPLE 17

8-Fluoro-3-methyl-9-[3-(5-methyl-isoxazol-3-ylamino)-pyrrolidin-1-yl]-6-oxo-2,3-dihydro-6H-1-oxa-3,3a-diaza-phenalene-5-carboxylic acid (32d)

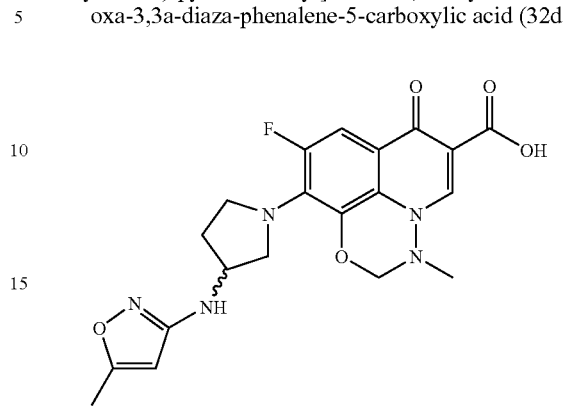

Step A: Preparation of 32b

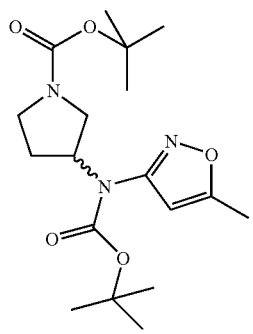

Utilizing the procedure described in the preparation of 8a except substituting 6 for 3-hydroxy-pyrrolidine-1-carboxylic acid tert-butyl ester (4.25 g, 22.7 mmol, 1.0 eq.) 23 {Hansen, 2003 #1} and 7a for 32a {almansa Rosales, 2006 #5} (3.6 g, 18.2 mmol, 0.8 eq.). The resulting cru product was purified by flash chromatography on silica gel, eluting with cyclohexane-ethyl acetate (1:0 to 8:2) to afford 32b as a colorless oil (1.8 g, 27%).

Step B: Preparation of 32c

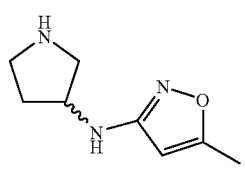

Utilizing the procedure described in the preparation of 4c except substituting 3c for 32b (1.8 g, 4.9 mmol, 1.0 eq.) with 10 mL of 4N HCl in dioxane. The residue was purified by flash chromatography on silica gel, eluting with dichloromethane—7N $NH_3$ in methanol (gradient from 5% to 20% of 7N $NH_3$ in methanol). The title compound was obtained as a white solid (1.0 g, quantitative).

MS (ESI$^+$) (+0.1% HCOOH): 168.22 $[C_8H_{13}N_3O+H]^+$ (m/z)

Step C: 8-Fluoro-3-methyl-9-[3-(5-methyl-isoxazol-3-ylamino)-pyrrolidin-1-yl]-6-oxo-2,3-dihydro-6H-1-oxa-3,3a-diaza-phenalene-5-carboxylic acid (32d)

Utilizing the procedure described in the preparation of 5c except substituting 4c for 32c (1.0 g, 5.98 mmol, 4.0 eq.). The reaction was evaporated under reduced pressure; the residue was triturated first with ethanol and filtrated and secondly with methanol to afford the title compound as a yellow solid (532 mg, 83%).

HPLC (gradient 5% to 95% ACN in $H_2O$): >99%
MS (ESI$^+$) (+0.1% HCOOH): 430.25 $[C_{20}H_{20}FN_5O_5+H]^+$ (m/z) mp=263° C., dec.

EXAMPLE 18

8-Fluoro-3-methyl-6-oxo-9-[(S)-3-(thiazol-2-ylamino)-pyrrolidin-1-yl]-2,3dihydro-6H-1-oxa-3,3a-diaza-phenalene-5-carboxylic acid (36a)

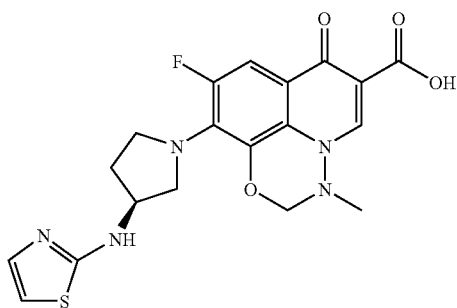

Step A: Preparation of 34a

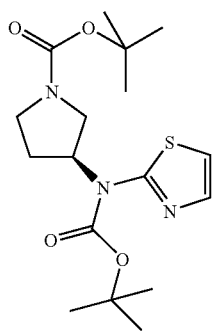

Utilizing the procedure described in the preparation of 8a except substituting 6 for (R)-3-hydroxy-pyrrolidine-1-carboxylic acid tert-butyl ester 33a (1.0 g, 5.34 mmol, 1.1 eq.) and 7a (1.17 g, 5.87 mmol, 1.0 eq.). The resulting crude product was purified by flash chromatography on silica gel, eluting with cyclohexane-ethyl acetate (95:5 to 85:15) to afford 34a as a colorless oil (1.8 g, 97%).

Step B: Preparation of 35a

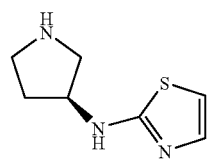

Utilizing the procedure described in preparation of 4c except substituting 3c for 34a (1.8 g, 4.87 mmol, 1.0 eq.) and dichloromethane for ethyl acetate with 20 mL of 4N HCl in dioxane. The reaction was stirred one hour at 60° C. and evaporated under reduced pressure. The residue was purified by flash chromatography on silica gel, eluting with dichloromethane—methanol (gradient from 5% to 10% methanol) then dichloromethane—7N $NH_3$ in methanol (gradient from 20% to 50% of 7N $NH_3$ in methanol). The title compound was obtained as a white solid (780 mg, 94%).

MS (ESI$^+$) (+0.1% HCOOH): 170.15 $[C_7H_{11}N_3S+H]^+$ (m/z)

Step C: 8-Fluoro-3-methyl-6-oxo-9-[(S)-3-(thiazol-2-ylamino)-pyrrolidin-1-yl]-2,3 dihydro-6H-1-oxa-3,3a-diaza-phenalene-5-carboxylic acid (36a)

Utilizing the procedure for the preparation of 10b except substituting 9b for 35a (780 mg, 4.61 mmol, 3.0 eq.). The reaction was evaporated under reduced pressure; the residue was triturated with methanol and filtrated (462 mg). An analytical sample was obtained by preparative TLC purification eluting with dichloromethane—methanol (gradient from 2.5% to 5% of methanol) to afford the title compound as a yellow solid (30 mg, 17%).

HPLC (gradient 5% to 80% ACN in $H_2O$): >99%
MS (ESI$^+$) (+0.1% HCOOH): 432.18 $[C_{19}H_{18}FN_5O_4S+H]^+$ (m/z)
mp=275° C.° C.

EXAMPLE 19

8-Fluoro-3-methyl-6-oxo-9-[(R)-3-(thiazol-2-ylamino)-pyrrolidin-1-yl]-2,3-dihydro-6H-1-oxa-3,3a-diaza-phenalene-5-carboxylic acid (36b)

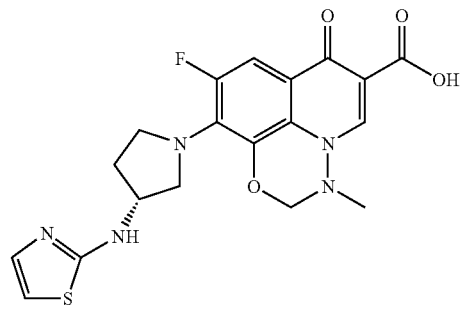

Step A: Preparation of 34b

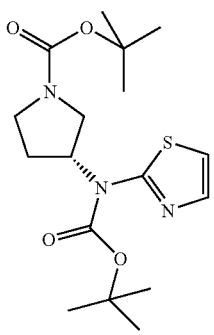

Utilizing the procedure described in the preparation of 8a except substituting 6 for (S)-3-hydroxy-pyrrolidine-1-carboxylic acid tert-butyl ester 33b (1.0 g, 5.34 mmol, 1.0 eq.) and 7a (1.07 g, 5.34 mmol, 1.0 eq.). The resulting crude product was purified by flash chromatography on silica gel, eluting with cyclohexane-ethyl acetate (1:0 to 8:2) to afford 34b as an colorless oil (1.8 g, quantitative).

$^1$H NMR (CDCl$_3$): δ 7.60 (d, 1H, J=3.7), 7.02 (d, 1H, J=3.6), 5.73-5.62 (m, 1H), 3.40-3.31 (m, 1H), 3.74-3.67 (m, 3H), 2.52-2.39 (m, 1H), 2.22-2.13 (m, 1H), 1.57 (s, 9H), 1.46 (s, 9H).

Step B: Preparation of 35b

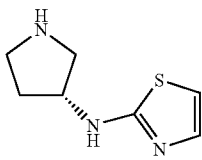

Utilizing the procedure described in the preparation of 4c except substituting 3c for 34b (1.8 g, 4.87 mmol) with 15 mL of 4N HCl in dioxane. The residue was purified by flash chromatography on silica gel, eluting with dichloromethane—7N NH$_3$ in methanol (gradient from 5% to 20% of 7N NH$_3$ in methanol). The title compound was obtained as a white solid (900 mg, quantitative).

MS (ESI$^+$) (+0.1% HCOOH): 170.17 [C$_7$H$_{11}$N$_3$S+H]$^+$ (m/z)

Step C: 8-Fluoro-3-methyl-6-oxo-9-[(R)-3-(thiazol-2-ylamino)-pyrrolidin-1-yl]-2,3-dihydro-6H-1-oxa-3,3a-diaza-phenalene-5-carboxylic acid (36b)

Utilizing the procedure described in the preparation of 5c except substituting 4c for 35b (900 mg, 5.32 mmol, 4.0 eq.). The reaction was evaporated under reduced pressure; the residue was triturated with water and filtrated. The resulting residue was triturated with methanol and filtrated to afford the title compound as a yellow solid (440 mg, 77%)

HPLC (gradient 5% to 80% ACN in H$_2$O): >95%

MS (ESI$^+$) (+0.1% HCOOH): 432.12 [C$_{19}$H$_{18}$FN$_5$O$_4$S+H]$^+$ (m/z)

mp=245-250° C.° C., dec.

EXAMPLE 20

9-[3-(4,5-Dihydro-thiazol-2-ylamino)-pyrrolidin-1-yl]-8-fluoro-3-methyl--oxo-2,3-dihydro-6H-1-oxa-3,3a-diaza-phenalene-5-carboxylic acid (40)

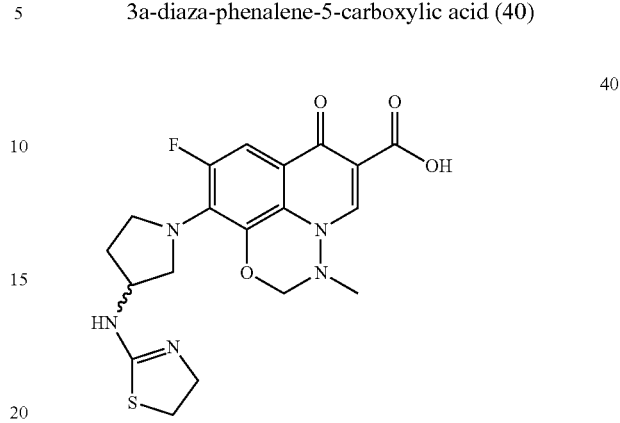

Step A: Preparation of 37

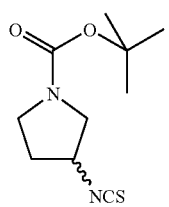

To a −78° C. solution of 14 (1.5 g, 8.05 mmol, 1.0 eq.) in dry dichloromethane (40 mL), thiocarbonylimidazole (1.81 g, 9.66 mmol, 1.2 eq.) was added. The mixture was then allowed to reach slowly room temperature overnight. The reaction mixture was washed with water, the organic extracts were dried over anhydrous sodium sulfate and evaporated under reduced pressure. The residue was purified by flash chromatography on silica gel, eluting with cyclohexane-ethyl acetate (9:1 to 7:3) to afford 37 as a colorless oil (1.29 g, 70%).

Step B: Preparation of 38

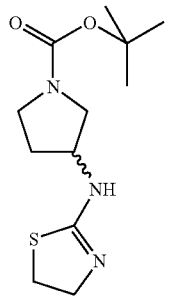

To a solution of 37 (1.87 g, 8.19 mmol, 1.0 q.) in dry THF (30 mL) were added triethylamine (2.3 mL, 16.38 mmol, 2.0 eq.) and 2-chloroethylamine hydrochloride (1.14 g, 9.33 mmol, 1.14 eq.). After 18 hours at room temperature the reaction mixture was refluxed for one day. After cooling the salts were filtrated and the filtrate was evaporated under reduced pressure. The residue was purified by flash chromatography on silica gel, eluting with 100% ethyl acetate then with dichloromethane—methanol (gradient from 5% to 15% of methanol) to afford 38 as an colorless oil (1.9 g, 85%).

Step C: Preparation of 39

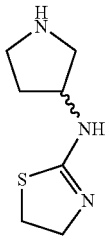

Utilizing the procedure described in preparation of 4a-4b except substituting 3a-3b for 38 (1.9 g, 7.00 mmol). The residue was purified by flash chromatography on silica gel, eluting with dichloromethane—methanol (gradient from 5% to 10% methanol) then dichloromethane—7N NH$_3$ in methanol (gradient from 10% to 30% of 7N NH$_3$ in methanol). The title compound was obtained as a colorless oil (0.5 g, 42%).

Step D: 9-[3-(4,5-Dihydro-thiazol-2-ylamino)-pyrrolidin-1-yl]-8-fluoro-3-methyl-6-oxo-2,3-dihydro-6H-1-oxa-3,3a-diaza-phenalene-5-carboxylic acid (40)

Utilizing the procedure for the preparation of 10b except substituting 9b for 39 (500 mg, 2.92 mmol, 2.7 eq.). The reaction was filtrated (125 mg). An analytical sample was obtained by preparative TLC purification eluting with dichloromethane—methanol (gradient from 2.5% to 5% of methanol) to afford the title compound as a light yellow solid (30 mg, 6.5%).

HPLC (gradient 5% to 95% ACN in H$_2$O): >99%
MS (ESI$^+$) (+0.1% HCOOH): 434.0 [C$_{19}$H$_{20}$FN$_5$O$_4$S+H]$^+$ (m/z)
mp=265-267° C.° C., dec.

EXAMPLE 21

8-fluoro-3-methyl-6-oxo-9-[3-([1,2,4]triazolo-1-yl)-pyrrolidine]-2,3-dihydro-6H-1-oxa-3,3a-diaza-phenalene-5-carboxylic acid and 8-fluoro-3-methyl-6-oxo-9-[3-([1,3,4]triazolo-1-yl)-pyrrolidine-2,3-dihydro-6H-1-oxa-3,3a-diaza-phenalene-5-carboxylic acid (44a-44b)

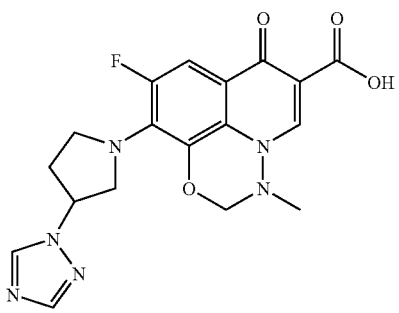

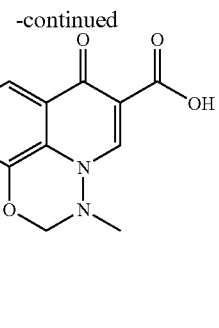

Step A: Preparation of 42a-42b

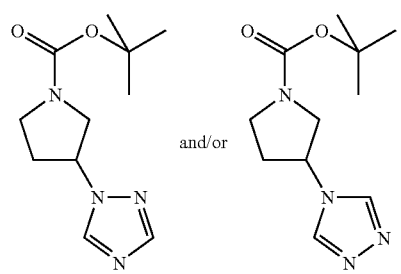

Prepared according to the procedure reported in US2003/0225107 except substituting 5(R)-3-[4-(1-cyanocyclopropan-1-yl]-5-hydroxy methyloxazolidin-2-one for 23 (1.6 g, 8.54 mmol, 1.0 eq.), tetramethylazodicarboxamide for diethylazodicarboxylate, butylphosphine for triphenylphosphine and benzene for tetrahydrofurane. The resulting crude product was purified by flash chromatography on silica gel, eluting with cyclohexane-ethyl acetate (7:3 to 0:1) to afford 42a-42b as a colorless oil (845 mg, 42%).

Step B: Preparation of 43a-43b

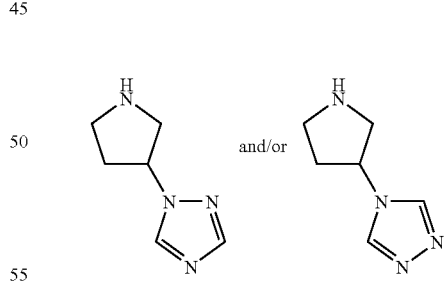

Utilizing the procedure described in PREPARATION of 4a-4b except substituting 3a-3b for 42a-42b (950 mg, 3.98 mmol). The residue was purified by flash chromatography on silica gel, eluting with dichloromethane—methanol (gradient from 5% to 10% methanol) then dichloromethane—7N NH$_3$ in methanol (gradient from 10% to 30% of 7N NH$_3$ in methanol). 43a-43b was obtained as a light yellow oil (555 mg, quantitative).

MS (ESI$^+$) (+0.1% HCOOH): 139.22 [C$_6$H$_{10}$N$_4$+H]$^+$ (m/z)

Step C: 8-fluoro-3-methyl-6-oxo-9-[3-([1,2,4]tria-zolo-1-yl)-pyrrolidine]-2,3-dihydro-3,3a-diaza-phe-nalene-5-carboxylic acid and 8-fluoro-3-methyl-6-oxo-9-[3-([1,3,4]triazolo-pyrrolidine-2,3-dihydro-6H-1-oxa-3,3a-diaza-phenalene-5-carboxylic acid (44a-44b)

The title compound was prepared utilizing the procedure for the preparation of 5a except substituting 4a for 43a-43b (555 mg, 4.02 mmol, 2.8 eq.). The precipitate was filtered and washed with water; the residue was triturated in hot methanol and gave after filtration the title compound as a yellow solid (371 mg, 65%).

HPLC (gradient 5% to 95% ACN in $H_2O$): >99%
MS (ESI+) (+0.1% HCOOH): 401.2 $[C_{18}H_{17}FN_6O_4+H]^+$ (m/z)
mp=277-279° C.

EXAMPLE 22

8-fluoro-3-methyl-6-oxo-9-[3-([1,2,3]triazolo-1-yl)-pyrrolidine]-2,3-dihydro-6H-1-oxa-3,3a-diaza-phe-nalene-5-carboxylic acid and 8-fluoro-3-methyl-6-oxo-9-[3-([1,2,5]triazolo-1-yl)- pyrrolidine- 2,3-dihydro-6H-1-oxa-3,3a-diaza-phenalene-5-carboxylic acid (49a-49b)

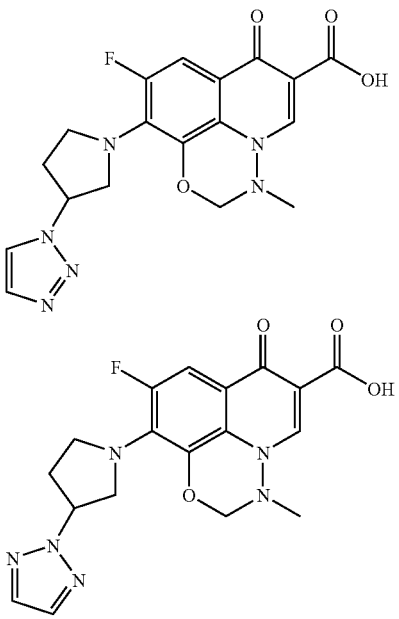

Step A: Preparation of 47a-47b

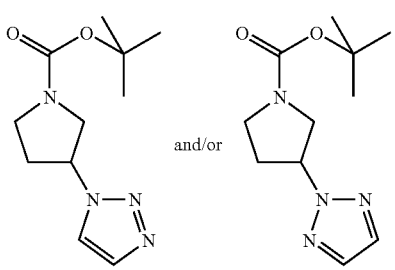

The title compound was prepared according to the procedure reported in US2003/0225107 except substituting 5(R)-3-[4-(1-cyanocyclopropan-1-yl]-5-methanesulfonyloxym-ethyloxazolidin-2-one for 45 {Genevois-Borella, 2005 #21}

(1.6 g, 8.53 mmol, 1.0 eq.). The resulting crude product was purified by flash chromatography on silica gel, eluting with cyclohexane-ethyl acetate (1:0 to 1:1) to afford 47a-47b as a white solid (1.4 g, 69%).

Step B: Preparation of 48a-48b

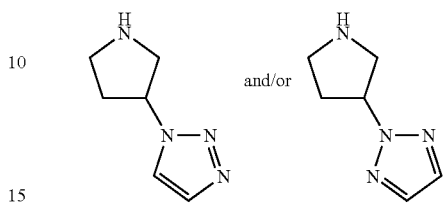

Utilizing the procedure described in the preparation of 4c except substituting 3c for 47a-47b (1.9 g, 7.97 mmol, 1.0 eq.) with 10 mL of 4N HCl in dioxane. The residue was purified by flash chromatography on silica gel, eluting with dichloromethane—7N $NH_3$ in methanol (gradient from 0% to 10% of 7N $NH_3$ in methanol). The title compound was obtained as a white solid (807 mg, 73%).

MS (ESI+) (+0.1% HCOOH): 139.05 $[C_6H_{10}N_4+H]^+$ (m/z)

Step C: 8-fluoro-3-methyl-6-oxo-9-[3-([1,2,3]tria-zolo-1-yl)-pyrrolidine]- 2,3-dihydro-6H-1-oxa-3,3a-diaza-phenalene-5-carboxylic acid and 8-fluoro-3-methyl-6-oxo-9-[3-([1,2,5]triazolo-1-yl)-pyrrolidine-2,3-dihydro-6H-1-oxa-3,3a-diaza-phenalene-5-carboxylic acid (49a-49b)

Utilizing the procedure described in the preparation of 5c except substituting 4c for 48a-48b (800 mg, 5.79 mmol, 3.0 eq.). The reaction was poured in ethanol; the precipitate was filtrated and washed with methanol to afford the title compound as a yellow solid (641 mg, 83%).

HPLC (gradient 5% to 95% ACN in $H_2O$): >95%
MS (ESI+) (+0.1% HCOOH): 400.99 $[C_{18}H_{17}FN_6O_4+H]^+$ (m/z)
mp=278-279° C.° C., dec.

EXAMPLE 23

8-Fluoro-3-methyl-6-oxo-9-(3-[1,2,3]triazol-1-yl-pyrrolidin-1-yl)-2,3-dihydro-6H-1-oxa-3,3a-diaza-phenalene-5-carboxylic acid (49a)

Step A: Preparation of 47a

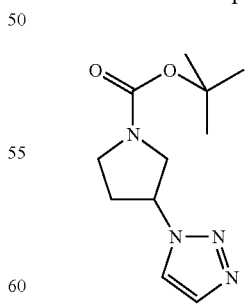

The title compound was prepared according to the procedure reported in US2003/0225107 except substituting 5(R)-azidomethyl-3-[4-(1-cyanocyclopropan-1-yl)phenyl]oxazo-lidin-2-one for 50 (EP1500643, 1.5 g, 7.07 mmol, 1.0 eq.). The reaction mixture was evaporated under reduced pressure to afford 47a as a yellow oil (1.7 g, quantitative).

Step B: Preparation of 48a

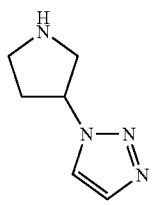

Utilizing the procedure described in PREPARATION of 4c except substituting 3c for 47a (1.7 g, 7.07 mmol) with 10 mL of 4N HCl in dioxane. The residue was purified by flash chromatography on silica gel, eluting with dichloromethane—7N $NH_3$ in methanol (gradient from 0% to 5% of 7N $NH_3$ in methanol). The title compound was obtained as a white solid (900 mg, 92%).

Step C: 8-Fluoro-3-methyl-6-oxo-9-(3-[1,2,3]triazol-1-yl-pyrrolidin-1-yl)-2,3-dihydro-6H-1-oxa-3,3a-diaza-phenalene-5-carboxylic acid (49a)

Utilizing the procedure described in PREPARATION of 5c except substituting 4c for 48a (1.03 g, 7.45 mmol, 4.0 eq.). The reaction was poured in ethanol, the precipitate was filtrated and washed with methanol to afford the title compound as a yellow solid (580 mg, 78%)

HPLC (gradient 5% to 95% ACN in $H_2O$): >99%

MS (ESI$^+$) (+0.1% HCOOH): 401.19 $[C_{18}H_{17}FN_6O_4+H]^+$ (m/z)

mp=264° C., dec.

EXAMPLE 24

8-Fluoro-3-methyl-6-oxo-9-[3-(1H-tetrazol-5-yl)-pyrrolidin-1-yl]-2,3-dihydro-6H-1-oxa-3,3a-diaza-phenalene-5-carboxylic acid (54)

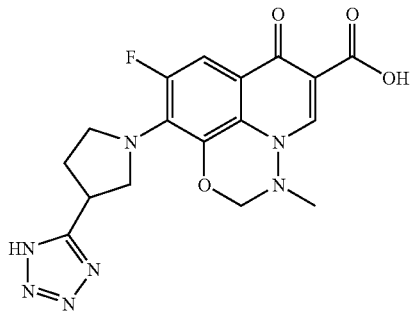

Step A: Preparation of 51

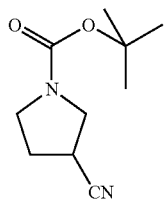

To a solution of 45 (4.66 g, 18.7 mmol, 1.0 eq.) in acetonitrile (10 mL) was added tetrabutylammonium cyanide (10.0 g, 37.4 mmol, 2.0 eq.), the reaction mixture was stirred at 65° C. overnight. After cooling the mixture was diluted with ethyl acetate and washed with a saturated aqueous $NaHCO_3$ solution. The organic extracts were dried over anhydrous sodium sulphate and evaporated under reduced pressure. The resulting crude product was purified by flash chromatography on silica gel, eluting with cyclohexane-ethyl acetate (1:0 to 1:1) to afford 51 as a yellow oil (2.9 g, 79%).

Step B: Preparation of 52

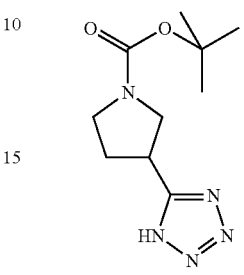

To a solution of 51 (1.0 g, 5.1 mmol, 1.0 eq.) in toluene (10 mL) were added sodium azide (0.497 g, 7.64 mmol, 1.5 eq.) and triethylamine hydrochloride, the reaction mixture was stirred at 100° C. for 24 hours. After cooling the mixture was diluted with ethyl acetate and washed with water. The organic extracts were dried over anhydrous sodium sulphate and evaporated under reduced pressure. The resulting crude product was purified by flash chromatography on silica gel, eluting with dichloromethane and 5% of methanol to afford the title compound as a yellow oil (1.0 g, 82%).

Step C: Preparation of 53

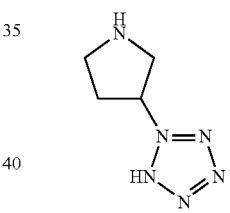

Utilizing the procedure described in the preparation of 4c except substituting 3c for 52 (1.09 g, 4.56 mmol, 1.0 eq.) with 10 mL of 4N HCl in dioxane. The residue was triturated with dichloromethane and filtrated. The resulting solid was triturated in 7N $NH_3$ methanol and evaporated under reduced pressure. The title compound was obtained as a beige solid (780 mg, quantitative).

Step D: 8-Fluoro-3-methyl-6-oxo-9-[3-(1H-tetrazol-5-yl)-pyrrolidin-1-yl]-2,3-dihydro-6H-1-oxa-3,3a-diaza-phenalene-5-carboxylic acid (54)

Utilizing the procedure described in the preparation of 5c except substituting 4c for 53 (780 mg, 5.61 mmol, 4.0 eq.). The reaction was poured in ethanol, the precipitate was filtrated. The residue was triturated and filtrated firstly with water, secondly with methanol and at last with dichloromethane to afford the title compound as a yellow solid (60 mg, 11 %)

HPLC (gradient 5% to 95% CAN in $H_2O$): >90%

MS (ESI$^+$) (+0.1% HCOOH): 402.28 $[C_{17}H_{16}PN_7O_4+H]^+$ (m/z)

mp=250° C., dec.

EXAMPLE 25

8-Fluoro-9-{3-[(furan-2-carbonyl)-amino]-pyrrolidin-1-yl}-3-methyl-6-oxo-2,3-dihydro-6H-1-oxa-3,3a-diaza-phenalene-5-carboxylic acid (57a)

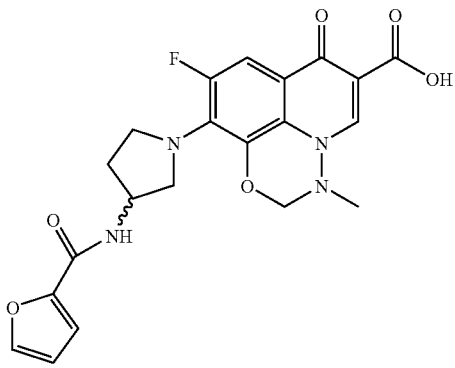

Step A: Preparation of 55a

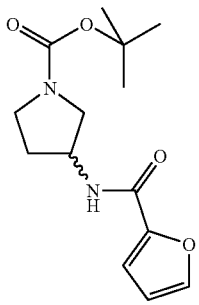

Utilizing the procedure described in the preparation of 11 except substituting 1 for 14 (1.0 g, 4.97 mmol, 1.0 eq.), the resulting crude product was purified by flash chromatography on silica gel, eluting with cyclohexane-ethyl acetate (8:2 to 0:1) to afford 55a (1.29 g, 92%) as a white solid.

Step B: Preparation of 56a

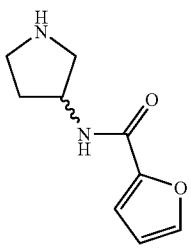

Utilizing the procedure described in the preparation of 4c except substituting 3c for 55a (1.29 g, 4.60 mmol, 1.0 eq.) with 10 mL of 4N HCl in isopropanol and dichloromethane for ethyl acetate. The residue was purified by flash chromatography on silica gel, eluting with dichloromethane—10% methanol then dichloromethane—7N NH$_3$ in methanol (gradient from 0% to 10% of 7N NH$_3$ in methanol). The title compound was obtained as a white gum (725 mg, 87%).

MS (ESI$^+$) (+0.1% HCOOH): 181.33 [C$_9$H$_{12}$N$_2$O$_2$+H]$^+$ (m/z)

Step C: 8-Fluoro-9-{3-[(furan-2-carbonyl)-amino]-pyrrolidin-1-yl}-3-methyl-6-oxo-2,3-dihydro-6H-1-oxa-3,3a-diaza-phenalene-5-carboxylic acid (57a)

Utilising the procedure for the preparation of 5a, except substituting 4a for 56a (725 mg, 4.02 mmol, 3.0 eq.), after cooling the reaction was filtered. The crude solid was triturated with boiling ethanol and filtrated to afford the title compound as a beige solid (497 mg, 84%).

HPLC (gradient 5% to 80% ACN in H$_2$O): >95%

MS (ESI$^+$) (+0.1% HCOOH): 443.1 [C$_{21}$H$_{19}$FN$_4$O$_6$+H]$^+$ (m/z)

mp=306-308° C.

EXAMPLE 26

8-Fluoro-3-methyl-6-oxo-9-[3-(3,3,3-trifluoro-propionylamino)-pyrrolidin-1-yl]-2,3-dihydro-6H-1-oxa-3,3a-diaza-phenalene-5-carboxylic acid (57c)

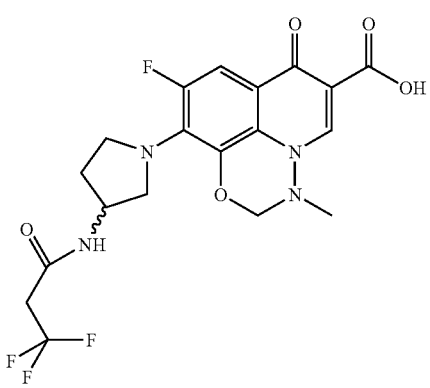

Step A: Preparation of 55c

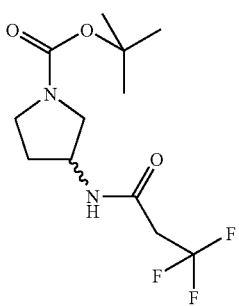

Utilizing the procedure for the preparation of 55b, except substituting cyclopentanecarbonylchloride for 3,3,3-trifluoro-propionyl chloride (2.3 g, 15.30 mmol, 1.5 eq.), the resulting crude product was purified by flash chromatography on silica gel, eluting with cyclohexane-ethyl acetate (8:2 to 1:1) to afford 55c (1.4 g, 46%) as a pale yellow oil.

Step B: Preparation of 56c

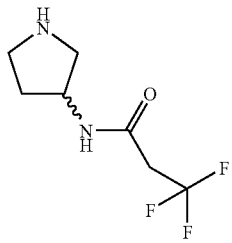

Utilizing the procedure described in the preparation of 4a-4b except substituting 3a-3b for 50c (1.4 g, 4.72 mmol, 1.0 eq.). The residue was purified by flash chromatography on silica gel, eluting with dichloromethane—methanol (gradient from 5% to 15% methanol) 56c (TFA salt) was obtained as a light yellow oil (1.4 g, quantitative).

MS (ESI$^+$) (+0.1% HCOOH): 197.13 $[C_7H_{11}F_3N_2O+H]^+$ (m/z)

Step C: 8-Fluoro-3-methyl-6-oxo-9-[3-(3,3,3-trifluoro-propionylamino)-pyrrolidin-1-yl]-2,3-dihydro-6H-1-oxa-3,3a-diaza-phenalene-5-carboxylic acid (57c)

Utilizing the procedure for the preparation of 5a, except substituting 4a for 56c (1.4 g, 4.51 mmol, 4.0 eq.), was evaporated under reduced pressure The crude solid was triturated with methanol and filtrated then the precipitate was triturated with boiling methanol and filtrated to afford the title compound as a yellow solid (277 mg, 57%).

HPLC (gradient 5% to 95% ACN in H$_2$O): >90%
MS (ESI$^+$) (+0.1% HCOOH): 459.0 $[C_{19}H_{18}F_4N_4O_5+H]^+$ (m/z)
mp=292° C., dec.

EXAMPLE 27

8-Fluoro-3-methyl-6-oxo-9-[3-(2,2,2-trifluoro-acetylamino)-pyrrolidin-1-yl]-2,3-dihydro-6H-1-oxa-3,3a-diaza-phenalene-5-carboxylic acid (57d)

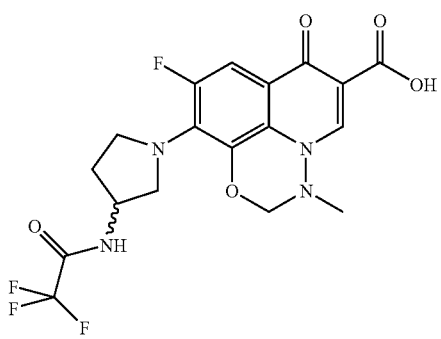

Step A: Preparation of 55d

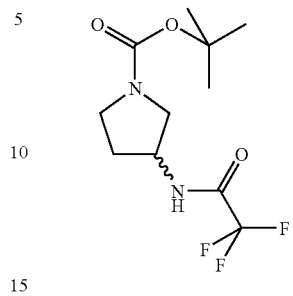

To a 0° C. solution of 14 (1.67 g, 8.96 mmol, 1.0 eq.) in dichloromethane (25 mL), Et$_3$N (2.5 mL, 17.93 mmol, 2.0 eq.) was added. After 30 minutes, trifluoroacetic anhydride (1.9 mL, 13.45 mmol, 1.5 eq.) was added slowly with 20 mg of DMAP and the reaction was stirred at room temperature overnight. The mixture was diluted with dichloromethane and washed with water; the organic extracts were dried over anhydrous sodium sulfate. The resulting crude product was purified by flash chromatography on silica gel, eluting with cyclohexane-ethyl acetate (9:1 to 7:3) to afford 55d (2.03 g, 80%) as a clear oil.

Step B: Preparation of 56d

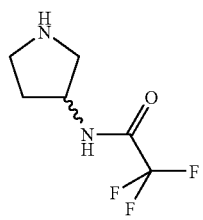

Utilizing the procedure described in the preparation of 4a-4b except substituting 3a-3b for 55d (2.03 g, 7.21 mmol, 1.0 eq.). The residue was used without further purification; 56d (TFA salt) was obtained as a light yellow oil (2.44 g, quantitative).

MS (ESI$^+$) (+0.1% HCOOH): 182.91 $[C_6H_9F_3N_2O+H]^+$ (m/z)

Step C: 8-Fluoro-3-methyl-6-oxo-9-[3-(2,2,2-trifluoro-acetylamino)-pyrrolidin-1-yl]-2,3-hydro-6H-1-oxa-3,3a-diaza-phenalene-5-carboxylic acid (57d)

Utilizing the procedure for the preparation of 5a, except substituting 4a for 56d (1.2 g, 4.05 mmol, 3.0 eq.); the reaction mixture was filtered and the precipitate was triturated with boiling methanol and filtrated to afford the title compound as a yellow solid (263 mg, 42%).

HPLC (gradient 5% to 95% ACN in H$_2$O): >95%
MS (ESI$^+$) (+0.1% HCOOH): 444.9 $[C_{18}H_{16}F_4N_4O_5+H]^+$ (m/z)
mp=281-283° C.

EXAMPLE 28

8-Fluoro-3-methyl-6-oxo-9-[(S)-3-(2,2,2-trifluoro-acetylamino)-pyrrolidin-1-yl]-2,3-dihydro-6H-1-oxa-3,3a-diaza-phenalene-5-carboxylic acid (57e)

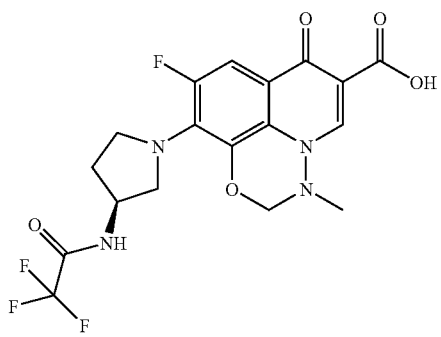

Utilizing the procedure for the preparation of 5a, except substituting 4a for 56e{Herling, 2003 #23}(1.0 g, 3.38 mmol, 3.0 eq.). The reaction mixture was filtered and the precipitate was triturated with boiling methanol and filtrated to afford the title compound as a yellow solid (64 mg, 13%).

HPLC (gradient 5% to 95% ACN in $H_2O$): >99%

MS (ESI$^+$) (+0.1% HCOOH): 445.3 $[C_{18}H_{16}F_4N_4O_5+H]^+$ (m/z)

mp=273-275° C.

EXAMPLE 29

8-Fluoro-3-methyl-6-oxo-9-[(R)-3-(2,2,2-trifluoro-acetylamino)-pyrrolidin-1-yl]-2,3-dihydro-6H-1-oxa-3,3a-diaza-phenalene-5-carboxylic acid (57f)

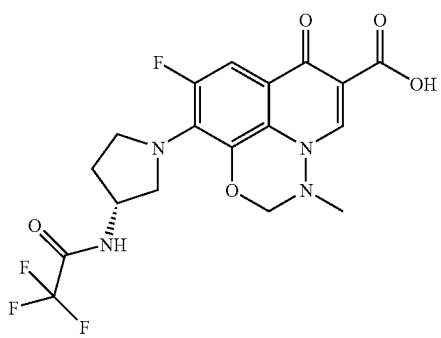

Utilizing the procedure for the preparation of 5a, except substituting 4a for 56f{Hudson, 2006 #8}1.5 g, 5.06 mmol, 3.0 eq.). The reaction mixture was filtered and the precipitate was triturated with boiling methanol and filtrated to afford the title compound as a yellow solid (375 mg, 50%).

HPLC (gradient 5% to 95% ACN in $H_2O$): >99%

MS (ESI$^+$) (+0.1% HCOOH): 445.2 $[C_{18}H_{16}F_4N_4O_5+H]^+$ (m/z)

mp=273-275° C.

EXAMPLE 30

8-Fluoro-3-methyl-6-oxo-9-(3-trifluoromethane-sulfonylamino-pyrrolidin-1-yl)-2,3-dihydro-6H-1-oxa-3,3a-diaza-phenalene-5-carboxylic acid (60a)

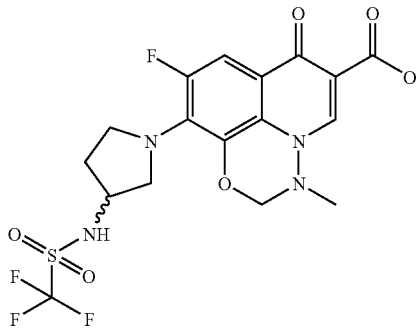

Step A: Preparation of 58a

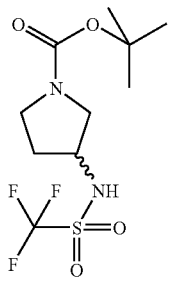

To a 0° C. solution of 14 (1.5 g, 8.05 mmol, 1.0 eq.) in dichloromethane (30 mL), $Et_3N$ (3.4 mL, 24.16 mmol, 3.0 eq.) was added. After 15 minutes, trifluoromethanesulfonic anhydride (1.7 mL, 9.66 mmol, 1.2 eq.) was added slowly and the reaction was stirred at room temperature for 6 hours. The mixture was diluted with dichloromethane and washed with a saturated aqueous $NaHCO_3$ solution; the organic extracts were dried over anhydrous sodium sulfate and evaporated under reduced pressure. The resulting crude product was purified by flash chromatography on silica gel, eluting with cyclohexane-ethyl acetate (9:1 to 6:4) to afford 58a (1.1 g, 42%) as a pale yellow oil.

Step B: Preparation of 59a

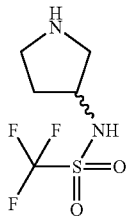

Utilizing the procedure described in the preparation of 4a-4b except substituting 3a-3b for 58a (1.1 g, 3.45 mmol, 1.0 eq.). The residue was purified by flash chromatography on silica gel, eluting with dichloromethane—methanol (gradient from 5% to 15% methanol) 59a (TFA salt) was obtained as a yellow oil (1.0 g, 87%).

Step C: 8-Fluoro-3-methyl-6-oxo-9-(3-trifluoromethanesulfonylarnino-pyrrolidin-1-yl)-2,3-dihydro-6H-1-oxa-3,3a-diaza-phenalene-5-carboxylic acid (60a)

Utilizing the procedure for the preparation of 5a, except substituting 4a for 59a (1.0 g, 3.01 mmol, 3.5 eq.), was evaporated under reduced pressure. The crude solid was triturated with methanol and filtrated then the precipitate was triturated with boiling methanol and filtrated to afford the title compound as a yellow solid (30 mg, 6%).

HPLC (gradient 5% to 95% ACN in $H_2O$): >99%
MS (ESI$^+$) (+0.1% HCOOH): 459.0 [$C_{17}H_{16}F_4N_4O_6S$+H]$^+$ (m/z)
mp=270-272° C.

EXAMPLE 31

8-Fluoro-9-(3-methanesulfonylamino-pyrrolidin-1-yl)-3-methyl-6-oxo-2,3-dihydro-6H-1-oxa-3,3a-diaza-phenalene-5-carboxylic acid (60b)

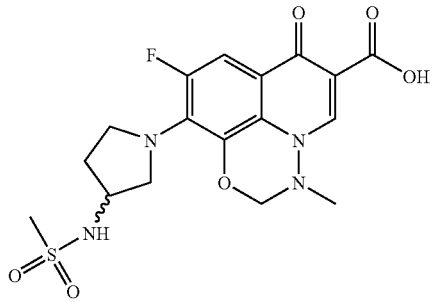

Utilizing the procedure described in the preparation of 5c except substituting 4c for 59b {Ueda, 1999 #24}(1.22 g, 7.44 mmol, 4.0 eq.). The reaction was evaporated under reduced pressure; the residue was triturated with ethanol and filtrated. The solid was then triturated with a mixture of dichloromethane/methanol and filtrated to afford the title compound as a yellow solid (390 mg, 49%)

HPLC (gradient 5% to 95% ACN in $H_2O$): >95%
MS (ESI$^+$) (+0.1% HCOOH): 426.87 [$C_{17}H_{19}FN_4O_6S$+H]$^+$ (m/z)
mp=261° C., dec.

EXAMPLE 32

8-fluoro-9-[(R,S)-4-hydroxy-3,3-dimethyl-pyrrolidine-1-yl]-3-methyl-6-oxo-2,3-dihydro-6H-1-oxa-3,3a-diaza-phenalene-5-carboxylic acid (75a)

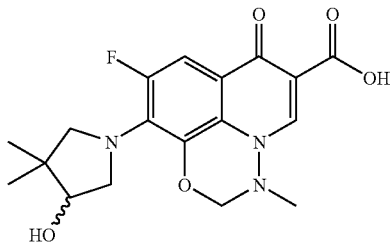

Step A: Preparation of 73a

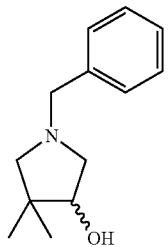

73a was prepared according to the procedure described by Di Cesare, et al, J. Med. Chem 1992, 35,(22) 4205-13, but starting with the (+/−)pantolactone.

Step B: Preparation of 74a

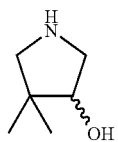

To a solution of 73a (1.0 g, 4.87 mmol, 1.0 eq.) in methanol (20 mL), Pd/C (100 mg) and 5N HCl in isopropanol (1.95 ml, 9.74 mmol, 2.0 eq.) were added. The reaction mixture was submitted to hydrogenation at atmospheric pressure and room temperature for 48 hours. The mixture was filtrated over Celite® and evaporated under reduced pressure. The residue was purified by flash chromatography on silica gel, eluting with dichloromethane—7N $NH_3$ in methanol (gradient from 5% to 40% of 7N $NH_3$ in methanol to afford the title compound as a white solid (170 mg, 30%).

Step C: 8-fluoro-9-[(R,S)-4-hydroxy-3,3-dimethyl-pyrrolidine-1-yl]-3-methyl-6-oxo-2,3-dihydro-6H-1-oxa-3,3a-diaza-phenalene-5-carboxylic acid (75a)

Utilizing the procedure described in the preparation of 5c except substituting 4c for 74a (170 mg, 1.48 mmol, 2.0 eq.). The reaction was evaporated under reduced pressure; the residue was triturated with water and filtrated. The solid was then triturated with ethanol, filtrated and washed with methanol. An analytical sample was obtained by preparative TLC purification eluting with dichloromethane—2% methanol to afford the title compound as a yellow solid (40 mg, 14%).

HPLC (gradient 5% to 95% ACN in $H_2O$): >90%
MS (ESI$^+$) (+0.1% HCOOH): 377.69 [$C_{18}H_{20}FN_3O_5$+H]$^+$ (m/z)
mp=281° C., dec.

EXAMPLE 33

9-((R,S)-4-Amino-3,3-dimethyl-pyrrolidin-1-yl)-8-fluoro-3-methyl-6-oxo-2,3-dihydro-6H-1-oxa-3,3a-diaza-phenalene-5-carboxylic acid (75b)

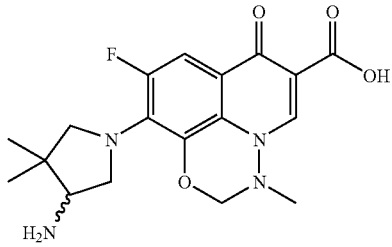

Step A: Preparation of 74b

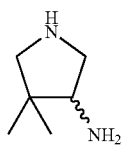

74b was prepared according to the procedure described by Di Cesare, et al, J. Med. Chem 1992, 35,(22) 4205-13, but starting with the (+/−)pantolactone.

Step B: 9-((R,S)-4-Amino-3,3-dimethyl-pyrrolidin-1-yl)-8-fluoro-3-methyl-6-oxo-2,3-dihydro-6H-1-oxa-3,3a-diaza-phenalene-5-carboxylic acid (75b).

Utilizing the procedure described for the preparation of 5a, 75b was obtained with TNOC (304 mg, 1.07 mmol, 1.0 eq.), 74b{Di Cesare, 1992 #11} (370 mg, 3.24 mmol, 3.0 eq.) in pyridine and n-methylmorpholine (0.24mL, 2.16 mmol, 2.0 eq.). The mixture was evaporated; the residue was purified on SCX cartridge eluting with methanol—triethylamine (gradient from 0% to 1% of triethylamine) to afford the title compound as a yellow solid (40 mg, 21%)

HPLC (gradient 5% to 95% ACN in $H_2O$): >95%
MS (ESI$^+$) (+0.1% HCOOH): 376.93 $[C_{18}H_{21}FN_4O_4+H]^+$ (m/z)
mp=237° C., dec.

EXAMPLE 34

9-((S)-4-Amino-3,3-dimethyl-pyrrolidin-1-yl)-8-fluoro-3-methyl-6-oxo-2,3-dihydro-6H-1-oxa-3,3a-diaza-phenalene-5-carboxylic acid (75c)

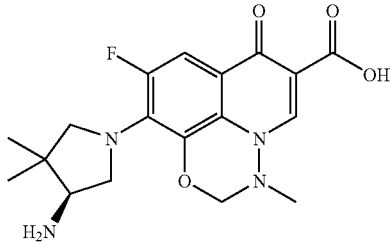

Utilizing the procedure described for the preparation of 5a, 75c was obtained with TNOC (630 mg, 2.23 mmol, 1.0 eq.), 74c{Di Cesare, 1992 #11} (1.1 g, 7.30 mmol, 3.3 eq.) in pyridine and n-methylmorpholine (1.0 mL, 9.10 mmol, 4.0 eq.). The mixture was evaporated; the residue was triturated several times with boiling methanol and ethanol and filtrated to afford the title compound as a yellow solid (144 mg, 10%)

HPLC (gradient 5% to 95% ACN in $H_2O$): >99%
MS (ESI$^+$) (+0.1% HCOOH): 377.4 $[C_{18}H_{21}FN_4O_4+H]^+$ (m/z)
mp=230° C., dec.

EXAMPLE 35

9-((R)-4-Amino-3,3-dimethyl-pyrrolidin-1-yl)-8-fluoro-3-methyl-6-oxo-2,3-dihydro-6H-1-oxa-3,3a-diaza-phenalene-5-carboxylic acid (75d)

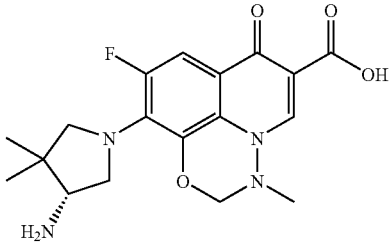

Utilizing the procedure described for the preparation of 5a, 75d was obtained with TNOC (140 mg, 0.50 mmol, 1.0 eq.), 74d (200 mg, 1.33 mmol, 2.7 eq.) in 5 mL of pyridine and n-methylmorpholine (0.20 mL, 0.91 mmol, 3.6 eq.). The mixture was evaporated; the residue was triturated several times with boiling methanol and filtrated to afford the title compound as a yellow solid (60 mg, 31%)

HPLC (gradient 5% to 95% ACN in $H_2O$): >90%
MS (ESI$^+$) (+0.1% HCOOH): 377.4 $[C_{18}H_{21}FN_4O_4+H]^+$ (m/z)
mp=222° C., dec.

EXAMPLE 36

8-Fluoro-9-(3-hydroxy-3-thiazol-2-yl-pyrrolidin-1-yl)-3-methyl-6-oxo-2,3-dihydro-6H-1-oxa-3,3a-diaza-phenalene-5-carboxylic acid (82)

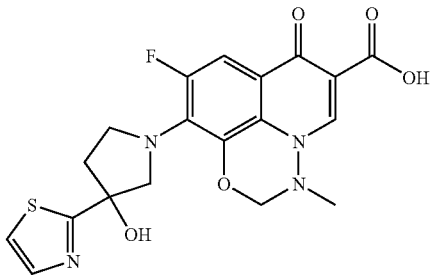

Step A: Preparation of 80

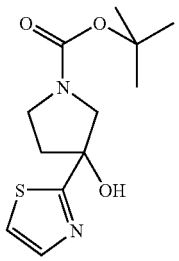

To a −70° C. solution of bromothiazole (0.8 mL, 8.77 mmol, 1.1 eq.) in diethyl ether, 2.5 N butyl lithium in hexanes (3.2 mL, 7.98 mmol, 1.0 eq.) was added. After 15 minutes, a solution of 3-oxo-pyrrolidine-1-carboxylic acid tert-butyl ester (1.47 g, 7.98 mmol, 1.0 eq.) in tetrahydrofurane (20 mL) was added. The mixture was allowed to reach room temperature after 45 minutes. A saturated aqueous ammonium chloride was added with 20 mL of ethyl acetate, the mixture was decanted and the organic phase was washed with water. The organic extracts were dried over sodium sulphate and evaporated under reduced pressure. The resulting crude product was purified by flash chromatography on silica gel, eluting with cyclohexane-ethyl acetate (9:1 to 7:3) to afford 80 (1.41 g, 66%) as a light yellow oil.

Step B: Preparation of 81

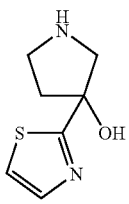

Utilizing the procedure described in the preparation of 4a-4b except substituting 3a-3b for 80 (1.41 g, 5.21 mmol). The residue was purified by flash chromatography on silica gel, eluting with dichloromethane—methanol (gradient from 5% to 20% methanol). The title compound (trifluoroacetic acid salt) was obtained as a light brown oil (1.4mg, 74%).

Step C: 8-Fluoro-9-(3-hydroxy-3-thiazol-2-yl-pyrrolidin-1-yl)-3-methyl-6-oxo-2,3-dihydro-1-oxa-3,3a-diaza-phenalene-5-carboxylic acid (82)

Utilizing the procedure described for the preparation of 5a, 82 was obtained with TNOC (475 mg, 1.68 mmol, 1.0 eq.), 81 as a trifluoroacetic acid salt-(1.4 g, 5.05 mmol, 3.0 eq.) in 6 mL of pyridine and n-methyhnorpholine (1.5 mL). The reaction was evaporated under reduced pressure and the residue was triturated with boiling methanol and filtrated to afford the title compound as a yellow solid (476 mg, 67%)

HPLC (gradient 5% to 95% ACN in $H_2O$): >99%
MS (ESI$^+$) (+0.1% HCOOH): 432.9 $[C_{19}H_{17}FN_4O_5S+H]^+$ (m/z)
mp=252-253° C.

EXAMPLE 37

8-Fluoro-9-[3-(1-hydroxy-ethyl)-pyrrolidin-1-yl]-3-methyl-6-oxo-2,3-dihydro-6H-1-oxa-3,3a-diaza-phenalene-5-carboxylic acid (88)

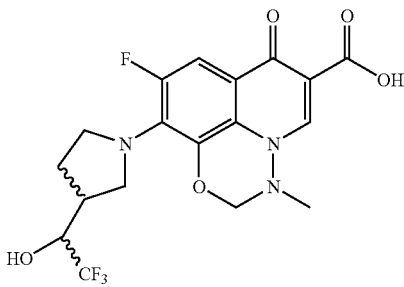

Step A: Preparation of 84

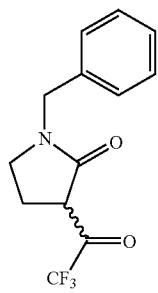

Compound 84 was prepared according to the preparation reported in WO2005/026154 except substituting 1-(1R-phenyl-ethyl)-pyrrolidin-2-one for the commercially available 1-benzyl-2-pyrrolidinone (7.0 g, 39.95 mmol, 1.0 eq.). 84 was obtained as a brown oil (9.15 g, 84%).

Step B: Preparation of 85

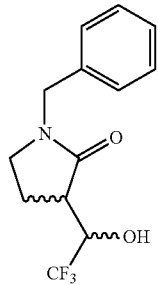

Compound 85 was prepared according to the preparation reported in WO2005/026154 except substituting 3-(2,2,2-trifluoro-acetyl)-1-(1R-phenyl-ethyl)-pyrrolidin-2-one for 84 (3.25 g, 11.9 mmol, 1.0 eq.) and zinc borohydride for potassium borohydride. 85 was obtained as a pale yellow oil (2.95 g, 89%).

Step C: Preparation of 86

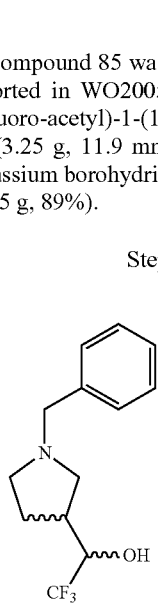

Compound 86 was prepared according to the preparation reported in WO2005/026154 except substituting 3-(2,2,2-trifluoro-1-hydroxy-ethyl)-1-(1R-phenyl-ethyl)-pyrrolidin-2-one for 84 (2.95 g, 10.79 mmol, 1.0 eq.), 86 was obtained as a pale yellow oil (2.68 g, 94%).
MS (ESI$^+$) (+0.1% HCOOH): 260.17 $[C_{13}H_{16}F_3NO+H]^+$ (m/z)

57
Step D: Preparation of 87

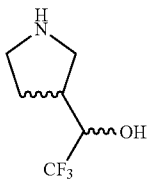

To a solution of 86 (1.7 g, 6.55 mmol, 1.0 eq.) in methanol (25 mL), Pd/C (200 mg) and 5N HCl in isopropanol (3.0 mL, 15.0 mmol, 2.3 eq.) were added. The reaction mixture was submitted to hydrogenation at 8 bars and at 40° C. for 24 hours. The mixture was filtrated over Celite® and evaporated under reduced pressure. The residue was purified by flash chromatography dichloromethane—methanol (gradient from 5% to 20% of methanol) to afford the title compound (208 mg, 15%) as a pale green oil.

MS (ESI$^+$) (+0.1% HCOOH): 170.1 $[C_6H_{10}F_3N_O+H]^+$ (m/z)

Step E: 8-Fluoro-9-[3-(1-hydroxy-ethyl)-pyrrolidin-1-yl]-3-methyl-6-oxo-2,3-dihydro-6H-1-oxa-3,3a-diaza-phenalene-5-carboxylic acid (88)

Utilizing the procedure described for the preparation of 5a, 88 was obtained from TNOC (300 mg, 1.06 mmol, 1.0 eq.) and 87 as a hydrochloride salt-(707 mg, 3.44 mmol, 3.2 eq.) in 10 mL of pyridine and triethylamine (0.80 mL, 5.73 mmol, 5.4 eq.). The reaction was evaporated under reduced pressure and the residue was purified by preparative TLC purification eluting with dichloromethane and 5% of methanol to afford the title compound as a yellow solid (19 mg, 7%)

HPLC (gradient 5% to 95% ACN in H$_2$O): >95%
MS (ESI$^+$) (+0.1% HCOOH): 432.3 $[C_{18}H_{17}F_4N_3O_5+H]^+$ (m/z)
mp=308-310° C.

EXAMPLE 38

8-Fluoro-9-[3-(hydroxy-thiazol-2-yl-methyl)-pyrrolidin-1-yl]-3-methyl-6-oxo-2,3-dihydro-6H-1-oxa-3,3a-diaza-phenalene-5-carboxylic acid (92)

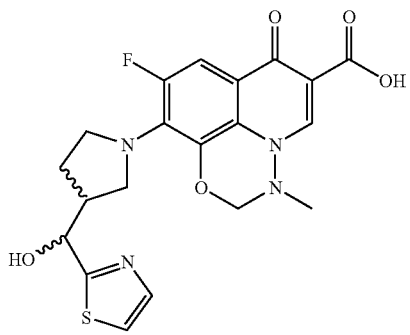

58
Step A: Preparation of 89

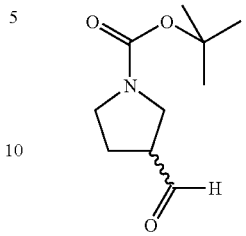

Compound 89 was prepared according to the procedure reported in WO2005/026154 except substituting benzyloxy-carbonyl-pyrrolidin-3-yl-methanol for the commercially available 3-hydroxymethyl-pyrrolidine-1-carboxylic acid tert-butyl ester 6 (3.4 g, 17.06 mmol, 1.0 eq.). 89 was obtained as a yellow oil (2.15 g, 82%).

Step B: Preparation of 90

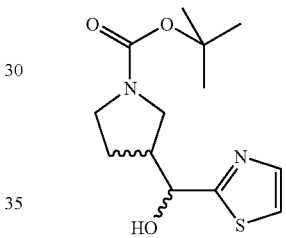

Compound 90 was prepared according to the procedure reported in WO2005/026154 except substituting benzyloxy-carbonyl-pyrrolidin-3-yl-thiazol-2-yl-methanol for 89 (2.15 g, 10.79 mmol, 1.0 eq.). 89 was obtained as a yellow oil (2.39 g, 78%).

Step C: Preparation of 91

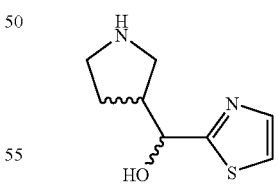

Utilizing the procedure described in the preparation of 4a-4b except substituting 3a-3b for 89 (1.65 g, 5.80 mmol). The residue was purified by flash chromatography on silica gel, eluting with dichloromethane—20%methanol then dichloromethane—20% 7N NH$_3$ in methanol, the title compound was obtained as a colorless oil (1.3 g, quantitative).

MS (ESI$^+$) (+0.1% HCOOH): 185.02 $[C_8H_{12}N_2OS+H]^+$ (m/z)

Step D: 8-Fluoro-9-[3-(hydroxy-thiazol-2-yl-methyl)-pyrrolidin-1-yl]-3-methyl-6-oxo-2,3-dihydro-6H-1-oxa-3,3a-diaza-phenalene-5-carboxylic acid (92)

Utilizing the procedure for the preparation of 10b except substituting 9b for 91 (1.3 g, 7.05 mmol, 3.6 eq.). The reaction was evaporated under reduced pressure; the residue was triturated with boiling methanol and filtrated to afford the title compound as a yellow solid (610 mg, 70%).

HPLC (gradient 5% to 95% ACN in $H_2O$): >95%

MS ($ESI^+$) (+0.1% HCOOH): 446.9 $[C_{20}H_{19}FN_4O_5S+H]^+$ (m/z)

mp=215-217° C.

EXAMPLE 39

9-[3-(Amino-thiazol-2-yl-methyl)-pyrrolidin-1-yl]-8-fluoro-3-methyl-6-oxo-2,3-dihydro-6H-1-oxa-3,3a-diaza-phenalene-5-carboxylic acid (96)

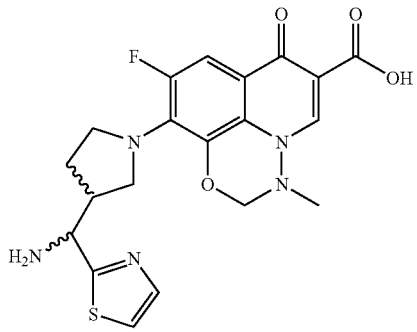

Step A: Preparation of 93

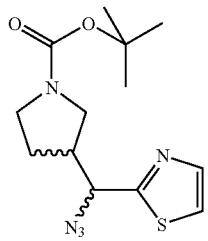

To a 0° C. solution of 90 (2.35 g, 8.26 mmol, 1.0 eq.) in dichloromethane (60 mL), triethylamine (2.3 mL, 16.50 mmol, 2.0 eq.) and methanesulfonyl chloride (1.3 mL, 16.80 mmol, 2.0 eq.) were added. The reaction mixture was stirred at room temperature for 6 hours and washed first with aqueous 1 N HCl and then with a saturated aqueous $NaHCO_3$ solution. The organic extracts were dried over sodium sulphate and evaporated under reduced pressure. The crude residue was dissolved in dimethylformamide and sodium azide (2.7 g, 41.53 mmol, 5.0 eq.) were added, the reaction was heated at 85° C. for 16 hours. A saturated aqueous ammonium chloride solution was added and the mixture was extracted with ethyl acetate, the solution was then washed with water twice, the organic extracts were dried over sodium sulphate and evaporated under reduced pressure. The resulting crude product was purified by flash chromatography on silica gel, eluting with cyclohexane-ethyl acetate (7:3) to afford 93 (2.1 g, 82%) as a yellow oil.

Step B: Preparation of 94

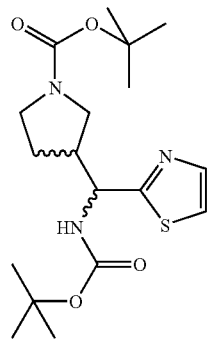

Compound 94 was prepared according to the procedure described in EP1182202 except substituting 4-(R)-[1-azido-1-(thiazol-2-yl)methyl]-1-[1-(R)-phenylethyl]-2-pyrrolidinone for 93 (1.5 g, 4.84 mmol, 1.0 eq.). 94 was obtained as a colorless oil (1.3 g, 70%).

HPLC (gradient 5% to 95% ACN in $H_2O$): >99%

MS ($ESI^+$) (+0.1% HCOOH): 384.3 $[C_{18}H_{29}N_3O_4S+H]^+$ (m/z)

Step C: Preparation of 95

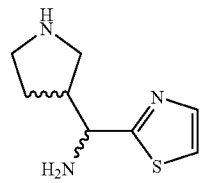

Compound 95 was prepared according to the procedure described in E1182202 except substituting 3-(R)-[1-tert-butoxy carbonylamino-1-(thiazol-2-yl)methyl]-1 benzyloxycarbonyl pyrrolidine for 94 (1.3 g, 3.39 mmol, 1.0 eq.). 95 (di-trifluoroacetic acid salt) was obtained as a colorless oil (1.35 g, quantitative).

HPLC (gradient 5% to 95% ACN in $H_2O$): >99%

MS ($ESI^+$) (+0.1% HCOOH): 184.1 $[C_8H_{13}N_3S+H]^+$ (m/z)

Step D: 9-[3-(Amino-thiazol-2-yl-methyl)-pyrrolidin-1-yl]-8-fluoro-3-methyl-6-oxo-2,3-dihydro-6H-1-oxa-3,3a-diaza-phenalene-5-carboxylic acid (96)

Utilizing the procedure described for the preparation of 5a, 96 was obtained from TNOC (80 mg, 0.28 mmol, 1.0 eq.) and 90 (200 mg, 0.49 mmol, 1.7 eq.) in 5 mL of pyridine and triethylamine (1.3 mL). The reaction was evaporated under reduced pressure and the residue was purified by preparative TLC purification eluting with dichloromethane and 5% of methanol to afford the title compound as a yellow solid (34 mg, 27%)

HPLC (gradient 5% to 95% ACN in $H_2O$): >99%

MS ($ESI^+$) (+0.1% HCOOH): 446.1 $[C_{20}H_{20}FN_4O_5S+H]^+$ (m/z)

mp=233-235° C.

EXAMPLE 40

8-fluoro-9-{3-[(Z/E)-methoxyimino]-pyrrolidin-1-yl}-3-methyl-6-oxo-2,3-dihydro-6-H-1-oxa-3,3a-diaza-phenalene-5-carboxylic acid (105)

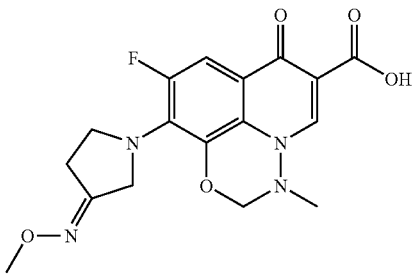

Step A: Preparation of 103

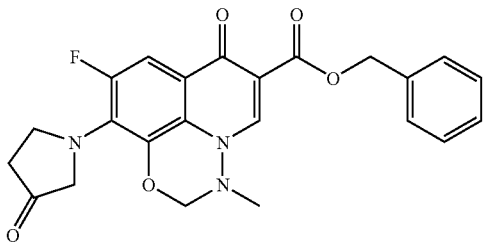

To a −78° C. solution of oxalyl chloride (0.5 mL, 5.73, mmol, 2.2 eq.) in dichloromethane (30 mL) were added dimethylsulfoxide (0.75 mL, 10.58 mmol, 4.0 eq.) and a solution of 9-{3-hydroxy-pyrrolidin-1-yl}-8-fluoro-3-methyl-6-oxo-2,3-dihydro-6-H-1-oxa-3,3a-diaza-phenalene-carboxylic acid benzyl ester 102 (1.16 g, 2.64 mmol, 1.0 eq.) in dichloromethane (30 mL). After 1 hour at -78° C., triethylamine (2.2 mL, 15.78 mmol, 6.0 eq.) was added. The reaction mixture was stirred 1 hour at −78° C., and then 1 hour at room temperature. The mixture was diluted with dichloromethane and washed with water; the organic extracts were dried over sodium sulphate and evaporated under reduced pressure. 103 was obtained as a beige solid (1.15g, quantitative).

MS (ESI$^+$) (+0.1% HCOOH): 438.3 [$C_{23}H_{20}FN_3O_5$+H]$^+$ (m/z)

Step B: Preparation of 104

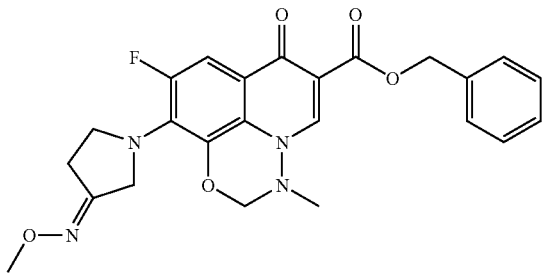

To a suspension 103 (1.15 g, 2.63 mmol, 1.0 eq.) in ethanol (25 mL) and THF (15 mL) were added methoxylamine hydrochloride (820 mg, 9.82 mmo, 3.7 eq) and a solution of sodium bicarbonate (750 mg, 8,93 mmol, 3.4 eq) in water (8 mL). The mixture was stirred at 40° C. for 16 hours. The reaction was concentrated under reduced pressure. The residue was dissolved in ethyl acetate and washed first with water and then with brine. The organic extracts were dried over anhydrous sodium-sulphate and were evaporated under reduced pressure to afford the title compound as a beige solid (1.19 g, 97%).

HPLC (gradient 5% to 95% ACN in H$_2$O): >90%

MS (ESI$^+$) (+0.1% HCOOH): 467.4 [$C_{24}H_{23}FN_4O_5$+H]$^+$ (m/z)

Step C: 8-fluoro-9-{3-[(Z/E)-methoxyimino]-pyrrolidin-1-yl}-3-methyl-6-oxo-2,3-dihydro-6-H-1-oxa-3,3a-diaza-phenalene-5-carboxylic acid (105)

A suspension of 104 (1.19 g, 2.55 mmol, 1.0 eq) in dichloromethane (25 mL) and methanol (10 mL) was added palladium on activated carbon 10% (300 mg, 0.25 mmol, 0.1 eq). The mixture was submitted to hydrogenation at room temperature under 1 atmosphere for 3 hours. The reaction mixture was filtered through Celite® and evaporated. The residue was triturated with methanol and the solid was filtered to afford the title compound as a yellow solid (800 mg, 83%).

HPLC (gradient 5% to 95% ACN in H$_2$O): >95%

MS (ESI$^+$) (+0.1% HCOOH): 377.2 [$C_{16}H_{17}FN_4O_5$+H]$^+$ (m/z)

mp=241-243° C.

EXAMPLE 41

8-Fluoro-3-methyl-6-oxo-9-[4-(pyrazin-2-ylamino)-piperidin]-1-yl]-2,3-dihydro-6H-1-oxa-3,3a-diaza-phenalene-5-carboxylic acid (108a)

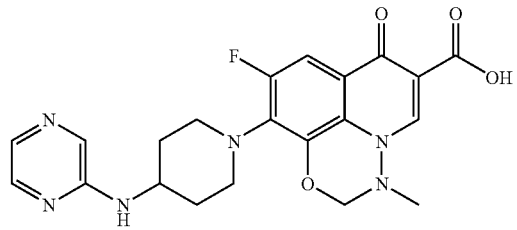

Step A: Preparation of 106a

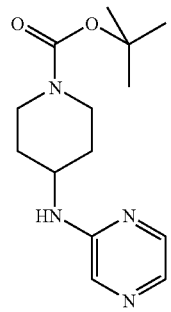

In a sealed tube, 30 mL of dry toluene was degazed with Argon during 15 minutes, palladium acetate (114 mg, 0.17 mmol, 0.04 eq.) and racemic-2,2'-bis(diphenylphosphino)-1,1'-binaphthyl (106 mg, 0.17 mmol, 0.04 eq.) were added and the mixture was degazed with Argon for 10 minutes. Then 2-chloropyrazine (500 mg, 4.37 mmol, 1.0 eq.), 4-amino-1-

Boc-piperidine (1.05 g, 5.24 mmol, 1.2 eq.) and sodium tert-butoxide (587 mg, 6.11 mmol, 1.4 eq.) were added and the mixture was stirred at 70° C. overnight. The reaction was concentrated in vacuum. The resulting crude product was purified by flash chromatography on silica gel, eluting with 100% ethyl acetate to afford 106a (1.0 g, 82%).

Step B: Preparation of 107a

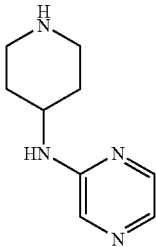

According to general procedure B except substituting TFA for 4N HCl in dioxane, 28a (1.4 g, 5.03 mmol, 1.0 eq.) was deprotected; the residue was purified by flash chromatography on silica gel, eluting with eluting dichloromethane 7N $NH_3$ in methanol (gradient from 5% to 20% of 7N $NH_3$ in methanol) to afford 107a (900 mg, quantitative).

MS (ESI$^+$) (+0.1% HCOOH): 179.24 $[C_9H_{14}N_4+H]^+$ (m/z)

Step C: 8-Fluoro-3-methyl-6-oxo-9-[4-(pyrazin-2-ylamino)-piperidin-1-yl]-2,3-dihydro-6H-1-oxa-3,3a-diaza-phenalene-5-carboxylic acid (108a)

According to general procedure A, TNOC (355 mg, 1.26 mmol, 1.0 eq.) was coupled with 29a (900 mg, 5.05 mmol, 4.0 eq.) and N-methylmorpholine (0.28 mL, 2.53 mmol, 2.0 eq.). The residue was triturated several times with hot methanol to afford the title compound as a beige solid (67 mg, 12%).

HPLC (gradient 5%-80% ACN in $H_2O$): >95%

MS (ESI$^+$) (+0.1% HCOOH): 441.14 $[C_{21}H_{21}FN_6O_4+H]^+$ (m/z)

mp=239° C., dec.

EXAMPLE 42

8-Fluoro-3-methyl-6-oxo-9-[4-(pyridin-2-ylamino)-piperidin-1-yl]-2,3-dihydro-6H-1-oxa-3,3a-diaza-phenalene-5-carboxylic acid (108b)

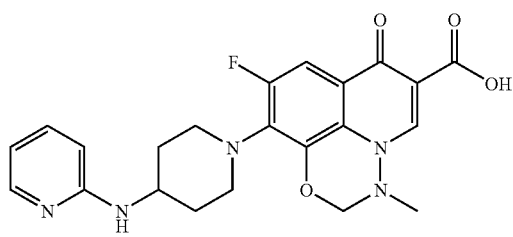

Step A: Preparation of 106b

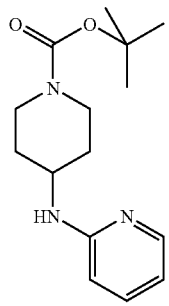

Utilizing the procedure described for the preparation of 107a except substituting 2-chloropyrazine for 2-chloropyridine (4.4 mmol). The resulting crude product was purified by flash chromatography on silica gel, eluting with cyclohexane-ethyl acetate (1:1) to afford 106b (1.2 g, 98%).

Step B: Preparation of 107b

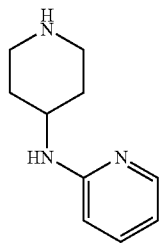

According to general procedure B, 106b (1.2 g, 4.31 mmol, 1.0 eq.) was deprotected; the residue was purified by flash chromatography on silica gel, eluting with eluting dichloromethane 7N $NH_3$ in methanol (gradient from 0% to 20% of 7N $NH_3$ in methanol) to afford 107b (1.0 g, quantitative).

MS (ESI$^+$) (+0.1% HCOOH): 178.18 $[C_{10}H_{15}N_3+H]^+$ (m/z)

Step C: 8-Fluoro-3-methyl-6-oxo-9-[4-(pyridin-2-ylamino)-piperidin-1-yl]-2,3-dihydro-6H-1-oxa-3,3a-diaza-phenalene-5-carboxylic acid (108b)

According to general procedure A, TNOC (530 mg, 1.88 mmol, 1.0 eq.) was coupled with 107b (1.0 g, 5.54 mmol, 3.0 eq.) and N-methylmorpholine (0.41 mL, 3.76 mmol, 2.0 eq.). The residue was triturated several times with hot methanol, an analytical sample was obtained by preparative TLC purification eluting with dichloromethane—methanol (gradient from 2.5% to 5% of methanol) to afford the title compound as a yellow solid (80 mg, 10%).

HPLC (gradient 5%-80% ACN in $H_2O$): >95%

MS (ESI$^+$) (+0.1% HCOOH): 440.1 $[C_{22}H_{22}FN_5O_4+H]^+$ (m/z)

mp=264° C., dec.

EXAMPLE 43

8-fluoro-3-methyl-6-oxo-9-[4-(thiazol-2-ylamino)-piperidin-1-yl]-2,3-dihydro-6H-1-oxa-3,3a-diaza-phenalene-5-carboxylic acid (111)

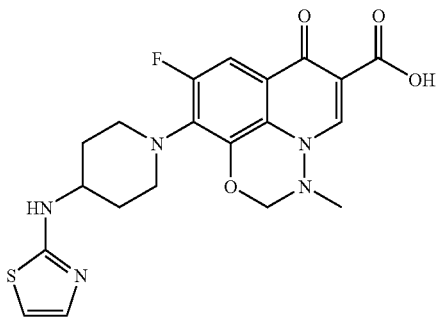

Step A: Preparation of 109

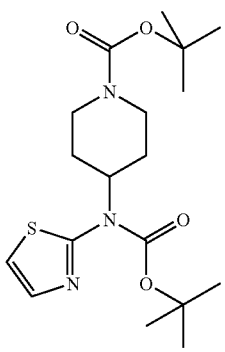

To a 0° C. solution of the commercially available tert-butyl 4-hydroxy-1-piperidine-carboxylate (1.5 g, 7.45 mmol, 1.2 eq.) in dry THF (20 mL), triphenylphosphine (2.4 g, 9.31 mmol, 1.5 eq.) was added. After complete dissolution, diethylazodicarboxylate –40% w/v in toluene- (4 mL, 9.31 mmol, 1.5 eq.) was added dropwise followed by thiazol-2-yl-carbamic acid tert-butyl ester g, 5.99 mmol, 1.0 eq.). The mixture was stirred at RT for 18 hours. The reaction was evaporated under reduced pressure. The resulting crude product was purified by flash chromatography on silica gel, eluting with cyclohexane-ethyl acetate (95:5 to 85:15) to afford 109 as a colorless gum (1.95 g, 85%)

Step B: Preparation of 110

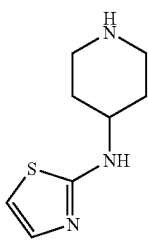

109 (1.95 g, 5.08 mmol) was dissolved in ethyl acetate (10 mL) and 4N HCl in dioxane (10 mL) was added. The mixture was stirred at room temperature for 6 hours and one hour at 60° C. with few drops of TFA. The reaction was concentrated in vacuum. The residue was purified by flash chromatography on silica gel, eluting with dichloromethane—methanol (gradient from 5% to 10% methanol) then dichloromethane—7N NH$_3$ in methanol (gradient from 20% to 50% of 7N NH$_3$ in methanol). The title compound was obtained as a white solid (875 mg, 93%).

MS (ESI$^+$) (+0.1% HCOOH): 184.18 [C$_8$H$_{13}$N$_3$S+H]$^+$ (m/z)

Step C: 8-fluoro-3-methyl-6-oxo-9-[4-(thiazol-2-ylamino)-piperidin-1-yl]-2,3-dihydro-6H-1-oxa-3,3a-diaza-phenalene-5-carboxylic acid (111)

According to general procedure A, TNOC (336 mg, 1.19 mmol, 1.0 eq.) was coupled with 34 (875 mg, 4.77 mmol, 4.0 eq.) and 1 mL of N-methylmorpholine. The residue was triturated with water and filtered (227 mg crude), an analytical sample was obtained by preparative TLC purification eluting with dichloromethane—methanol (gradient from 2.5% to 5% of methanol) to afford the title compound as a beige solid (36 mg, 7%).

HPLC (gradient 5%-80% ACN in H$_2$O): >99%
MS (ESI$^+$) (+0.1% HCOOH): 445.9 [C$_{20}$H$_{20}$FN$_5$O$_4$S+H]$^+$ (m/z)
mp=280° C.

EXAMPLE 44

8-Fluoro-9-{4-[furan-2-carbonyl)-amino]-piperidin-1-yl}-3-methyl-6-oxo-2,3-dihydro-6H-1-oxa-3,3a-diaza-phenalene-5-carboxylic acid (114)

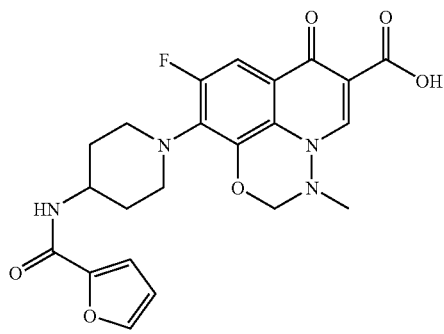

Step A: Preparation of 112

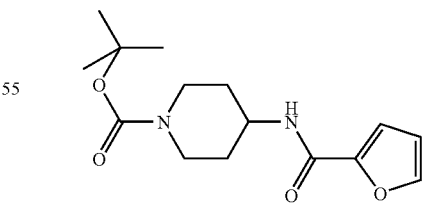

According to general procedure C, 112 was obtained with 4-amino-1-Boc-piperidine (3.7 g, 18.60 mmol, 1.0 eq.), EDCI(5.1 g, 27.88 mmol, 1.5 eq.), HOBt (3.61 g, 27.88 mmol, 1.5 eq.) and furan-2-carboxylic acid (2.5 g, 22.30 mmol, 1.2 eq.). The mixture was washed with a saturated solution of sodium bicarbonate; the residue was purified by flash chromatography on silica gel, eluting with eluting with cyclohexane-ethyl acetate (8:2 to 0:1) to afford 112 as a colorless oil (5.1 g, 97%).

Step B: Preparation of 113

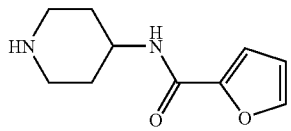

According to general procedure B, 112 (5.1 g, 17.32 mmol, 1.0 eq.) was deprotected; the residue was purified by flash chromatography on silica gel, eluting with eluting with dichloromethane—10% methanol then dichloromethane—7N $NH_3$ in methanol (gradient from 10% to 30% of 7N $NH_3$ in methanol) to afford 113 as a white foam (3.0 g, 89%).

Step C: 8-Fluoro-9-{4-[(furan-2-carbonyl)-amino]-piperidin-1-yl}-3-methyl-6-oxo-2,3-dihydro-6H-1-oxa-3,3a-diaza-phenalene-5-carboxylic acid (114)

According to general procedure A, TNOC (340 mg, 1.20 mmol, 1.0 eq.) was coupled with 37 (700 mg, 3.60 mmol, 3.0 eq.) and 1 mL of N-methylmorpholine. The residue was triturated with methanol and filtered to afford the title compound as a beige solid (175 mg, 32%).

HPLC (gradient 5%-80% ACN in $H_2O$): >90%
MS ($ESI^+$) (+0.1% HCOOH): 457.0 $[C_{22}H_{21}FN_5O_6+H]^+$ (m/z)
mp=293-295° C.

EXAMPLE 45

9-[1,4']Bipiperidinyl-1'-yl-8-fluoro-3-methyl-6-oxo-2,3-dihydro-6H-1-oxa-3,3a-diaza-phenalene-5-carboxylic acid (54g)

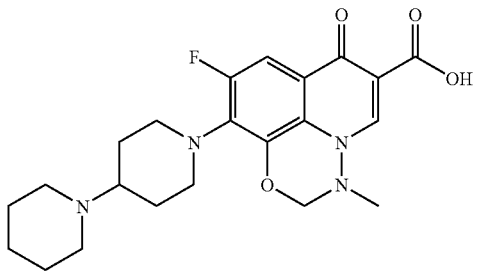

According to general procedure A, TNOC (391 mg, 1.39 mmol, 1.0 eq.) was coupled with N-(4-Piperidino)piperidine (commercially available) (700 mg, 4.16 mmol, 3.0 eq.) in 5 mL of pyridine and N-methylmorpholine (0.305 mL, 2.77 mmol, 2.0 eq.) The reaction was evaporated under reduced pressure, the residue was purified by preparative TLC purification eluting with dichloromethane—methanol (gradient from 2.5% to 10% of methanol) to afford the title compound as a yellow solid (65 mg, 11 %)

HPLC (gradient 5% to 80% ACN in $H_2O$): >99%
MS ($ESI^+$) (+0.1% HCOOH): 431.27 $[C_{22}H_{27}FN_4O_4+H]^+$ (m/z)
mp=249° C., dec.

EXAMPLE 46

8-Fluoro-3-methyl-6-oxo-9-(4-pyrrolidin-1-yl-piperidin-1-yl)-2,3-dihydro-6H-1-oxa-3,3a-diaza-phenalene-5-carboxylic acid (116)

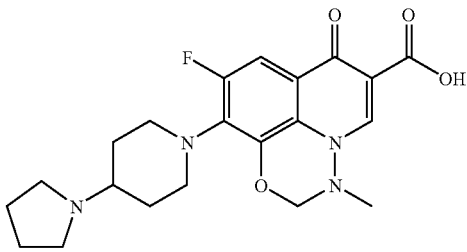

According to general procedure A, TNOC (300 mg, 1.06 mmol, 1.0 eq.) was coupled with 4-(1-pyrrolidinyl)piperidine (commercially available) (500 mg, 3.24 mmol, 3.0 eq.) in 5 mL of pyridine and 1 mL of N-methyhnorpholine. The reaction was evaporated under reduced pressure; the residue was triturated with boiling methanol to afford the title compound as a yellow solid (240 mg, 54%)

HPLC (gradient 5% to 80% ACN in $H_2O$): >99%
MS ($ESI^+$) (+0.1% HCOOH): 417.0 $[C_{21}H_{25}FN_4O_4+H]^+$ (m/z)
mp=267-269° C.

EXAMPLE 47

3-methyl-6-oxo-9-[(S)-3-(2,2,2-trifluoro-acetylamino)-pyrrolidin-1-yl]-2,3-dihydro-6H-1-oxa-3,3a-diaza-phenalene-5-carboxylic acid (117)

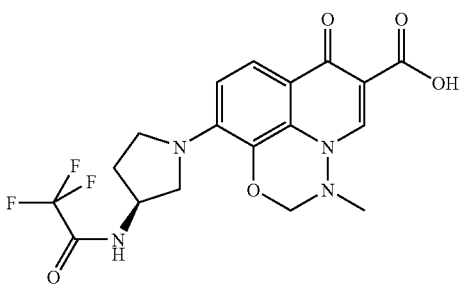

Utilizing the procedure described for the preparation of 5a, 117 was obtained from the corresponding 8-des-fluoro-9-fluoro compound (prepared according to the procedure described in U.S. Pat. No. 4,801,584) (100 mg, 0.38 mmol, 1.0 eq.) and 56e (340 mg, 1.15 mmol, 3.0 eq.) in 2.5 mL of dry pyridine and N-methylmorpholine (0.2 mL, 1.82 mmol, 4.8 eq.). The reaction was evaporated under reduced pressure. The residue was triturated with boiling methanol to afford the title compound as a yellow solid (25 mg, 15%).

HPLC (gradient 5% to 95% ACN in $H_2O$): >99%
MS ($ESI^+$) (+0.1% HCOOH): 427.05 $[C_{18}H_{17}F_3N_4O_5+H]^+$ (m/z)
mp=310° C. dec.

EXAMPLE 48

3-methyl-6-oxo-9-[(R)-3-(thiazol-2-ylamino)-pyrrolidin-1-yl]-2,3-dihydro-6H-1-oxa-3,3a-diaza-phenalene-5-carboxylic acid (118)

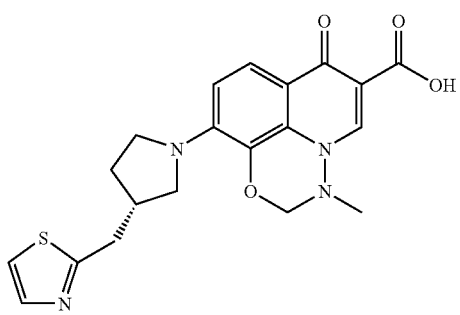

Utilizing the procedure described for the preparation of 5a, 118 was obtained from the 8-des-fluoro-9-fluoro compound (prepared according to the procedure described in US4801584) (100 mg, 0.38 mmol, 1.0 eq.) and 35b (480 mg, 1.21 mmol, 3.2 eq.) in 2.5 ml of dry pyridine and N-methylmorpholine (0.2 mL, 1.82 mmol, 4.8 eq.). The reaction was evaporated under reduced pressure. The residue was triturated with boiling methanol and purified by preparative T.L.C. to afford the title compound as a yellow solid (20 mg, 13%).

HPLC (gradient 5% to 95% ACN in $H_2O$): >99%

MS (ESI$^+$) (+0.1% HCOOH): 414.0 $[C_{19}H_{19}N_5O_4S+H]^+$ (m/z)

mp=275° C. dec.

EXAMPLE 49

9-((R)-4-amino-3,3-dimethyl-pyrrolidin-1-yl)-3-methyl-6-oxo-2,3-dihydro-6H-1-oxa-3,3a-diaza-phenalene-5-carboxylic acid

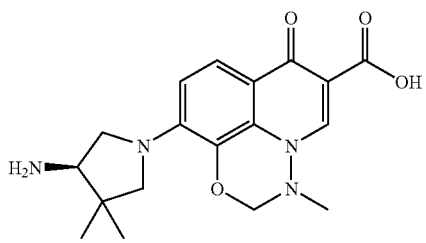

By using the preparation method of 5a, product X is obtained starting with the corresponding 8-des-fluoro-9-fluoro product (prepared according to the method described in U.S. Pat. No. 4,801,584) (80 mg, 0.30 mmol, 1.0 eq.) and from product 56e (200 mg, 1.33 mmol, 4.4 eq.) in 3 mL of anhydrous pyridine and 0.30 mL of N-methylmorpholine (2.73 mmol, 9.0 eq.). The reaction mixture is evaporated under reduced pressure and the residue is triturated in methanol, and then purified by preparative TLC. The expected product is obtained as a yellow solid (11 mg, 12%).

EXAMPLE 50

8-fluoro-2-methyl-3-methyl-6-oxo-9-[(S)-3-(2,2,2-trifluoro-acetylamino)-pyrrolidin-1-yl]-2,3-dihydro-6H-1-oxa-3,3a-diaza-phenalene-5-carboxylic acid (121)

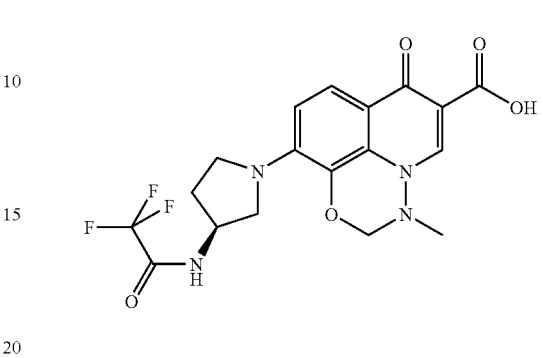

Step A: Preparation of 119

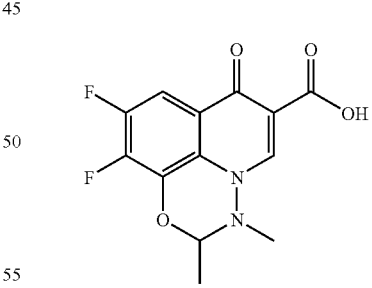

A suspension of TNOC (10.0 g, 35.43 mmol, 1.0 eq) in an aqueous solution of 5N NaOH (200 mL) was stirred at 95° C. for 6 hours. The mixture was cooled to room temperature and an aqueous solution of 6N HCl was added until precipitation. The precipitate was filtered, washed with water and diethylether and dried to afford the title compound as a white solid (9.1 g, 95%).

MS (ESI$^+$) (+0.1% HCOOH): 271.0 $[C_{11}H_8F_2N_2O_4+H]^+$ (m/z)

Step B: Preparation of 120

In a sealed tube, 119 (1.5 g, 5.55 mmol, 1.0 eq.) and acetaldehyde (40 mL, 713 mmol) were suspended in 100 mL of dry dioxane. The reaction mixture was stirred at 110° C. for 18 hours. The reaction was cooled to room temperature, the precipitate formed was filtered, washed with methanol and diethylether, and dried to afford the title compound as a white solid (1.1 g, 69%).

HPLC (gradient 5% to 95% ACN in $H_2O$): >99%

MS (ESI$^+$) (+0.1% HCOOH): 297.0 $[C_{13}H_{10}F_2N_2O_4+H]^+$ (m/z)

Step C: 8-fluoro-2-methyl-3-methyl-6-oxo-9-[(S)-3-(2,2,2-trifluoro-acetylamino)-pyrrolidin-1-yl]-2,3-dihydro-6H-1-oxa-3,3a-diaza-phenalene-5-carboxylic acid (121)

Utilizing the procedure described for the preparation of 5a, 121 was obtained from 120 (100 mg, 0.34 mmol, 1.0 eq.) and 56e (300 mg, 1.01 mmol, 3.0 eq.) in 2 mL of dry pyridine and N-methylmorpholine (0.2 mL, 1.82 mmol, 5.0 eq.). The reaction was evaporated under reduced pressure. The residue was recrystallized in methanol to afford the title compound as a yellow solid (54 mg, 35%).

HPLC (gradient 5% to 95% ACN in $H_2O$): >99%

MS (ESI$^+$) (+0.1% HCOOH): 459.3 $[C_{19}H_{18}F_4N_4O_5+H]^+$ (m/z)

mp=242° C.-245° C.

EXAMPLE 51

8-fluoro-2,2-methyl-3-methyl-6-oxo-9-[(S)-3-(2,2,2-trifluoro-acetylamino)-pyrrolidin-1-yl]-2,3-dihydro-6H-1-oxa-3,3a-diaza-phenalene-5-carboxylic acid (123)

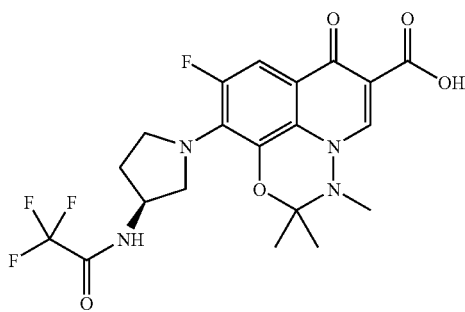

Step A: Preparation of 122

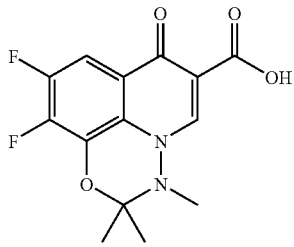

Utilizing the procedure described for the preparation of 120, 122 was obtained from 119 (500 mg, 1.85 mmol, 1.0 eq.) and dry acetone (6.2 mL, 89 mmol) in 20 mL of dry dioxane. The reaction was evaporated under reduced pressure. The residue was triturated with boiling methanol to afford the title compound as a white solid (610 mg, 100%).

HPLC (gradient 5% to 95% ACN in $H_2O$): >99%

MS (ESI$^+$) (+0.1% HCOOH): 311.1 $[C_{14}H_{12}F_2N_2O_4+H]^+$ (m/z)

Step B: 8-fluoro-2,2-methyl-3-methyl-6-oxo-9-[(S)-3-(2,2,2-trifluoro-acetylamino)-pyrrolidin-1yl]-2,3-dihydro-6H-1-oxa-3,3a-diaza-phenalene-5-carboxylic acid (123)

Utilizing the procedure described for the preparation of 5a, 123 was obtained from 122 (100 mg, 0.32 mmol, 1.0 eq.) and 56e (280 mg, 0.96 mmol, 3.0 eq.) in 2 mL of dry pyridine and N-methylmorpholi (0.2 mL, 1.82 mmol, 5.0 eq.). The reaction was evaporated under reduced pressure. The residue was purified by preparative T.L.C. and triturated in diethylether to afford the title compound as a yellow solid (35 mg, 23%).

HPLC (gradient 5% to 95% ACN in $H_2O$): >95%

MS (ESI$^+$) (+0.1% HCOOH): 473.2 $[C_{20}H_{20}F_4N_4O_5+H]^+$ (m/z)

mp=217° C.-219° C.

EXAMPLE 52

2-methyl-3-methyl-6-oxo-9-[(S)-3-(2,2,2-trifluoro-acetylamino)-pyrrolidin-1-yl]-2,3-dihydro-6H-1-oxa-3,3a-diaza-phenalene-5-carboxylic acid (126)

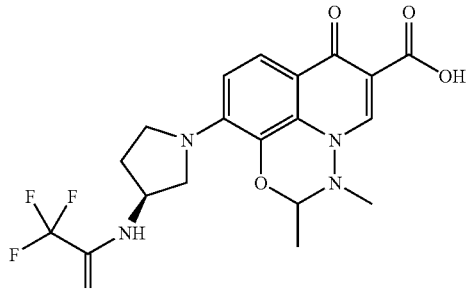

Step A: Preparation of 124

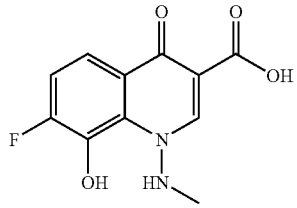

Compound 124 was prepared according to the procedure described in U.S. Pat. No. 4,801,584.

Step B: Preparation of 125

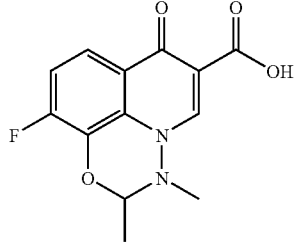

Utilizing the procedure described for the preparation of 120, 125 was obtained from 124 (400 mg, 1.43 mmol, 1.0 eq.) and acetaldehyde (12.0 mL, 214 mmol) in 30 mL of dry dioxane. The reaction was evaporated under reduced pressure. The residue was triturated with boiling methanol to afford the title compound as a brown solid (305 mg, 77%).

HPLC (gradient 5% to 95% ACN in H$_2$O): >90%

MS (ESI$^+$) (+0.1% HCOOH): 279.0 [C$_{13}$H$_{11}$FN$_2$O$_4$+H]$^+$ (m/z)

Step C: 2-methyl-3-methyl-6-oxo-9-[(S)-3-(2,2,2-trifluoro-acetylamino)-pyrrolidin-1-yl]-2,3-dihydro-6H-1-oxa-3,3a-diaza-phenalene-5-carboxylic acid (126)

Utilizing the procedure described for the preparation of 5a, 126 was obtained from 125 (100 mg, 0.36 mmol, 1.0 eq.) and 56e (210 mg, 1.05 mmol, 2.9 eq.) in 2 mL of dry pyridine and N-methylmorpholine (0.2 mL, 1.82 mmol, 5.0 eq.). The reaction was evaporated under reduced pressure. The residue was triturated in diethylether and purified by T.L.C. preparative to afford the title compound as a yellow solid (21 mg, 13%).

HPLC (gradient 5% to 95% ACN in H$_2$O): >99%

MS (ESI$^+$) (+0.1% HCOOH): 441.2 [C$_{19}$H$_{19}$F$_3$N$_4$O$_5$+H]$^+$ (m/z)

Mp=260° C.

EXAMPLE 53

2,2-methyl-3-methyl-6-oxo-9-[(S)-3-(2,2,2-trifluoro-acetylamino)-pyrrolidin-1-yl]-2,3-dihydro-6H-1-oxa-3,3a-diaza-phenalene-5-carboxylic acid (128)

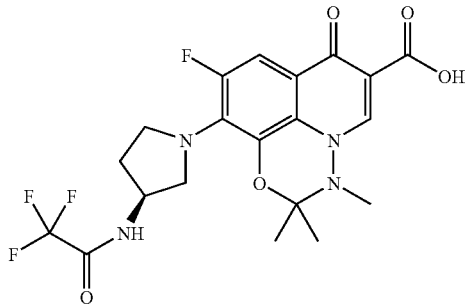

Step A: Preparation of 127

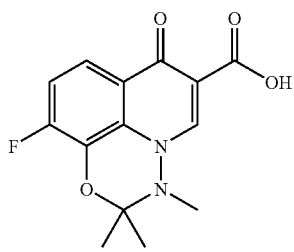

Utilizing the procedure described for the preparation of 120, 127 was obtained from 124 (400 mg, 1.43 mmol, 1.0 eq.) and dry acetone (4.0 mL, 57.3 mmol) in 13 mL of dry dioxane. The reaction was evaporated under reduced pressure. The residue was triturated with boiling methanol to afford the title compound as a brown solid (338 mg, 70%).

HPLC (gradient 5% to 95% ACN in H$_2$O): >99%

MS (ESI$^+$) (+0.1% HCOOH): 293.1 [C$_{14}$H$_{13}$FN$_2$O$_4$+H]$^+$ (m/z)

Step B: 2,2-methyl-3-methyl-6-oxo-9-[(S)-3-(2,2,2-trifluoro-acetylamino)-pyrrolidin-1-yl]-2,3-dihydro-6H-1-oxa-3,3a-diaza-phenalene-5-carboxylic acid (128)

Utilizing the procedure described for the preparation of 5a, 128 was obtained from 127 (110 mg, 0.38 mmol, 1.0 eq.) and 56e (340 mg, 1.15 mmol, 3.0 eq.) in 2 mL of dry pyridine and N-methylmorpholine (0.2 mL, 1.82 mmol, 5.0 eq.). The reaction was evaporated under reduced pressure. The residue was triturated in methanol and purified by preparative T.L.C. to afford the title compound as a yellow solid (20 mg, 12%).

HPLC (gradient 5% to 95% ACN in H$_2$O): >95%

MS (ESI$^+$) (+0.1% HCOOH): 455.1 [C$_{20}$H$_{21}$F$_3$N$_4$O$_5$+H]$^+$ (m/z)

mp=283° C.

EXAMPLE 54

8-fluoro-2-methyl-3-methyl-6-oxo-9-[(R)-3-(thiazol-2-ylamino)-pyrrolidin-1-yl]-2,3-dihydro-6H-1-oxa-3,3a-diaza-phenalene-5-carboxylic acid (129)

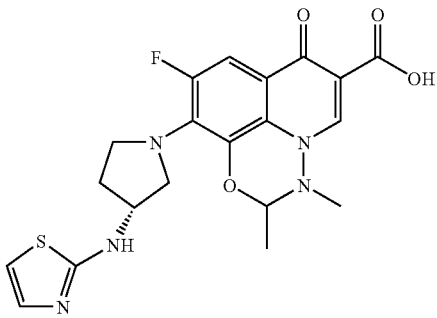

Utilizing the procedure described for the preparation of 5a, 129 was obtained from 120 (300 mg, mmol, 1.0 eq.) and 35b (620 mg, 3.03 mmol, 3.0 eq.) in 6 mL of dry pyridine and N-methylmorpholine (0.6 mL, 5.05 mmol, 5.0 eq.). The reaction was evaporated under reduced pressure. The residue was purified by flash chromatography on silica gel, eluting with dichloromethane—methanol (gradient from 0% to 5% methanol) to afford the title compound as a yellow solid (50 mg, 15%).

HPLC (gradient 5% to 95% ACN in H$_2$O): >99%

MS (ESI$^+$) (+0.1% HCOOH): 446.0 [C$_{20}$H$_{20}$FN$_5$O$_4$+H]$^+$ (m/z)

mp=224° C.-226° C.

EXAMPLE 55

8-fluoro-2,2,3-trimethyl-6-oxo-9-[(R)-3-(thiazol-2ylamino)-pyrrolidin-1-yl]-2,3-dihydro-6H-1-oxa-3,3a-diaza-phenalene-5-carboxylic acid (130)

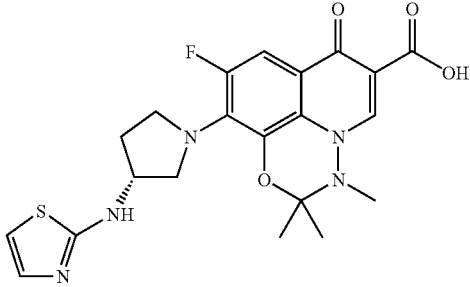

By using the method for preparing 5a, the product 130 is obtained starting with 200 mg of product 112 (0.64 mmol, 1.0 eq.) and product 35b (770 mg, 1.93 mmol, 3.0 eq.) in 4 mL of anhydrous pyridine and 0.35 mL of N-methylmorpholine (3.20 mmol, 5.0 eq.). The reaction medium is evaporated under reduced pressure and the residue is purified by chromatography on silica and then by preparative TLC. The expected product is obtained as a yellow solid (8 mg, 3%).

HPLC (5%-95% ACN gradient in $H_2O$); >90%

MS ($ESI^+$) (+0.1%, HCOOH): 460.10 $[C_{21}H_{22}FN_5O_4S+H]^+$ (m/z)

MP=235-237° C.

EXAMPLE 56

2,3-dimethyl-6-oxo-R-[(R)-3-(thiazol-2-ylamino)-pyrrolidin-1-yl]-2,3-dihydro-6H-1-oxa-3,3a-diaza-phenalene-5-carboxylic acid (131)

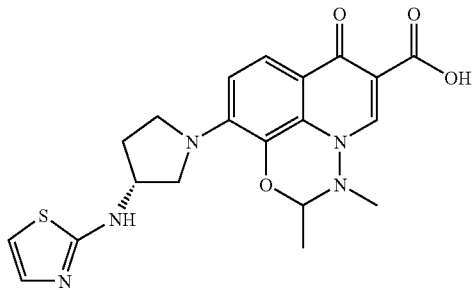

By using the method for preparing 5a, the product 131 is obtained starting with 190 mg of product 125 (0.36 mmol, 1.0 eq.) and with product 35b (860 mg, 2.16 mmole, 3.2 eq.) in 5 mL of anhydrous pyridine and 0.5 mL of N-methylmorpholine (4.55 mmol, 6.7 eq.). The reaction mixture is evaporated under reduced pressure and the residue is triturated in ethyl ether and then purified by chromatography on silica by eluting with a dichloromethane-methanol mixture (100:0 to 96:4) and the expected product is obtained as a yellow solid (20 mg, 7%).

HPLC (5%-95% ACN gradient in $H_2O$); >99%

MS ($ESI^+$) (+0.1%, HCOOH): 428.0 $[C_{20}H_{21}N_5O_4S+H]^+$ (m/z)

MP=260-263° C.

EXAMPLE 57

2,2,3-trimethyl-6-oxo-9-[(R)-3-(thiazol-2-ylamino)-pyrrolidin-1-yl]-2,3-dihydro-6H-1-oxa-3,3a-diaza-phenalene-5-carboxylic acid (132)

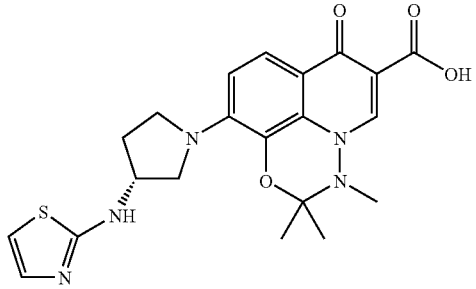

By using the method for preparing 5a, the product 132 is obtained starting with 200 mg of product 127 (0.68 mmol, 1.0 eq.) and of product 35b (870 mg, 2.19 mmol, 3.2 eq.) in 5 mL of anhydrous pyridine and 0.5 mL of N-methylmorpholine (4.55 mmol, 6.7 eq.). The reaction medium is evaporated under reduced pressure and the residue is triturated in methanol and then purified by preparative TLC. The expected product is obtained as a yellow solid (21 mg, 7%).

HPLC (5%-95% ACN gradient in $H_2O$); >99%

MS ($ESI^+$) (+0.1%, HCOOH): 442.0 $[C_{21}H_{23}N_5O_4S+H]^+$ (m/z)

MP=287° C. (decomposition).

EXAMPLE 58

2,2,3-dimethyl-6-oxo-R-[(R)-3-(thiazol-2-ylamino)-pyrrolidin-1-yl]-2,3-dihydro-6H-1-oxa-3,3a-diaza-phenalene-5-carboxylic acid (134)

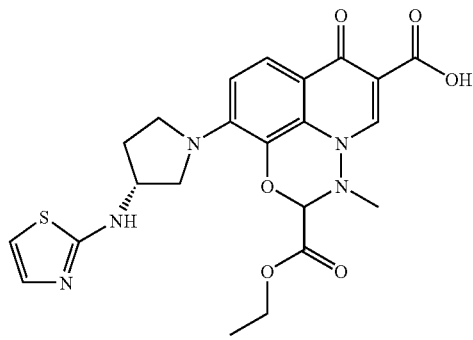

Stage A: Preparation of 133

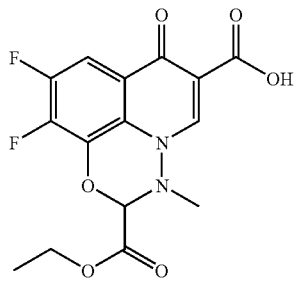

By using the method for preparing 120, the product 133 is obtained starting with 2.0 g of product 119 (7.40 mmol, 1.0 eq.), with 6.6 mL of ethyl diethoxy acetate (89 mmol) and 0.5 mL of trifluoroacetic acid (6.70 mmol, 0.9 eq.) in 80 mL of anhydrous dioxane. The expected product is obtained as a white solid (2.0 g, 76%).

HPLC (5%-95% ACN gradient in $H_2O$); >85%

MS ($ESI^+$) (+0.1%, HCOOH): 355.1 $[C_{15}H_{12}F_2N_2O_6+H]^+$ (m/z)

Stage B: 2,2,3-trimethyl-6-oxo-9-[(R)-3-(thiazol-2-yl-amino)-pyrrolidin-1-yl]-2,3-dihydro-6H-1-oxa-3,3a-diaza-phenalene-5-carboxylic acid By using the method for preparing 5a, the product 134 is obtained starting with 300 mg of product 133 (0.84 mmol, 1.0 eq.) and with product 35b (720 mg, 2.42 mmol, 3.0 eq.) in 6 mL of anhydrous pyridine and 0.45 mL of N-methylmorpholine (4.20 mmol, 5.0 eq.). The reaction medium is evaporated under reduced pressure and the residue is triturated in methanol and then purified by preparative TLC. The expected product is obtained as a white solid (13 mg, 3%).

HPLC (5%-95% ACN gradient in $H_2O$); >95%

MS (ESI$^+$) (+0.1%, HCOOH): 504.05 $[C_{22}H_{22}FN_5O_6S+H]^+$ (m/z)

MP=287° C.

EXAMPLE 59

9-[(R)-4-amino-3,3-dimethyl-pyrrolidin-1-yl]-8-fluoro-2,3-dimethyl-6-oxo-2,3-dihydro-6H-1-oxa-3,3a-diaza-phenalene-5-carboxylic acid (135)

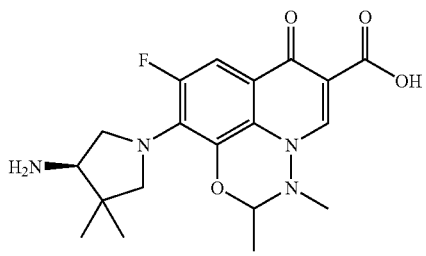

By using the method for preparing 5a, the product 135 is obtained starting with the product 120 (230 mg, 0.78 mmol, 1.0 eq.) and of product 74b (200 mg, 1.33 mmol, 1.7 eq.) in 1 mL of anhydrous pyridine and 2 mL of anhydrous acetonitrile in the presence of DABCO (250 mg, 2.23 mmol, 2.9 eq.). The reaction medium is filtered and the precipitate is washed with acetonitrile. The obtained solid is triturated in methanol and washed with methanol and then with ethyl ether. The expected product is obtained as a yellow solid (105 mg, 34%).

HPLC (5%-95% ACN gradient in $H_2O$); >90%

MS (ESI$^+$) (+0.1%, HCOOH): 391.0 $[C_{19}H_{23}FN_4O_4+H]^+$ (m/z)

MP=212-214° C.

EXAMPLE 60

9-((R)-4-amino-3,3-dimethyl-pyrrolidin-1-yl)-8-fluoro-2,2,3-trimethyl-6-oxo-2,3-dihydro-6H-1-oxa-3,3a-diaza-phenalene-5-carboxylic acid (136)

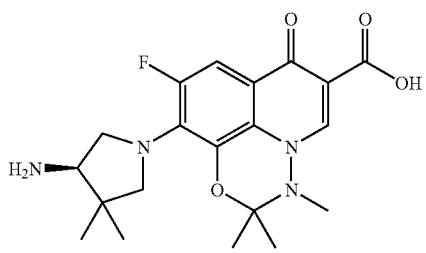

By using the method for preparing 5a, the product 136 is obtained starting with the 220 mg of product 112 (0.71 mmol, 1.0 eq.) and of product 74b (200 mg, 1.33 mmol, 1.9 eq.) in 4 mL of anhydrous pyridine and 2 mL of anhydrous acetonitrile in the presence of DABCO (250 mg, 2.23 mmol, 3.1 eq.). The reaction medium is filtered and the precipitate is washed with acetonitrile. The obtained solid is triturated in methanol and washed with methanol and then with ethyl ether. The expected product is obtained as a yellow solid (110 mg, 38%).

HPLC (5%-95% ACN gradient in $H_2O$); >90%

MS (ESI$^+$) (+0.1%, HCOOH): 405.0 $[C_{20}H_{25}FN_4O_4+H]^+$ (m/z)

MP=255-257° C.

EXAMPLE 61

9-[(S)-3,3-dimethyl-4-(thiazol-2-ylamino)-pyrrolidin-1-yl]-8-fluoro-3-methyl-6-oxo-2,3-dihydro-6H-1-oxa-3,3a-diaza-phenalene-5-carboxylic acid (141)

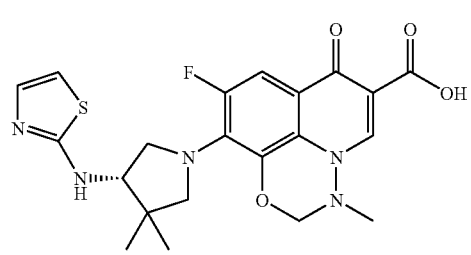

Stage A: Preparation of 137

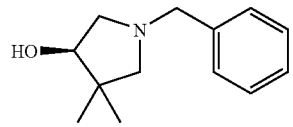

137 was prepared according to the method described by Di Cesare et al., J. Med. Chem. 1992, 35, (22), 4205-13, by using (S)-pentolactone as starting material.

Stage B: Preparation of 138

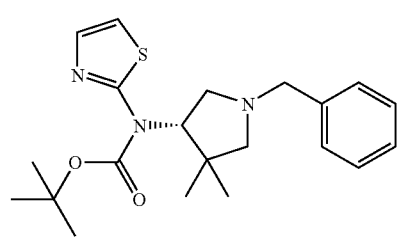

The compound 138 is obtained by following the method described in the preparation of product 8a by substituting the product 137 for the product 6. The obtained raw product is purified by chromatography on silica by eluting with a dichloromethane-methanol mixture (10:0 to 9:1) and the product 138 is obtained as a brown foam (385 mg, 25%).

Stage C: Preparation of 139

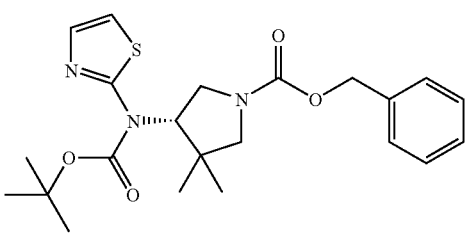

The product 138 (380 mg, 0.98 mmol, 1.0 eq.) is dissolved in 5 mL of anhydrous chloroform and 0.28 mL of benzylchloroformate (1.99 mmol, 2.0 eq.) are added. The mixture is stirred at 60° C. for 8 hours. The reaction medium is diluted with dichloromethane and washed with a saturated sodium hydrogencarbonate solution. The isolated organic extracts are dried and the solvent is evaporated under reduced pressure. The raw expected product is obtained, which is purified by chromatography on silica by diluting with a cyclohexane-ethyl acetate mixture (10:0 to 9:1) and the expected product 139 is obtained as pale yellow oil (307 mg, 70%).

Stage D: Preparation of 140

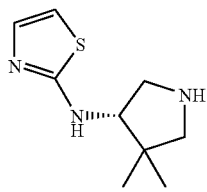

The product 139 (300 mg, 0.70 mmol, 1.0 eq.) and sodium iodide (420 mg, 2.80 mmol, 4.0 eq.) are dissolved in 5 mL of anhydrous acetonitrile. 0.35 mL of chlorotrimethyl silane (2.77 mmol, 4.0 eq.) are then added dropwise. The mixture is stirred at room temperature for 4 hours. The reaction medium is diluted with 5 mL of methanol and then the solvent is evaporated under reduced pressure. The raw expected product is obtained, which is purified by chromatography on silica by eluting with a dichloromethane-methanol mixture (10:0 to 9:1) subsequently with a SCX column and the expected product 140 is obtained as a brown oil (85 mg, 61%).

Stage E: 9-[(S)-3,3-dimethyl-4-(thiazol-2-ylamino)-pyrrolidin-1-yl]-8-fluoro-3-methyl-6-oxo-2,3-dihydro-6H-1-oxa-3,3a-diaza-phenalene-5-carboxylic acid By using the method for preparing 5a, the product 141 is obtained starting with 65 mg of "UBE-4" (0.23 mmol, 1.0 eq.) and with the product 140 (80 mg, 0.41 mmol, 2.0 eq.) in 0.5 mL of anhydrous pyridine and 1 mL of acetonitrile in the presence of DABCO (50 mg, 0.45 mmol, 2.0 eq.). The reaction medium is filtered and the precipitate washed with acetonitrile. The obtained solid is triturated in methanol and washed with methanol and then with ethyl ether. The expected product is obtained as a yellow solid (23 mg, 22%).

HPLC (5%-95% ACN gradient in $H_2O$); >95%

MS (ESI$^+$) (+0.1%, HCOOH): 460.5 [$C_{21}H_{22}FN_5O_4S$+ H]$^+$ (m/z)

MP=265° C. (decomposition).

EXAMPLE 62

9-[(R)-3,3-dimethyl-4-(thiazol-2-ylamino)-pyrrolidin-1-yl]-8-fluoro-3-methyl-6-oxo-2,3-dihydro-6H-1-oxa-3,3a-diaza-phenalene-5-carboxylic acid (146)

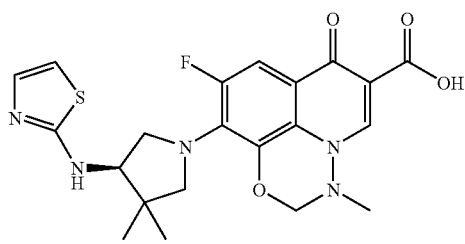

Stage A: Preparation of 142

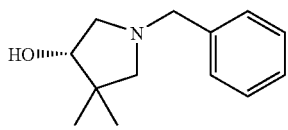

142 was prepared according to the method described by Di Cesare et al., J. Med. Chem. 1992, 35, (22), 4205-13, by using (R)-pantolactone as starting material.

Stage B: Preparation of 143

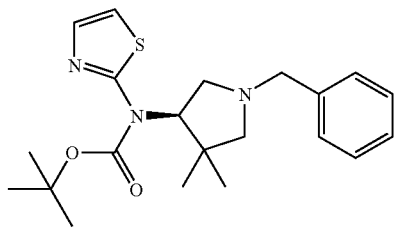

Compound 143 is obtained by following the method described in the preparation of 8a by substituting product 142 for product 6. The obtained raw product is purified by chromatography on silica by eluting with a dichloromethane-methanol mixture (10:0 to 93:7) and product 143 is obtained as a yellow oil (865 mg, 22%).

Stage C: Preparation of 144

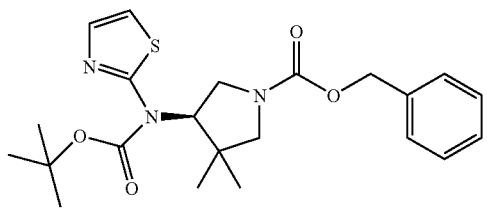

By using the method for preparing 139, product 144 is obtained with the starting product 143 (860 mg, 1.13 mmol, 1.0 eq.). The expected raw product is obtained, which is purified by chromatography on silica by eluting with a cyclohexane-ethyl acetate mixture (10:0 to 9:1) and the expected product is obtained as a colorless oil (445 mg, 91%).

Stage D: Preparation of 145

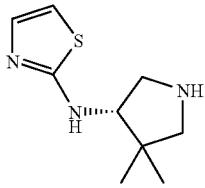

By using the method for preparing 140, product 145 is obtained with the starting product 144 (420 mg, 0.97 mmol, 1.0 eq.). The raw expected product is obtained, which is purified by chromatography on silica by eluting with a dichloromethane-methanol mixture (10:0 to 9:1), subsequently with a SCX column and the product 140 is obtained as colorless oil (165 mg, 86%).

Stage E: 9-[(R)-3,3-dimethyl-4-(thiazol-2-ylamino)-pyrrolidin-1-yl]-8-fluoro-3-methyl-6-oxo-2,3-dihydro-6H-1-oxa-3,3a-diaza-phenalene-5-carboxylic acid By using the method for preparing 5a, product 146 is obtained starting with 115 mg of "UBE-4" (0.41 mmol, 1.0 eq.) and with product 145 (160 mg, 0.81 mmol, 2.0 eq.) in 1 mL of anhydrous pyridine and 2 mL of acetonitrile in the presence of DABCO (90 mg, 0.80 mmol, 2.0 eq.). The reaction medium is filtered and the precipitate washed with acetonitrile. The obtained solid is triturated in methanol and washed with methanol and then with ethyl ether. The expected product is obtained as a yellow solid (67 mg, 36%).

HPLC (5%-95% ACN gradient in $H_2O$); >95%

MS (ESI+) (+0.1%, HCOOH): 460.53 [$C_{21}H_{22}FN_5O_4S$+H]+ (m/z)

MP=271-273° C.

EXAMPLE 63

8-fluoro-3-methyl-6-oxo-9-((R)-3-[1,2,3]triazol-1-yl-pyrrolidin-1-yl)-2,3-dihydro-6H-1-oxa-3,3a-diaza-phenalene-5-carboxylic acid (149)

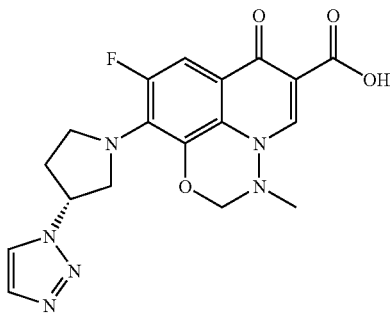

Stage A: Preparation of 147

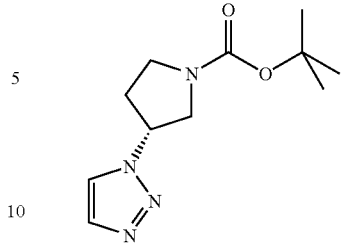

The product is prepared according to the method described in US 2003/0225107 by substituting the 3-(S)-azido-pyrrolidin-1-yl carbamic acid tert-butyl ester for the 5(R)-azidomethyl-3-[4-(1-cyanocyclopropan-1-yl)phenyl]oxazolidin-2-one (1.1 g, 5.20 mmol, 1.0 eq.). The raw product is purified by chromatography on silica by eluting with a dichloromethane-methanol mixture (100:0 to 97:3) and 142 is obtained as an orange oil (681 mg, 55%).

Stage B: Preparation of 148

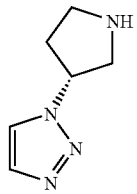

The method described for preparing 4c is used by substituting product 147 (680 mg, 2.85 mmol, 1.0 eq.) for product 3c with 17 mL of HCl 4N in dioxane. The obtained raw product is subsequently used without any subsequent purification.

Stage C: 8-fluoro-3-methyl-6-oxo-9-((R)-3-[1,2,3]triazol-1-yl-pyrrolidin-1-yl)-2,3-dihydro-6H-1-oxa-3,3a-diaza-phenalene-5-carboxylic acid

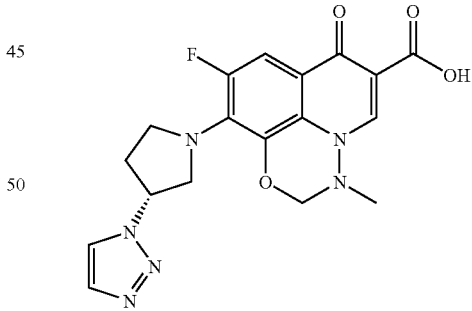

The method described in preparation 5c is used by substituting product 148 (400 mg, 2.30 mmol, 4.0 eq.) for product 4c. The reaction medium is evaporated under reduced pressure. The result is triturated in methanol and then purified by preparative TLC. The expected product is obtained as a yellow solid (20 mg, 22%).

HPLC (5%-95% ACN gradient in $H_2O$); >95%

MS (ESI+) (+0.1%, HCOOH): 401.4 [$C_{18}H_{17}FN_6O_4$+H]+ (m/z)

MP=235° C. (decomposition).

EXAMPLE 64

8-fluoro-3-methyl-6-oxo-9-((S)-3-[1,2,3]triazol-1-yl-pyrrolidin-1-yl)-2,3-dihydro-6H-1-oxa-3,3a-diaza-phenalene-5-carboxylic acid (152)

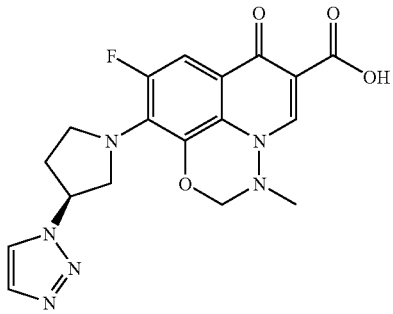

Stage A: Preparation of 150

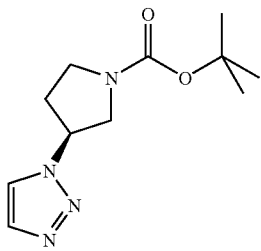

The product is prepared according the method described in US 2003/0225107 by substituting 3(R)-azido-pyrrolidin-1-yl carbamic acid tert butyl ester for 5(R)-azidomethyl-3-[4-(1-cyanocyclopropan-1-yl)-phenyl]oxazolidin-2-one (1.1 g, 5.2 mmol, 1.0 eq.). The raw product is subsequently used without any subsequent purification (550 mg, 44%).

Stage B: Preparation of 151

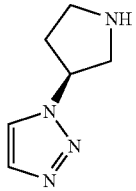

The method described for preparing 4c is used by substituting product 150 (550 mg, 2.30 mmol, 1.0 eq.) for product 3c with 14 ml of HCl 4N in dioxane. The raw product subsequently used without any subsequent purification.

Stage C: 8-fluoro-3-methyl-6-oxo-9-((S)-3-[1,2,3]triazol-1-yl-pyrrolidin-1-yl)-2,3-dihydro-6H-1-oxa-3,3a-diaza-phenalene-5-carboxylic acid

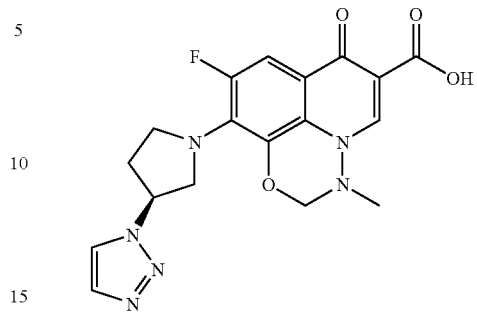

The method described in preparation 5c is used by substituting product 151 (400 mg, 2.30 mmol, 4.0 eq.) for product 4c. The reaction medium is evaporated under reduced pressure. The result is triturated in methanol and then purified by preparative TLC. The expected product is obtained as a yellow solid (30 mg, 33%).

HPLC (5%-95% ACN gradient in $H_2O$); >90%

MS (ESI$^+$) (+0.1%, HCOOH): 401.4 $[C_{18}H_{17}FN_6O_4+H]^+$ (m/z)

MP=235° C. (decomposition).

EXAMPLE 65

8-fluoro-3-methyl-9-[(R)-3-(3-methyl-isoxazol-5-ylamino)-pyrrolidin-1-yl]-6-oxo-2,3-dihydro-6H-1-oxa-3,3a-diaza-phenalene-5-carboxylic acid (155)

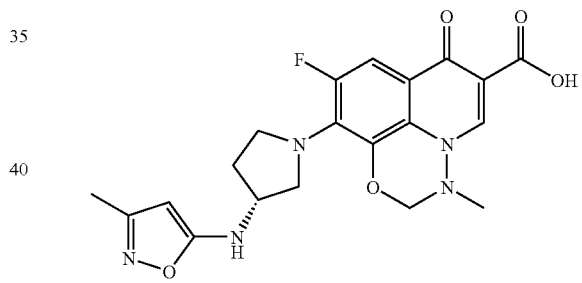

Stage A: Preparation of 153

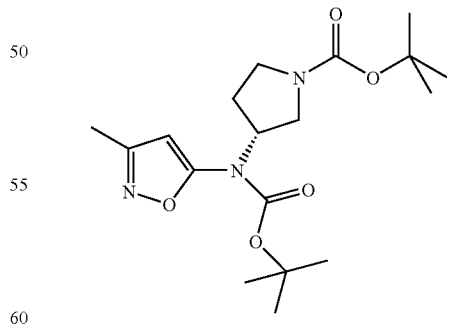

The method described for preparing product 8a is used by substituting 3-(S)-hydroxy-pyrrolidine-1-carboxylic acid tert-butyl ester (1.0 g, 5.34 mmol, 1.2 eq.) for 3-hydroxy-pyrrolidine-1-carboxylic acid tert-butyl ester, and 5-methyl-isoxazol-3-yl carbamic acid tert-butyl ester (880mg, 4.4mmol, 1.0 eq.) for product 7a. The raw product is purified by chromatography on silica by eluting with a cyclohexane-ethyl acetate mixture (1:0 to 8:2) and product 148 is obtained as a pale pink oil (760 mg, 43%).

Stage B: Preparation of 154

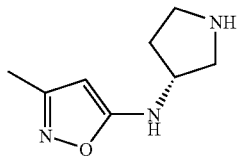

The method described for preparing product 4a is used by substituting product 153 (720 mg, 1.96 mmol, 1.0 eq.) for product 3a with 2 mL of trifluoroacetic acid in 20 mL of dichloromethane. The residue is purified by chromatography on silica by eluting with a dichloromethane-NH$_3$ 7N mixture in methanol (0%-10% 7N NH$_3$ gradient in methanol. The expected product is obtained as a brown oil (53 mg, 16%).

Stage C: 8-fluoro-3-methyl-9-[(R)-3-(3-methyl-isoxazol-5-ylamino)-pyrrolidin-1-yl]-6-oxo-dihydro-6H-1-oxa-3,3a-diaza-phenalene-5-carboxylic acid By using the method for preparing 5a, product 155 is obtained starting with 50 mg of <<UBE-4>> (0.18 mmol, 1.0 eq.) and with product 154 (50 mg, 0.30 mmol, 1.7 eq.) in 0.5 mL of anhydrous pyridine and 1 mL of anhydrous acetonitrile in the presence of DABCO (50 mg, 0.45 mmol, 2.5 eq.). The reaction medium is evaporated and the obtained solid is triturated in methanol and washed with methanol and then with ethyl ether. The expected product is obtained as a yellow solid (53 mg, 68%).

HPLC (5%-95% ACN gradient in H$_2$O); >95%

MS (ESI$^+$) (+0.1%, HCOOH): 430.5 [C$_{20}$H$_{20}$FN$_5$O$_5$+H]$^+$ (m/z)

MP=255-257° C.

EXAMPLE 66

8-fluoro-3-methyl-9-[(S)-3-(3-methyl-isoxazol-5-ylamino)-pyrrolidin-1-yl]-6-oxo-2,3-dihydro-6H-1-oxa-3,3a-diaza-phenalene-5-carboxylic acid (158)

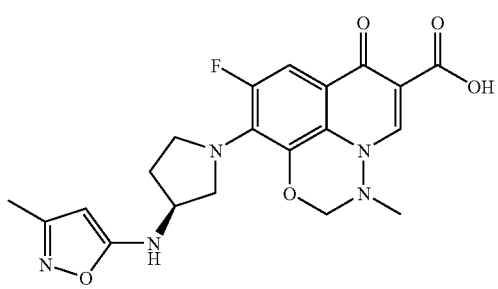

Stage A: Preparation of 156

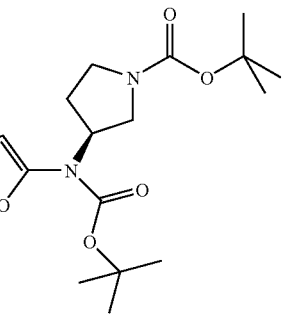

The method described for preparing 8a is used, by substituting 3-(R)-hydroxy-pyrrolidine-1-carboxylic acid tert-butyl ester (1.04 g, 5.34 mmol, 1.2 eq.) for 3-hydroxy-pyrrolidine-1-carboxylic acid tert-butyl ester, and 5-methyl-isoxazol-3-yl carbarnic acid tert-butyl ester for product 7a (880 mg, 4.4 mmol, 1.0 eq.). The raw product is purified by chromatography on silica by eluting with a cyclohexane-ethyl acetate mixture (1:0 to 8:2) and product 151 is obtained as a colorless oil (840 mg, 46%).

Stage B: Preparation of 157

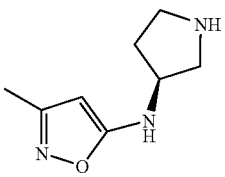

The method described for preparing product 4a is used, by substituting product 156 (800 mg, 2.18 mmol, 1.0 eq.) for product 3a with 2 mL of trifluoroacetic acid in 20 mL of dichloromethane. The residue is purified by chromatography on silica by eluting with a 7N dichloromethane-NH$_3$ mixture in methanol (0%-10% 7N NH$_3$ gradient in methanol). The expected product is obtained as a brown oil (178 mg, 49%).

Stage C: 8-fluoro-3-methyl-9-[(S)-3-(3-methyl-isoxazol-5-ylamino)-pyrrolidin-1-yl]-6-oxa-2,3-dihydro-6H-1-oxa-3,3a-diaza-phenalene-5-carboxylic acid By using the method for preparing 5a, product 158 is obtained starting with 150 mg of "UBE-4" (0.53 mmol, 1.0 eq.) and with product 157 (170 mg, 1.02 mmol, 1.9 eq.) in 1 mL of anhydrous pyridine and 2 mL of anhydrous acetonitrile in the presence of DABCO (150 mg, 1.34 mmol, 2.5 eq.). The reaction medium is evaporated and the obtained solid is triturated in methanol and washed with methanol and then with ethyl ether. The expected product is obtained as a yellow solid (182 mg, 78%).

HPLC (5%-95% ACN gradient in H$_2$O); >95%

MS (ESI$^+$) (+0.1%, HCOOH): 430.4 [C$_{20}$H$_{20}$FN$_5$O$_5$+H]$^+$ (m/z)

MP=255-257° C.

EXAMPLE 67

8-fluoro-9-[(S)-3-(1H-imidazol-2-ylamino)-pyrrolidin-1-yl]-3-methyl-6-oxo-2,3-dihydro-6H-1-oxa-3,3a-diaza-phenalene-5carboxylic acid (163)

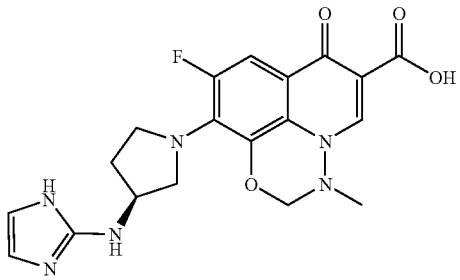

Stage A: Preparation of 159

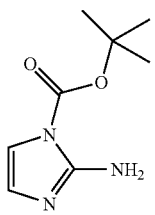

To a solution of 2-amino-imidazole sulfate (10.0 g, 37.84 mmol, 1.0 eq.) in 100 mL of an aqueous (1N) sodium hydroxide solution, is added a solution of di-tert-butyl dicarbonate (16.5 g, 75.60 mmol, 2.0 eq.) in 100 mL of dichloromethane. The mixture is stirred at room temperature for 16 hours. The organic phase is then isolated by decantation and then washed with water, dried and then concentrated under reduced pressure. The product obtained as a pink solid (11.2 g, quantitative) is used without any subsequent purification.

Stage B: Preparation of 160

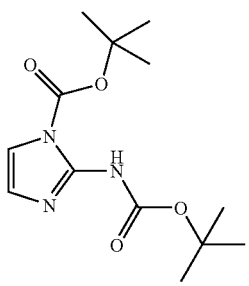

By using the method for preparing 7a, product 160 is obtained starting with 159 (11.2 g, 37.84 mmol, 1.0 eq.). The raw expected product is obtained, which is purified by chromatography on silica by eluting with a cyclohexane-ethyl acetate mixture (10:0 to 4:6) and the expected product 160 is obtained as a yellow solid (3.7 g, 35%).

Stage C: Preparation of 161

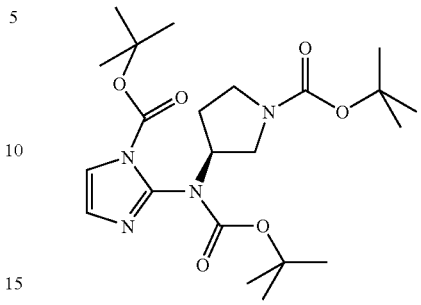

The method described for preparing 8a is used, by substituting 3-(R)-hydroxy-pyrrolidine-1-carboxylic acid tert-butyl ester (545 mg, 2.91 mmol, 1.5 eq.) for 3-hydroxy-pyrrolidine-1-carboxylic acid tert-butyl ester, and product 160 (550 mg, 1.94 mmol, 1.0 eq.) for product 7a. The raw product is purified by chromatography on silica by eluting with a cyclohexane-ethyl acetate mixture (1:0 to 7:3) and product 161 is obtained as a colorless oil (455 mg, 52%).

Stage D: Preparation of 162

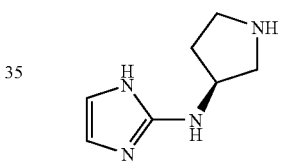

The method described for preparing the product 4a is used, by substituting product 161 (450 mg, 0.99 mmol, 1.0 eq.) for product 3a with 0.8 mL of trifluoroacetic acid in 10 mL of dichloromethane. The medium is co-evaporated with methanol and then triturated in ethyl ether. The expected product is obtained as a white powder (325 mg, 66%).

Stage E: 8-fluoro-9-[(S)-3-(1H-imidazol-2-ylamino)-pyrrolidin-1-yl]-3-methyl-6-oxo-2,3-dihydro-6H-1-oxa-3,3a-diaza-phenalene-5-carboxylic acid By using the method for preparing 5a, product 163 is obtained, starting with 100 mg of "UBE-4" (0.35 mmol, 1.0 eq.) and product 162 (305 mg, 0.62 mmol, 1.8 eq.) in 1 mL of anhydrous pyridine and 2 mL of anhydrous acetonitrile in the presence of DABCO (80 mg, 0.71 mmol, 2.0 eq.). The reaction medium is co-evaporated with ethanol. The obtained solid is purified on an SCX column, and the obtained solid is then hot-triturated in methanol and filtered. The expected product is obtained as a yellow solid (24 mg, 16%).

HPLC (5%-95% ACN gradient in $H_2O$); >99%

MS (ESI$^+$) (+0.1%, HCOOH): 415.48 [$C_{19}H_{19}FN_6O_4$+H]$^+$ (m/z)

MP=245° C. (decomposition).

EXAMPLE 68

8-fluoro-9-[(R)-3-(1H-imidazol-2-ylamino)-pyrrolidin-1-yl]-3-methyl-6-oxo-2,3-dihydro-6H-1-oxa-3,3a-diaza-phenalene-5-carboxylic acid

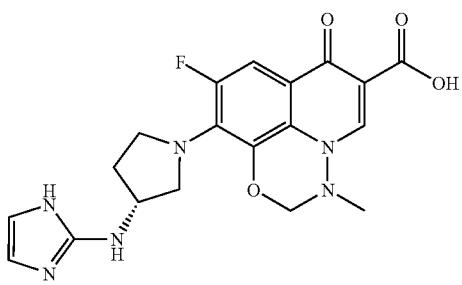

Stage A: Preparation of 164

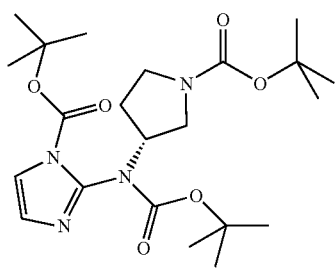

The method described for preparing 8a is used, by substituting 3-(S)-hydroxy-pyrrolidine-1-carboxylic acid tert-butyl ester (990 mg, 5.29 mmol, 1.5 eq.) for 3-hydroxy-pyrrolidine-1-carboxylic tert-butyl ester and product 160 (1.0 g, 3.53 mmol, 1.0 eq.) for product 7a. The raw product is purified by chromatography on silica by eluting with a cyclohexane-ethyl acetate mixture (1:0 to 6:4) and the product 164 is obtained as a white foam (1.2 g, 75%).

Stage B: Preparation of 165

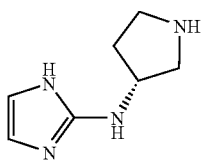

The method described for preparing 4a is used, by substituting product 164 (675 mg, 1.49 mmol, 1.0 eq.) for product 3a with 1.2 mL of trifluoroacetic acid in 15 mL of dichloromethane. The medium is co-evaporated with methanol and then triturated in ethyl ether. The expected product is obtained as a white powder (484 mg, 66%).

Stage C: 8-fluoro-9-[R)-3-(1H-imidazol-2-ylamino)-pyrrolidin-1-yl]-3-methyl-6-oxo-2,3-dihydro-6H-1-oxa-3,3a-diaza-phenalene-5-carboxylic acid By using the method for preparing 5a, product 166 is obtained starting with 140 mg of "UBE-4" (0.50 mmol, 1.0 eq.) and product 165 (460 mg, 0.93 mmol, 1.9 eq.) in 1.5 mL of anhydrous pyridine and 3 mL of anhydrous acetonitrile in the presence of DABCO (110 mg, 0.98 mmol, 2.0 eq.). The reaction medium is co-evaporated with methanol. The obtained residue is purified on an SCX column and then on a Sephadex® LH-20 column. The obtained solid is triturated in water, methanol and then in ethyl ether. The expected product is obtained as a yellow solid (44 mg, 21 %).

HPLC (5%-95% ACN gradient in $H_2O$); >95%

MS (ESI$^+$) (+0.1%, HCOOH): 415.49 [$C_{19}H_{19}FN_6O_4$+H]$^+$ (m/z)

MP=225° C. (decomposition).

EXAMPLE 69

8-fluoro-3-methyl-9-[(R)-3-(methyl-thiazol-2-yl-amino)-pyrrolidin-1-yl]-3-methyl-6-oxo-2,3-dihydro-6H-1-oxa-3,3a-diaza-phenalene-5-carboxylic acid (170)

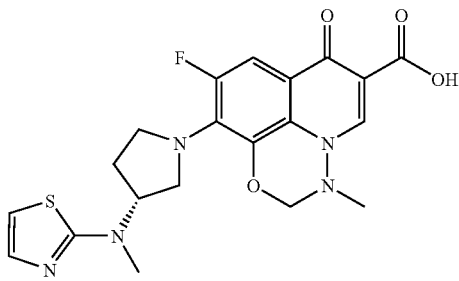

Stage A: Preparation of 167

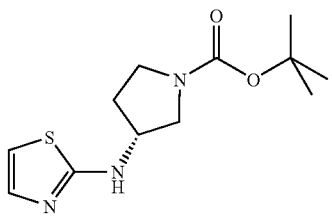

By using the method for preparing 7a, product 167 is obtained starting with 35b (500 mg, 1.26 mmol, 1.0 eq.). The raw product is subsequently used without any subsequent purification (350 mg, quantitative).

Stage B: Preparation of 168

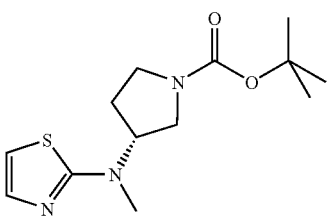

To a solution of 167 (340 mg, 1.26 mmol, 1.0 eq.) in 8 mL of anhydrous DMF, is added sodium hydride (50 mg, 1.25 mmol, 1.0 eq.). The mixture is stirred at room temperature for 30 minutes, and then methyl iodide (0.118 mL, 1.89 mmol, 1.5 eq.) is added. The mixture is stirred at room temperature for 1 hour and then evaporated. The residue is dissolved in ethyl acetate and then washed with water. The organic extracts are dried and then concentrated under reduced pressure. The raw product is purified by chromatography on silica by eluting with a cyclohexane-ethyl acetate mixture (1:0 to 6:4) and the product 164 is obtained as a yellow oil (270 mg, 75%).

Stage C: Preparation of 169

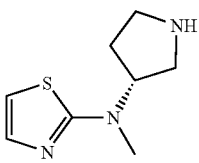

The method described for preparing the product 4a is used, by substituting product 168 for product 3a (265 mg, 0.93 mmol, 1.0 eq.) with 0.3 mL of trifluoroacetic acid in 5 mL of dichloromethane. The medium is diluted with dichloromethane and water. The aqueous phase is alkalinized with an aqueous sodium hydroxide (1N) solution and extracted with dichloromethane. The organic extracts are dried and concentrated under reduced pressure. The expected product is obtained as a pale yellow oil (138 mg, 73%).

Stage D: 8-fluoro-3-methyl-9-[(R)-3-(methyl-thiazol-2-yl-amino)-pyrrolidin-1-yl]-6-oxo-2,3-dihydro-6H-1-oxa-3,3 a-diaza-phenalene-5-carboxylic acid By using the method for preparing 5a, product 170 is obtained, starting with 100 mg of "UBE-4" (0.35 mmol, 1.0 eq.) and product 169 (130 mg, 0.71 mmol, 2.0 eq.) in 0.5 mL of anhydrous pyridine and 1 mL of anhydrous acetonitrile in the presence of DABCO (120 mg, 1.07 mmol, 3.0 eq.). The reaction medium is co-evaporated with methanol. The obtained solid is triturated in methanol and in ethyl ether. The expected product is obtained as a yellow solid (137 mg, 88%).

HPLC (5%-95% ACN gradient in $H_2O$); >99%

MS (ESI$^+$) (+0.1%, HCOOH): 446.5 $[C_{20}H_{20}FN_5O_4+H]^+$ (m/z)

MP=222-224° C.

EXAMPLE 70

9-[(R)-3-(acetyl-thiazol-2-yl-amino)-pyrrolidin-1-yl]-8-fluoro-3-methyl-6-oxo-2,3-dihydro-6H-1-oxa-3,3a-diaza-phenalene-5-carboxylic acid

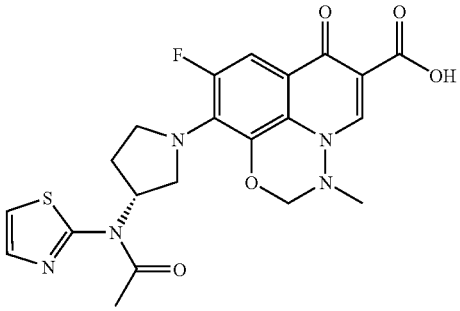

A solution of product 36b (200 mg, 0.46 mmol, 1.0 eq.) in trifluoroacetic anhydride (5 mL) is heated to 90° C. for 6 hours. The reaction medium is cooled down to room temperature, the mixture is filtered and the filtrate is concentrated under reduced pressure. The obtained residue is re-crystallized from methanol and then purified by preparative HPLC (acetonitrile/$H_2O$ gradient). The expected product is obtained as a beige solid (25 mg, 88%).

HPLC (5%-95% ACN gradient in $H_2O$); >95%

MP=220-222° C.

EXAMPLE 71

8-fluoro-3-methyl-9-[3-amino-4-(thiazol-2-yl)-pyrrolidin-1-yl]-6-oxo-2,3-dihydro-6H-1-oxa-3,3a-diaza-phenalene-5-carboxylic acid (177)

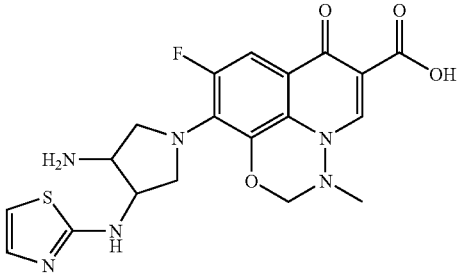

Stage A: preparation of 171

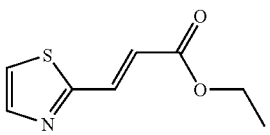

A solution of triethyl phosphonoacetate (2.6 g, 11.60 mmol, 1.3 eq.) in THF (5 mL) is added dropwise to a suspension of NaH (424 mg, 10.60 mmol, 1.2 eq.) in THF (8 mL) at 0° C. The reaction medium is stirred at 0° C. for 30 minutes and a solution of 2-formylthiazole (1.0 g, 8.84 mmol, 1.0 eq.) in THF (8 mL) is added. The mixture is stirred at room temperature for 16 hours. The reaction medium is concentrated and then diluted with dichloromethane and washed with water and a saturated sodium chloride solution. The isolated organics extracts are dried and then the solvent is evaporated under reduced pressure. The raw expected product is obtained, which is purified by chromatography on silica by eluting with a cyclohexane-ethyl acetate mixture (10:0 to 85:15) and the expected product 171 is obtained as a colorless oil (1.7 g, 100%).

Stage B: Preparation of 172

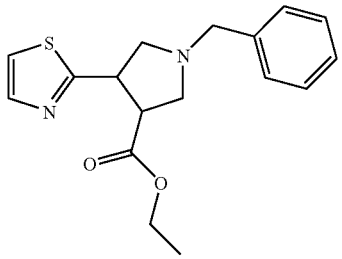

N-methoxymethyl)-N-(trimethylsilylmethyl)-benzyl-amine (466 mg, 1.96 mmol, 1.2 eq.) and a trifluoroacetic acid solution in dichloromethane (1N, 170 µL, 0.17 mmol, 0.1 eq.) are added to a solution of 171 (300 mg, 1.64 mmol, 1.0 eq.) in dichloromethane (5 mL) at 0° C. The reaction medium is stirred at 0° C. for 20 minutes and at room temperature for 4 hours. The medium is then diluted with dichloromethane, washed with water and then with an aqueous saturated sodium chloride solution. The isolated organic extracts are dried and the solvent is evaporated under reduced pressure. The pure expected product is obtained as a yellow oil (516 mg, 98%).

Stage C: Preparation of 173

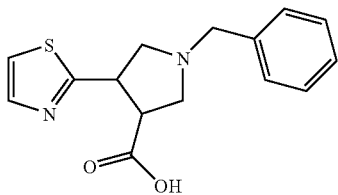

A solution of 172 (500 mg, 1.73 mmol, 1.0 eq.) in an aqueous 6N HCl solution is stirred at room temperature for 16 hours. The reaction medium is then evaporated under reduced pressure, co-evaporated with toluene, and then dried on $P_2O_5$ in vacuo. The expected product is obtained pure as a white solid (497 mg, 99%).

Stage D: Preparation of 174

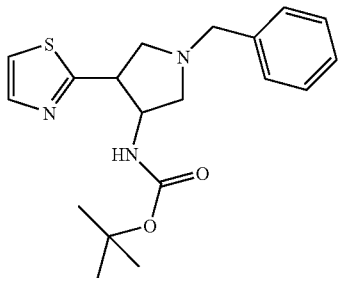

To a suspension of 173 (2.3 g, 8.03 mmol, 1.0 eq.) in tert-butyl alcohol (30 mL), are added triethylamine (2.30 mL, 10.41 mmol, 1.3 eq.) and diphenylphosphoryl azide (2.30 mL, 16.55 mmol, 2.0 eq.). The reaction medium is stirred at 90° C. for 16 hours. Triethylamine (2.30 mL, 16.55 mmol, 2.0 eq.) and di-tert-butyl dicarbonate (2.6 g, 11.91 mmol, 1.5 eq.) are added to the mixture and the latter is stirred at 55° C. for 3 hours. The reaction medium is concentrated under reduced pressure. The raw product is purified by chromatography on silica by eluting with a cyclohexane-ethyl acetate mixture (1:0 to 4:6) and the product 174 is obtained as a beige solid (296 mg, 10%).

Stage E: Preparation of 175

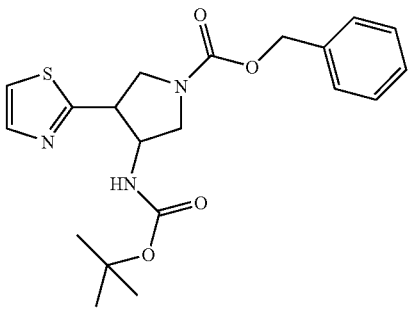

To a solution of 174 (296 mg, 0.82 mmol, 1.0 eq.) in chloroform (4 mL), is added chlorobenzyl formate (281 mg, 1.64 mmol, 2.0 eq.). The reaction medium is stirred at 60° C. for 7 hours. The reaction medium is concentrated under reduced pressure. The raw product is purified by chromatography on silica by eluting with a cyclohexane-ethyl acetate mixture (1:0 to 4:6) and the product 175 is obtained as a beige foam (220 mg, 67%).

Stage F: Preparation of 176

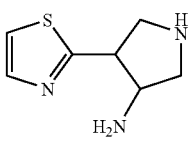

To a solution of 175 (250 mg, 0.62 mmol, 1.0 eq.) in acetonitrile (4.5 mL), are added sodium iodide (371 mg, 2.47 mmol, 4.0 eq.) and trimethylsilyl chloride (269 mg, 2.47 mmol, 2.0 eq.). The reaction medium is stirred at room temperature for 1 hour and methanol is then added (5 mL). The reaction medium is concentrated under reduced pressure. The raw product is purified on a Sephadex® LH-20 column and then on an SCX column. The product 176 is obtained as a colorless oil (62 mg, 59%).

Stage G: 8-fluoro-3-methyl-9-[3-amino-4-(thiazol-2-yl)-pyrrolidin-1-yl]-6-oxo-2,3-dihydro-6H-1-oxa-3, 3a-diaza-phenalene-5-carboxylic acid By using the method for preparing 5a, product 177 is obtained starting with 52 mg of "UBE-4" (0.18 mmol, 1.0 eq.) and with product 176 (62 mg, 0.36 mmol, 2.0 eq.) in 0.5 mL of anhydrous pyridine and 1 mL of anhydrous acetonitrile in the presence of DABCO (101 mg, 0.91 mmol, 2.5 eq.). The reaction medium is co-evaporated with methanol. The obtained solid is triturated in methanol and purified by preparative TLC. The expected product is obtained as a yellow solid (19 mg, 22%).

HPLC (5%-95% ACN gradient in $H_2O$); >99%

MS (ESI$^+$) (+0.1%, HCOOH): 432.4 [$C_{19}H_{18}FN_5O_4S$+H]$^+$ (m/z)

MP=240-245° C.

EXAMPLE 72

8-fluoro-9-[(R)-3-H-imidazol-2-ylamino)-pyrrolidin-1-yl]-3-methyl-6-oxo-2,3-dihydro-6H-1-oxa-3,3a-diaza-phenalene-5-carboxylic acid (182)

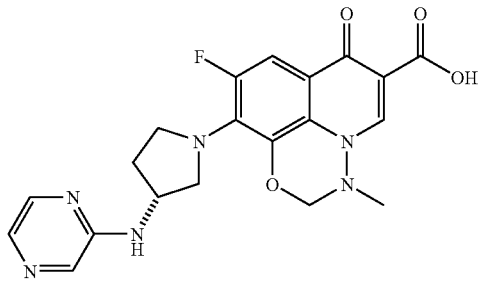

Stage A: Preparation of 178

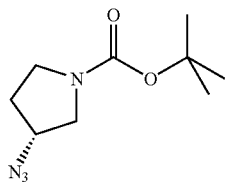

The product is prepared according to the method described in US 2003/0225107 by substituting 3-hydroxy-pyrrolidinol with 3-(S)-hydroxy-pyrrolidinol (1.0 g, 5.34 mmol, 1.0 eq.). 178 is obtained as an orange oil (1.2 g, 100%).

Stage B: Preparation of 179

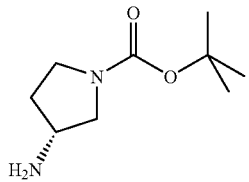

To a solution of product 178 (907 mg, 4.27 mmol, 1.0 eq.) in 25 mL of methanol, palladium on charcoal (454 mg, 0.43 mmol, 0.1 eq.) is added. The reaction medium is submitted to hydrogenation at atmospheric pressure and at room temperature for 6 hours. The reaction medium is then filtered on celite and concentrated under dry conditions under reduced pressure. The expected compound is obtained as a yellow oil (740 mg, 93%).

Stage C: Preparation of 180

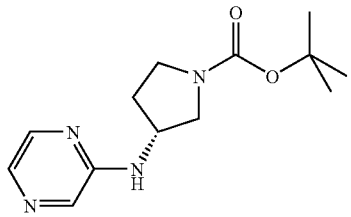

The method described in the preparation of 3a-3b is used by substituting 3-(R)-amino-pyrrolidine-1-carboxylic acid tert-butyl ester 179 for 3-aminomethyl-pyrrolidine-1-carboxylic acid tert-butyl ester. The expected compound is obtained as a yellow solid (482 mg, 55%).

Stage D: Preparation of 181

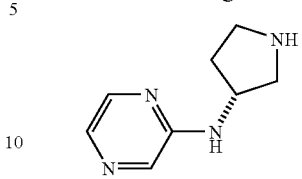

The method described in the preparation of 4c is used, by substituting product 180 for product 3c. The expected compound is obtained as a yellow solid (368 mg, 100%).

Stage E: 8-fluoro-9-[(R)-3-(1H-imidazol-2-ylamino)-pyrrolidin-1-yl]-3-methyl-6-oxo-2,3-dihydro-6H-1-oxa-3,3a-diaza-phenalene-5-carboxylic acid The method described in the preparation of 5c is used, by substituting product 181 (367 mg, 1.8 mmol, 1.8 eq.) for product 4c, the expected compound is obtained as a yellow solid (23 mg, 6%).

HPLC (5%-80% ACN gradient in $H_2O$); >95%
MS (ESI$^+$) (+0.1%, HCOOH): 427.2 $[C_{20}H_{19}FN_6O_4+H]^+$ (m/z)
MP=255° C. (decomposition).

EXAMPLE 73

8fluoro-9-[(R)-3-(1H-imidazol-2-ylamino)-pyrrolidin-1-yl]-3-methyl-6-oxo-2,3-dihydro-6H-1-oxa-3,3a-diaza-phenalene-5-carboxylic acid (187)

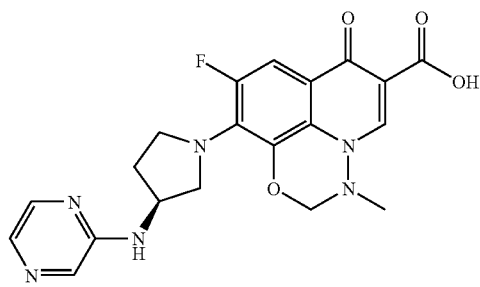

Stage A: Preparation of 183

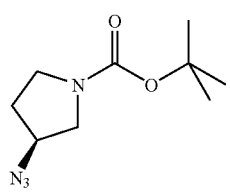

The product is prepared according to the method described in US 2003/0225107 by substituting 3-hydroxy-pyrrolidinol with 3-(R)-hydroxy-pyrrolidinol (2.0 g, 10.68 mmol, 1.0 eq.). 183 is obtained as a yellow liquid (2;0 g, 89%).

Stage B: Preparation of 184

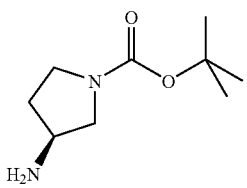

To a solution of product 178 (2.0 g, 9.42 mmol, 1.0 eq.) in 40 mL of methanol, palladium on charcoal (1.0 g, 0.94 mmol, 0.1 eq.) is added. The reaction medium is submitted to hydrogenation at atmospheric pressure and at room temperature for 6 hours. The reaction medium is then filtered on celite and concentrated under dry conditions under reduced pressure. The expected compound is obtained as a yellow oil (1.7 g, 97%).

Stage C: Preparation of 185

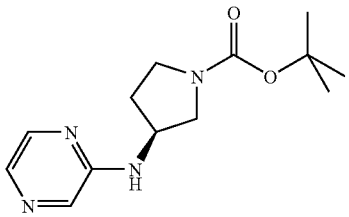

The method described in the preparation of 3a-3b is used by substituting 3-(S)-amino-pyrrolidin-1-carboxylic acid tert-butyl ester 184 for 3-aminomethyl-pyrrolidin-1-carboxylic acid tert-butyl ester. The expected compound is obtained as a yellow solid (510 mg, 26%).

Stage D: Preparation of 186

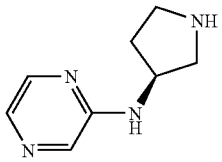

The method described in the preparation of 4c is used by substituting product 185 for product 3c. The expected compound is obtained as a yellow solid (470 mg, 100%).

Stage E: 8-fluoro-9-[(S)-3-(1H-imidazol-2-ylamino)-pyrrolidin-1-yl]-3-methyl-6-oxo-2,3-dihydro-6H-1-oxa-3,3a-diaza-phenalene-5-carboxylic acid By using the method for preparing 5a, product 187 is obtained starting with 100 mL of "UBE-4" (0.35 mmol, 1.0 eq.) and with product 186 (150 mg, 0.91mmol, 2.6 eq.) in 0.5 mL of anhydrous pyridine and 1.5 mL of anhydrous acetonitrile in the presence of DABCO (100 mg, 0.89 mmol, 2.5 eq.). The obtained precipitate is filtered and then washed with acetonitrile and ethyl ether. The expected product is obtained as a yellow solid (120 mg, 80%).

HPLC (5%-95% ACN gradient in $H_2O$); >99%
MS (ESI$^+$) (+0.1%, HCOOH): 432.4 $[C_{20}H_{19}FN_6O_4+H]^+$ (m/z) MP=257-259° C.

EXAMPLE 74

8-fluoro-3-(2-fluoro-ethyl)-6-oxo-9-[(R)-3-(thiazol-2-ylamino)-pyrrolidin-1-yl]-2,3-dihydro-6H-1-oxa-3,3a-diaza-phenalene-5-carboxylic acid (196)

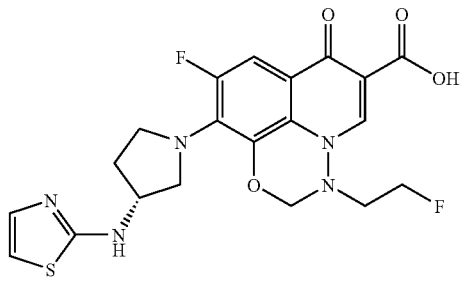

Stage A: Preparation of 188

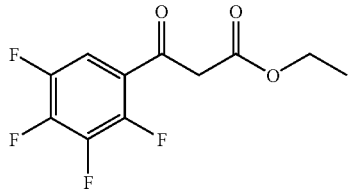

A solution of N-butyllithium (2.5M/hexane, 8.3 mL, 20.68 mmol, 4.4 eq.) is added to a solution of monoethyl malonate (1.36 g, 10.35 mmol, 2.2 eq.) in THF (15 mL) at 0° C. The reaction medium is cooled to −50° C. and a solution of 2,3,4,5-tetrafluorobenzoyl chloride in THF (5 mL) is added dropwise. The mixture is then stirred at room temperature for 16 hours. The reaction is hydrolyzed by an aqueous 1N HCl solution, and then the organic phase is extracted with ethyl acetate. The isolated organic extracts are dried and the solvent is then evaporated under reduced pressure. The raw expected product is obtained, which is purified by chromatography on silica by eluting with a cyclohexane-ethyl acetate mixture (1:0 to 9:1) and the expected product 188 is obtained as a pale orange oil (600 mg, 50%).

Stage B: Preparation of 189

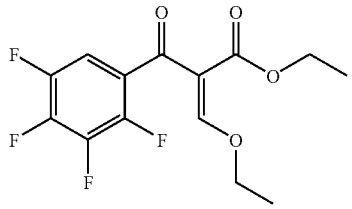

A mixture of product 188 (1.8 g, 6.70 mmol, 1.0 eq.), triethyl orthoformate (1.7 mL, 10.05 mmol, 1.5 eq.) and acetic anhydride (2.7 mL, 26.80 mmol, 4.0 eq.) is stirred at 125° C. in a sealed tube for 16 hours. The medium is concentrated under reduced pressure and the product 189 (1.8 g, 88%) is used without any subsequent purification.

Stage C: Preparation of 190

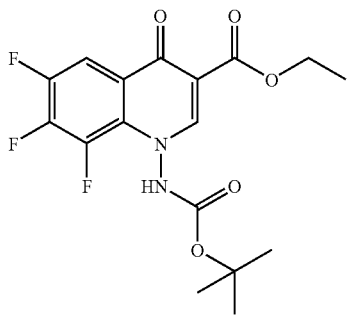

A solution of Boc-hydrazine (870 mg, 6.55 mmol, 1.1 eq.) and of product 189 (1.8 g, 5.95 mmol, 1.0 eq.) in toluene (9 mL) is stirred at 80° C. for 4 hours. The reaction is hydrolyzed by adding water, and the organic phase is then extracted with ethyl acetate. The isolated organic extracts are dried and the solvent is then evaporated under reduced pressure. The raw expected product is obtained, which is purified by chromatography on silica by eluting with a cyclohexane-ethyl acetate mixture (1:0 to 5:5) and the expected product 190 is obtained as a pale yellow solid (800 mg, 35%).

Stage D: Preparation of 191

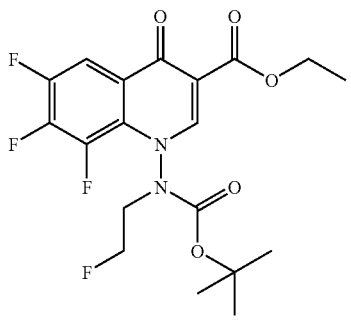

To a solution of product 190 (600 mg, 1.55 mmol, 1.0 eq.) and of triphenyl phosphine (615 mg, 2.30 mmol, 1.5 eq.) in THF (6 mL) at 0° C., are added diethyl azodicarboxylate (1.08 mL, 2.30 mmol, 1.5 eq.) and 2-fluoroethanol. The reaction medium is stirred at room temperature for 16 hours. The reaction is hydrolyzed by adding water, and the organic phase is then extracted with ethyl acetate and washed with an aqueous 1N HCl solution. The isolated organic extracts are dried and the solvent is then evaporated under reduced pressure. The raw expected product is obtained, which is purified by chromatography on silica by eluting with a cyclohexane-ethyl acetate mixture (1:0 to 5:5) and the expected product 191 is obtained as a yellow solid (495 mg, 73%).

Stage E: Preparation of 192

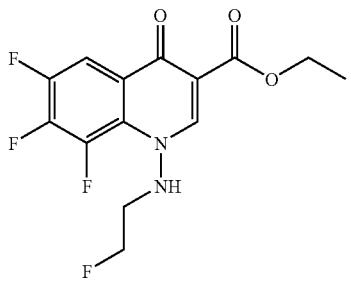

The method described for preparing the product 4a is used, by substituting for product 3a, product 191 (514 mg, 1.19 mmol, 1.0 eq.) with 2.5 mL of trifluoroacetic acid in 5 mL of dichloromethane. The medium is diluted with dichloromethane and water. The aqueous phase is alkalinized with an aqueous (1N) sodium hydroxide solution and extracted with dichloromethane. The organic extracts are dried and concentrated under reduced pressure. The expected product is obtained as a pale yellow oil (315 mg, 79%).

Stage F: Preparation of 193

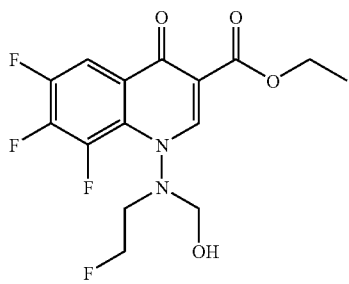

A suspension of product 192 (310 mg, 1.19 mmol, 1.0 eq.) and of paraformaldehyde (1.2 g, 39.90 mmol, 40.0 eq.) in water is stirred at 110° C. in a sealed tube for 48 hours. The medium is cooled at room temperature and the obtained precipitate is filtered, washed with methanol, and ethyl ether. The expected product is obtained as a white solid (254 mg, 77%).

Stage G: Preparation of 194

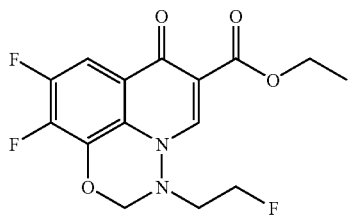

A suspension of product 194 (600 mg, 1.66 mmol, 1.0 eq.) in THF (35 mL) is heated to reflux in less than 5 minutes and TBAF (3.7 mL, 3.67 mmol, 2.2 eq.) is added very rapidly. The reaction medium is stirred at reflux for 20 minutes. The mixture is then poured onto a saturated sodium carbonate solution, and the organic phase is then separated and then extracted with ethyl acetate. The isolated organic extracts are dried and the solvent is then evaporated under reduced pressure. The residue is taken up in ethyl acetate and a precipitate is formed by adding ethyl ether. The precipitate is filtered and dried in vacuo. The expected product is obtained as a beige solid (240 mg, 42%).

Stage H: Preparation of 195

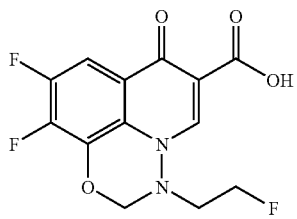

Lithium hydroxide (227 mg, 5.40 mmol, 5.0 eq.) is added to a solution of product 195 (370 mg, 1.08 mmol, 1.0 eq.) in a water/THF mixture (4 mL/4mL). The reaction medium is stirred at room temperature for 7 hours. The formed precipitate is filtered, washed with ethyl ether and then dried in vacuo. The expected product is obtained as a white solid (286 mg, 84%).

Stage I: 8-fluoro-3-(2-fluoro-ethyl)-6-oxo-9-[(R)-3-(thiazol-2-ylamino)-pyrrolidin-1-yl]-2,3-dihydro-6H-1-oxa-3,3 a-diaza-phenalene-5-carboxylic acid

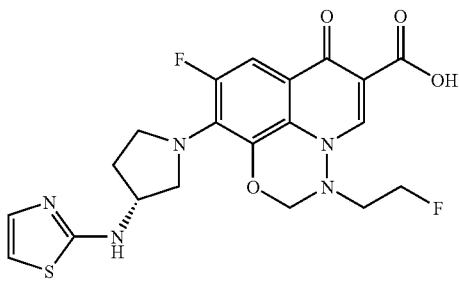

By using the method for preparing 5a, product 196 is obtained starting with 100 mg of product 195 (0.32 mmol, 1.0 eq.) and with product 35b (108 mg, 0.64 mmol, 2.0 eq.) in 0.8 mL of anhydrous pyridine and 1.5 mL of anhydrous acetonitrile in the presence of DABCO (72 mg, 0.64 mmol, 2.0 eq.). The reaction medium is evaporated under reduced pressure. The result is triturated in methanol and then purified by preparative TLC. The expected product is obtained as a yellow solid (18 mg, 12%).

HPLC (5%-95% ACN gradient in $H_2O$); >99%
MS ($ESI^+$) (+0.1%, HCOOH): 432.4 $[C_{20}H_{19}F_2N_5O_4S+H]^+$ (m/z)
MP=242-245° C.

Anti-Infectious Activity Test Protocol a. Aim of the study and choice of strains In order to assess the anti-infectious activity, a test to determine the minimal inhibitory concentrations (MIC), of the synthesized molecules is implemented. This comparative test, using a reference fluoroquinolone, measures the minimum inhibitory concentrations for the principal reference and in-situ bacteria, isolated from human and animal pathologies (canine, feline, bovine or porcine). These bacteria represent different resistance populations vis-à-vis the fluoroquinolones for each bacterial species selected and come from Vetoquinol S.A.'s private collection or ATCC references, M. haemolytica (2); B. bronchiseptica; P. aeruginosa (2); E. coli (3); S. aureus (3); S. uberis; M. bovis and bovirhinis; C. perfringens.

b. Experimental Methodology for Determining MICs

MIC determination is carried out by microdilution in a liquid medium. The method used for the aerobic and anaerobic bacteria is based on the CLSI (NCCLS) M31-A (May 2002) guideline "Performance Standards for Antimicrobial Disk and dilution susceptibility tests for bacteria isolated from animals". The method used for the mycoplasma is based on the CLSI (NCCLS) M31-A (May 2002) guideline and the article by F. Poumarat and J. L. Martel. For each molecule, the concentrations to be tested vis-a-vis the strains are:

either between 0.001 and 1 µg/ml or between 0.03 and 32 µg/ml

Controls were introduced into each test.

Acceptable results of these controls validate the results obtained for each molecule.

c. Results

The results obtained for each of the molecules are summarized in table form in order to:

Assess the intrinsic performance of the molecule

Facilitate comparison between molecules

Discuss the data obtained in relation to the reference.

TABLE OF MICs (µg/ml)

| Compound of example | Man hae s | Man hae r | Bor bron | Pse aer s | Pse aer r | E coli | Str ube |
|---|---|---|---|---|---|---|---|
| 8 | 0.25 | 32 | >1 | 8 | >32 | 0.5 | 0.25 |
| 1 | 0.06 | 16 | 0.5 | 8 | 16 | 0.25 | <0.03 |
| 7 | 0.06 | 16 | 0.5 | 2 | 16 | 0.25 | 0.06 |
| 19 | 0.03 | 8 | 0.12 | 2 | 8 | 0.06 | <0.03 |
| 18 | 0.12 | >32 | 0.25 | 4 | 32 | 0.5 | 0.25 |
| 10 | 0.03 | >32 | 2 | 4 | >32 | 0.25 | <0.03 |
| 33 | 0.06 | 8 | 0.5 | 0.5 | 8 | 0.06 | 0.12 |
| 27 | 0.008 | 4 | 2 | 0.06 | 2 | 0.03 | 0.25 |
| 29 | 0.03 | 8 | >1 | 0.25 | 4 | 0.06 | 0.5 |
| 28 | 0.008 | 4 | 1 | 0.06 | 1 | 0.03 | 0.25 |
| 38 | 0.03 | 16 | 1 | 4 | 32 | 0.12 | <0.03 |
| 34 | 0.03 | 8 | 0.5 | 0.5 | 8 | 0.03 | 0.12 |
| 35 | 0.06 | 8 | 1 | 0.5 | 8 | 0.06 | 0.12 |
| 39 | 0.03 | 16 | 0.5 | 2 | 16 | 0.25 | 0.12 |

| Compound of example | Sta aur s | Sta aur r | Myc bov | Clo per | E. coli ATCC 25922 | E. fae-calis ATCC 29212 | M. bovirhinis |
|---|---|---|---|---|---|---|---|
| 8 | 0.06 | 4 | 0.06 | <0.03 | 0.12 | 0.25 | 0.06 |
| 1 | <0.03 | 0.5 | <0.03 | 0.06 | 0.12 | ≦0.03 | 0.06 |
| 7 | <0.03 | 0.5 | <0.03 | 0.06 | 0.25 | ≦0.03 | 0.06 |
| 19 | <0.03 | 0.25 | <0.03 | <0.03 | 0.25 | 0.06 | 0.25 |
| 18 | <0.03 | 4 | 0.25 | 0.06 | 0.06 | ≦0.03 | ≦0.03 |
| 10 | <0.03 | 4 | 0.12 | <0.03 | 1 | 0.25 | 2 |
| 33 | <0.03 | 2 | 0.5 | 0.06 | 0.03 |  | 0.25 |
| 27 | 0.12 | 8 | 1 | 0.25 | 0.03 | 2 | 1 |
| 29 | 0.12 | 8 | 0.5 | 0.25 | 0.06 | 1 to 2 | 1 |
| 28 | 0.12 | 4 | 1 | 0.12 | 0.03 | 1 to 2 |  |
| 38 | 0.06 | 2 | 0.12 | <0.03 | 0.12 | 0.06 | 0.25 |

-continued

TABLE OF MICs (µg/ml)

| 34 | <0.03 | 2 | 0.5 | <0.03 | 0.03 | 0.25 to 0.5 | 0.12 |
| 35 | 0.06 | 2 | 0.5 | 0.12 | 0.03 | 0.25 | |
| 39 | <=0.03 | 2 | 0.12 | <=0.03 | 0.03 to 0.12 | 0.12 | 0.06 |

Names of the bacteria:
Man hae = Mannheimia haemolytica,
Bor bron = Bordetella bronchiseptica,
Pse aer = Pseudomonas aeruginosa,
s = susceptible
E. coli = Escherichia coli,
Str ube = Streptococcus uberis,
Sta aur = Staphylococcus aureus,
Myc bov = Mycoplasma bovis,
Clo per = Clostridium perfringens
r = resistant

The invention claimed is:
1. A compound of formula (I):

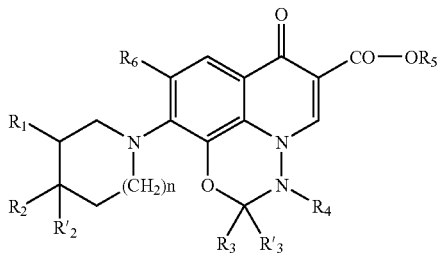

in which
either $R_1$ represents:
H, OH, $NH_2$, —$(CH_2)_m$—$NR_aR_b$ in which m =0.1 or 2,
$R_a$ and $R_b$ are identical or different and represent H, linear, branched or cyclic ($C_1$-$C_6$) alkyl, ($C_3$-$C_6$) cycloalkyl-($C_1$-$C_6$)-alkyl;
or also represent $R_c$,$S(O)_2R_c$, $C(O)R_c$,$S(O)_2R_d$ or $C(O)R_d$;
or $R_a$ and $R_b$ form together with the nitrogen atom, an $R_c$ radical;
$R_c$ represents a saturated, unsaturated or aromatic 5- to 6-member ring containing 1 to 4 heteroatoms chosen from N, O and S, optionally substituted by 1 to 3 ($C_1$-$C_6$) alkyl radicals, said ring being linked, if appropriate, to the nitrogen atom of $NR_aR_b$ by a nitrogen atom or a carbon atom;
$R_d$ represents a linear or branched ($C_1$-$C_6$) alkyl or ($C_3$-$C_6$) cyclic alkyl radical, optionally substituted by 1 to 4 halogens;
or $R_1$ represents $R_c$ or $CHR_eR_c$ or $CHR_eR_d$;
$R_c$ and $R_d$ are as defined above, $R_e$ represents H, OH, $NH_2$, NH—($C_1$-$C_6$)-alk or N—($C_1$-$C_6$)- $alk_2$, or NH—($C_1$-$C_7$)-acyl or $NHR_c$, $R_c$ being as defined above;
$R_2$ represents:
H, $(CH_2)_m$—$NR_aR_b$, $R_c$, $CHR_eR_c$ or $CHR_eR_d$,
$R_a$, $R_b$, $R_c$, $R_d$ and $R_e$ are as defined above;
and $R'_2$ represents H;
it being understood that $R_1$ and $R_2$ cannot at the same time be H or that $R_1$ and $R_2$ or $R_2$ and $R_1$ cannot be one $(CH_2)_m$—$NR_aR_b$ or $R_c$ or H and the other one OH, or one H and the other one $NH_2$, or one H and the other one $(CH_2)_m$—$NR_aR_b$ in which $R_a$ and $R_b$ represent H or ($C_1$-$C_6$) alkyl or $C(O)R_d$, in which $R_d$ represents an unsubstituted linear or branched ($C_1$-$C_6$) alkyl or ($C_3$-$C_6$) cyclic alkyl radical;

or $R_1$ has the above definition except H and $R_1$ and $R'_2$ together represent gem ($C_1$-$C_6$) dialkyl or ($C_1$-$C_6$) alkyl-oxime, or $R_2$ and $R'_2$ represent respectively $R_c$ or $R_d$ and OH, $NH_2$, $NHR_c$ or $NHR_f$, $R_c$ and $R_d$ being as defined above and $R_f$ being a ($C_1$-$C_7$) acyl radical;
or $R_1$ represents H and $R_2$ and $R'_2$ together represent ($C_1$-$C_6$) alkyl-oxime or one represents $R_c$ and the other one represents OH, $NH_2$, $NHR_c$ or $NHR_f$, $R_c$ and $R_f$ being defined as above;
n is 0 or 1;
$R_3$ and $R'_3$, identical or different, represent H or ($C_3$-$C_6$) alkyl optionally substituted by 1 to 3 halogens or $R_3$ represents a ($C_1$-$C_6$) alkoxy carbonyl group and $R'_3$ represents H;
$R_4$ represents methyl optionally substituted by one to three halogens;
$R_5$ represents H, ($C_3$-$C_6$) alkyl or ($C_7$-$C_{12}$) arylalkyl;
$R_6$ represents H, fluorine, $NO_2$, $CF_3$ or CN;
in the form of mixtures of enantiomers or single enantiomers, as well as their addition salts with mineral and organic acids and their salts with mineral or organic bases.

2. A compound of formula (I) according to claim 1, in which $R_3$ and $R'_3$ represent H and $R_4$ represents methyl.

3. A compound of formula (I) according to claim 1, in which $R_6$ represents fluorine.

4. A compound of formula (I) according to claim 1, in which one of the substituents $R_1$ or $R_2$ represents $(CH_2)_m$—$NR_aR_b$ in which m is 0 or 1, Rc, $CHR_eR_c$ or $CHR_eR_d$ and the other represents H.

5. A compound of formula (I) according to claim 1, in which one of the substituents $R_1$ or $R_2$ represents $(CH_2)_m$—$NR_aR_b$ in which m is 0 and the other represents H.

6. A compound of formula (I) according to claim 5, in which m=0, one of the substituents $R_a$ or $R_b$ represents a 5- or 6-member aromatic ring, containing 1 to 4 heteroatoms chosen from N, O and S, optionally substituted by 1 to 3 ($C_1$-$C_6$) alkyl radicals, said ring being linked, if appropriate, to the nitrogen atom of $NR_aR_b$ by a nitrogen atom or a carbon atom, and the other represents H.

7. A compound of formula (I) according to claim 5, in which m=0, one of the substituents $R_a$ or $R_b$ represents a $C(O)R_d$ radical and the other represents H.

8. A compound of formula (I) according to claim 1, in which one of the substituents $R_1$ or $R_2$ represents $CHR_eR_c$ or $CHR_eR_d$ and the other represents H.

9. A compound of formula (I) according to claim 1, in which $R_1$ represents OH or $NH_2$ and $R_2$ and $R'_2$ represent gem ($C_1$-$C_6$) dialkyl.

10. A compound of formula (I) according to claim 1, in which $R_1$ represents hydrogen or $-(CH_2)_m-NR_aR_b$ and $R_2$ and $R'_2$ represent ($C_1$-$C_6$) alkyl oxime.

11. A compound of formula (I) according to claim 1, in which n is 0.

12. A compound according to claim 1, selected from the group consisting of:
   8-fluoro-3-methyl-6-oxo-9-(3-(pyrazine-2-ylaminomethyl)-pyrrolidine-1-yl(-2,3-dihydro-6H-1-oxa-3,3a-diaza-phenalene-5-carboxylic acid,
   8-fluoro-3-methyl-6-oxo-9-(3-pyrazine-2-ylamino)-pyrrolidine-1-yl)-2,3-dihydro-6H-1-oxa-3,3a-diaza-phenalene-5-carboxylic acid,
   8-fluoro-3-methyl-6-oxo-9-(3-((1,3,4(thiadiazol-2-ylamino)-pyrrolidine-1-yl)-2,3-dihydro-6H-1-oxa-3,3a-diaza-phenalene-5-carboxylic acid,
   8-fluoro-3-methyl-6-oxo-9-[(S)-3-(thiazol-2-ylamino)-pyrrolidine-1-yl]-(-2,3-dihydro-6H-1-oxa-3,3a-diaza-phenalene-5-carboxylic acid,
   8-fluoro-3methyl-6-oxo-9-(3-(2,2,2-trifluoro-acetylamino)-pyrrolidine-1-yl)-2,3-dihydro-6H-1-oxa-3,3a-diaza-phenalene-5-carboxylic acid,
   8-fluoro-3-methyl-6-oxo-9-((R)-3-(2,2,2-trifluoro-acetylamino)-pyrrolidine-1-yl(-2,3-dihydro-6H-1-oxa-3,3a-diaza-phenalene-5-carboxylic acid,
   9-((R,S)-4-amino-3,3-dimethyl-pyrrolidine-1-yl)-8-fluoro-3-methyl-6-oxo-2,3-dihydro-6H-1-oxa-3,3a-diaza-phenalene-5-carboxylic acid,
   9-((R)-4-amino-3,3-dimethyl-pyrrolidine-1-yl)-8-fluoro-3-methyl-6-oxo-2,3-dihydro-6H-1-oxa-3,3a-diaza-phenalene-5-carboxylic acid,
   9-(3-(amino-thiazol-2-yl-methyl)-pyrrolidine-1-yl(-8-fluoro-3-methyl-6-oxo-2,3-dihydro-6H-1-oxa-3,3a-diaza-phenalene-5-carboxylic acid,
   8-fluoro-9-(3-((Z/E)-methoxyimino(-pyrrolidine-1-yl(-3-methyl-6-oxo-2,3-dihydro-6-H-1-oxa-3,3a-diaza-phenalene-5-carboxylic acid,
   8-fluoro-9-(3-(aminomethyl)-4-methoxyimino-pyrrolidine-1-yl]-3-methyl-6-oxo-2,3-dihydro-6H-1-oxa-3,3a-diaza-phenalene-5-carboxylic acid,
   8-fluoro-3-methyl-6-oxo-9-[(R)-3-(thiazol-2-ylamino)-pyrrolidine-1-yl]-2,3-dihydro-6H-1-oxa-3,3a-diaza-phenalene-5-carboxylic acid,
   8-fluoro-3-methyl-6-oxo-9-[(S)-3-(2,2,2-trifluoro-acetylamino)-pyrrolidine-1-yl]-2,3-dihydro-6H-1-oxa-3,3a-diaza-phenalene-5-carboxylic acid,
   9-((S)-4-amino-3,3-dimethyl-pyrrolidine-1-yl)-8-fluoro-3-methyl-6-oxo-2,3-dihydro-6H-1-oxa-3,3a-diaza-phenalene-5-carboxylic acid,
   and salts thereof.

13. A compound selected from the group consisting of:
   8-Fluoro-3-methyl-6-oxo-9-[(R)-3-(thiazol-2-ylamino)-pyrrolidin-1-yl]-2,3-dihydro-6H-1-oxa-3,3a-diaza-phenalene-5-carboxylic acid;
   8-fluoro-3methyl-6-oxo-9-(3-(2,2,2-trifluoro-acetylamino)-pyrrolidine-1-yl)-2,3-dihydro-6H-1-oxa-3,3a-diaza-phenalene-5-carboxylic acid;
   8-Fluoro-3-methyl-6-oxo-9-[(S)-3-(2,2,2-trifluoro-acetylamino)-pyrrolidine-1-yl]-2,3-dihydro-6H-1-oxa-3,3a-diaza-phenalene-5-carboxylic acid;
   9-((R,S)-4-amino-3,3-dimethyl-pyrrolidine-1-yl)-8-fluoro-3-methyl-6-oxo-2,3-dihydro-6H-1 -oxa-3,3a-diaza-phenalene-5-carboxylic acid;
   9-((S)-4-Amino-3,3-dimethyl-pyrrolidin-1-yl)-8-fluoro-3-methyl-6-oxo-2,3-dihydro-6H-1-oxa-3,3a-diaza-phenalene-5-carboxylic acid;
   9-((R)-4-Amino-3,3-dimethyl-pyrrolidin-1-yl)-8-fluoro-3-methyl-6-oxo-2,3-dihydro-6H-1-oxa-3,3a-diaza-phenalene-5-carboxylic acid;
   and salts thereof.

14. A compound according to claim 13, which is:
   8-Fluoro-3-methyl-6-oxo-9-[(R)-3-(thiazol-2-ylamino)-pyrrolidin-1-yl]-2,3-dihydro-6H-1-oxa-3,3a-diaza-phenalene-5-carboxylic acid;
   8-Fluoro-3-methyl-6-oxo-9-[(S)-3-(2,2,2-trifluoro-acetylamino)-pyrrolidin-1-yl]-2,3-dihydro-6H-1-oxa-3,3a-diaza-phenalene-5-carboxylic acid; or
   9(R)-4-Amino-3,3-dimethyl-pyrrolidin-1-yl)-8-fluoro-3-methyl-6-oxo-2,3-dihydro-6H-1-oxa-3,3a-diaza-phenalene-5-carboxylic acid.

15. A method for the preparation of a compound of claim 1 wherein a compound of formula (II) is treated:

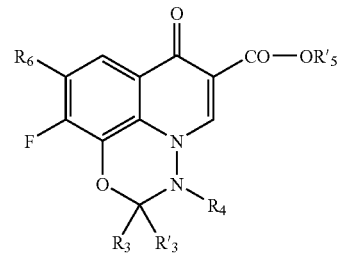

in which $R_3$, $R'_3$, $R_4$ and $R_6$ are as defined in claim 1 and $R'_5$ has the values of $R_5$ defined above or represents another group protecting the carboxy function, by a compound of formula (III):

(III)

in which $R_1$, $R_2$, $R'_2$ and n are defined as in claim 1, in the presence of a base, then, if appropriate, the protective group/s present are eliminated and, if appropriate, esterified by action of an alcohol or of a suitable and salified derivative.

16. A method for the preparation of a compound of claim 1, in which $R_2$ and $R'_2$ represent ($C_1$-$C_6$) alkyl-oxime, wherein a compound of formula (IV) is treated:

(IV)

by an alkoxylamine or a salt thereof.

17. A pharmaceutical composition comprising a compound according to claim 1 and a pharmaceutically acceptable vehicle.

18. A pharmaceutical composition comprising a compound according to claim 11 and a pharmaceutically acceptable vehicle.

19. A pharmaceutical composition comprising a compound according to claim 12 and a pharmaceutically acceptable vehicle.

20. A pharmaceutical composition comprising a compound according to claim 13 and a pharmaceutically acceptable vehicle.

21. A method of treating a bacterial infection in a mammal, comprising administering to the mammal an antibacterially effective amount of a compound of claim 1.

22. A method of treating a bacterial infection according to claim 21, wherein the mammal is not a human.

23. A method of treating a bacterial infection in a mammal, comprising administering to the mammal an antibacterially effective amount of a compound of claim 12.

24. A method of treating a bacterial infection in a mammal, comprising administering to the mammal an antibacterially effective amount of a compound of claim 13.

25. A method of treating a bacterial infection according to claim 24, wherein the mammal is not a human.

26. A compound according to claim 13, which is 8-Fluoro-3-methyl-6-oxo-9-[(R)-3-(thiazol-2-ylamino)-pyrrolidin-1-yl]-2,3-dihydro-6H-1-oxa-3,3a-diaza-phenalene-5-carboxylic acid, or a salt thereof.

27. A compound according to claim 13, which is 8-Fluoro-3-methyl-6-oxo-9-[(S)-3-(2,2,2-trifluoro-acetylamino)-pyrrolidin-1-yl]-2,3-dihydro-6H-1-oxa-3,3a-diaza-phenalene-5-carboxylic acid, or a salt thereof.

28. A compound according to claim 13, which is 9-((R)-4-Amino-3,3-dimethyl-pyrrolidin-1-yl)-8-fluoro-3-methyl-6-oxo-2,3-dihydro-6H-1-oxa-3,3a-diaza-phenalene-5-carboxylic acid, or a salt thereof.

29. A compound according to claim 1, which is (9-[3-(amino-thiazol-2-yl-methyl)-pyrrolidine-1-yl]-8-fluoro-3-methyl-6-oxo-2,3-dihydro-6H-1-oxa-3,3a-diaza-phenalene-5-carboxylic acid, or a salt thereof.

30. A compound according to claim 1, which is (8-fluoro-3-methyl-9-[3-amino-4-(thiazol-2-yl)-pyrrolidin-1-yl]-6-oxo-2,3-dihydro-6H-1-oxa-3,3a-diaza-phenalene-5-carboxylic acid), or a salt thereof.

31. A compound according to claim 1, selected from the group consisting of 8-fluoro-3-methyl-6-oxo-9-[3-(pyrazine-2-ylaminomethyl)-pyrrolidine-1-yl]-2,3-dihydro-6H-1-oxa-3,3a-diaza-phenalene-5-carboxylic acid); (9-[3-(4,5-dimethyl-thiazol-2-ylamino)-pyrrolidine-1-yl]-8-fluoro-3-methyl-6-oxo-2,3-dihydro-6H-1-oxa-3,3a-diaza-phenalene-5-carboxylic acid); (8-fluoro-3-methyl-9-[3-(3-methyl-isoxazol-5-ylamino)-pyrrolidine-1-yl]-6-oxo-2,3-dihydro-6H-1-oxa-3,3a-diaza-phenalene-5-carboxylic acid); and salts thereof.

* * * * *